(12) United States Patent
Hernandez-Brenes et al.

(10) Patent No.: US 10,932,484 B2
(45) Date of Patent: Mar. 2, 2021

(54) **INHIBITORY ACTIVITY OF ACETOGENINS AGAINST *LISTERIA MONOCYTOGENES***

(71) Applicant: INSTITUTO TECHNOLOGICO Y DE ESTUDIOS SUPERIORES DE MONTERREY, Monterrey (MX)

(72) Inventors: Carmen Hernandez-Brenes, Monterrey (MX); Adriana Pacheco Moscoa, Monterrey (MX); Rocio Isabel Diaz de la Garza, Monterrey (MX); Dariana Graciela Rodríguez-Sánchez, Monterrey (MX); Carlos Eduardo Rodríguez-López, Monterrey (MX)

(73) Assignee: INSTITUTO TECNOLOGICO Y DE ESTUDIOS SUPERIORES DE MONTERREY, Monterrey (MX)

( * ) Notice: Subject to any disclaimer, the term of this patent is extended or adjusted under 35 U.S.C. 154(b) by 108 days.

(21) Appl. No.: 15/788,194

(22) Filed: Oct. 19, 2017

(65) Prior Publication Data
US 2018/0103671 A1 Apr. 19, 2018

Related U.S. Application Data

(60) Provisional application No. 62/410,193, filed on Oct. 19, 2016.

(51) Int. Cl.
| | | |
|---|---|---|
| *A23L 33/10* | (2016.01) | |
| *A01N 37/36* | (2006.01) | |
| *A61K 31/22* | (2006.01) | |
| *A61K 8/37* | (2006.01) | |
| *A61Q 19/00* | (2006.01) | |
| *A61K 45/06* | (2006.01) | |
| *A61K 8/36* | (2006.01) | |
| *A61K 8/9789* | (2017.01) | |
| *A61Q 17/00* | (2006.01) | |

(52) U.S. Cl.
CPC ............ *A23L 33/127* (2016.08); *A01N 37/36* (2013.01); *A61K 8/36* (2013.01); *A61K 8/375* (2013.01); *A61K 8/9789* (2017.08); *A61K 31/22* (2013.01); *A61K 45/06* (2013.01); *A61Q 17/005* (2013.01); *A61Q 19/00* (2013.01); *A23V 2002/00* (2013.01); *A61K 2800/92* (2013.01)

(58) Field of Classification Search
None
See application file for complete search history.

(56) References Cited

U.S. PATENT DOCUMENTS

| | | |
|---|---|---|
| 2,550,254 A | 4/1951 | Jensen |
| 5,217,950 A | 6/1993 | Blackburn et al. |
| 5,458,876 A | 10/1995 | Monticello |
| 5,468,490 A | 11/1995 | Huber et al. |
| 5,498,411 A | 3/1996 | Rancurel |
| 5,573,797 A | 11/1996 | Wilhoit |
| 5,573,800 A | 11/1996 | Wilhoit |
| 5,573,801 A | 11/1996 | Wilhoit |
| 6,057,366 A | 5/2000 | Seawright et al. |
| 6,133,313 A | 10/2000 | Thomson et al. |
| 6,326,364 B1 | 12/2001 | Lin et al. |
| 6,582,688 B1 | 6/2003 | Broutin et al. |
| 6,620,446 B2 | 9/2003 | King et al. |
| 7,101,913 B2 | 9/2006 | Arimoto et al. |
| 7,862,842 B2 | 1/2011 | Beltran et al. |
| 9,422,504 B2 | 8/2016 | Msika et al. |
| 9,962,344 B2 | 5/2018 | Baron et al. |
| 2004/0122095 A1 | 6/2004 | Bonaventura et al. |
| 2005/0170027 A1 | 8/2005 | Arimoto et al. |
| 2006/0062813 A1 | 3/2006 | Adachi et al. |
| 2006/0099323 A1 | 5/2006 | Piccirilli et al. |
| 2009/0163590 A1 | 6/2009 | Msika et al. |
| 2010/0034944 A1 | 2/2010 | Beyazova et al. |
| 2011/0217251 A1 | 9/2011 | Meretzki et al. |

(Continued)

FOREIGN PATENT DOCUMENTS

| | | |
|---|---|---|
| CA | 494110 A | 6/1953 |
| GB | 1421129 A | 1/1976 |

(Continued)

OTHER PUBLICATIONS

Summons to Attend Oral Proceedings for European Patent Application Serial No. 14176098.3 (dated Oct. 29, 2019).

(Continued)

*Primary Examiner* — Nannette Holloman
(74) *Attorney, Agent, or Firm* — Troutman Pepper Hamilton Sanders LLP (Rochester)

(57) ABSTRACT

One aspect of the present invention relates to a method of inhibiting growth of *Listeria monocytogenes* on or in a product by applying an inhibitor compound of the formula:

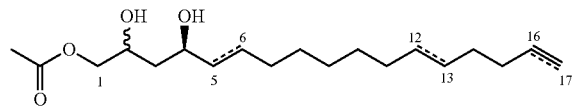

where the dashed lines are optional and represent a double bond or triple bond, and at least one of the dashed lines is present. Also disclosed is a method of inhibiting growth of *Listeria monocytogenes* on or in a subject by treating the subject with that compound. Further aspects of the present invention relate to pharmaceutical compositions, food product compositions, personal care product compositions, and cleaning product compositions comprising the subject inhibitor compounds.

6 Claims, 14 Drawing Sheets

(56) References Cited

U.S. PATENT DOCUMENTS

| | | |
|---|---|---|
| 2011/0250154 A1 | 10/2011 | Meretzki et al. |
| 2012/0071551 A1 | 3/2012 | Mesina et al. |
| 2012/0201884 A1 | 8/2012 | Gokuraju et al. |
| 2012/0294887 A1 | 11/2012 | Saunois et al. |
| 2013/0216488 A1 | 8/2013 | Hernandez-Brenes et al. |
| 2016/0249613 A1 | 9/2016 | Hernandez-Brenes et al. |
| 2017/0055526 A1 | 3/2017 | Hernandez-Brenes et al. |

FOREIGN PATENT DOCUMENTS

| | | | |
|---|---|---|---|
| JP | 2001097828 A | 10/2001 | |
| JP | 2002053474 A | 2/2002 | |
| JP | 2003509506 A | 11/2003 | |
| JP | 2008156240 A | 7/2008 | |
| JP | 2009164558 A | 7/2009 | |
| KR | 20090055387 A * | 6/2009 | ............... A23L 1/30 |
| WO | 9522969 A1 | 8/1953 | |
| WO | 2010/00744 A2 | 1/2010 | |
| WO | 2010026596 A2 | 3/2010 | |

OTHER PUBLICATIONS

Rodriguez-Sanchez et al., "Isolation and Chemical Identification of Lipid Derivatives from Avocado (Persea Americana) Pulp with Antiplatelet and Antithrombotic Activities," Food Function 6:193-203 (2015).

International Search Report and Written Opinion dated Apr. 21, 2016 in PCT/IB2015/002021.

Ciarciaglini et al., "Germination-Induced Bioluminescence, a Route to Determine the Inhibitory Effect of a Combination Preservation Treatment on Bacterial Spores," Applied and Envirmonmental Microbiology 66 (9):3735-3742 (2000).

Heyndrickx, M., "The Importance of Endospore-Forming Bacteria Originating from Soil for Contamination of Industrial Food Processing," Applied and Environmental Soil Science 2011 Article ID 561975 11 pages (2011).

Prusky et al., "Identification of an Antifungal Compound in Unripe Avocado Fruits and its Possible Involvement in the Quiescent Infections of Colletotrichum Gloeosporioides," J. Phytopathology 132: 319-327 (1991).

Jackson et al., "Survival and Growth of Clostridium Perfringens in Commercial No-Nitrate-or-Nitrite-Added (Natural and Organic) Frankfurters, Hams, and Bacon," Journal of Food Protection 74:3 410-416 (2011).

Knapp et al., "Bactericidal Effects of Polyunsaturated Fatty Acids," The Journal of Infectious Diseases 154:1 84-94 (1986).

Slepecky R. and Hemphill E., "The Genus Bacillus-Nonmedical," pp. 530-562 in the Prokaryotes (M. Dworkin, S. Falkow, E. Rosenberg, K. Schleifer, and E. Stackenbrandt eds., 3d ed. 2006).

Third Office Action for China Patent Application Serial No. 201610773165.1 (dated Sep. 25, 2019).

International Search Report, PCT/IB2011/053535, dated Aug. 3, 2012, 4 pages.

Yang, H., et al., "Supercritical fluid CO2 extraction and simultaneous determination of eight annonaceous acetogenins in *Annona* genus plant seeds by HPLC-DAD method," Journal of Pharmaceutical and Biomedical Analysis, vol. 49, (2009), pp. 140-144.

Ugbogu, O.C., et al., "Short Communication: The antimicrobial effect of oils from Pentaclethra macrophylla Bent, Chrysophyllum albidum G Don and Persea gratissima Gaerth F on some local clinical bacteria isolates," African Journal of Biotechnology, vol. 8 (2), pp. 285-287, Jan. 19, 2009.

Sugiyama, T., et al., "Synthesis of All Four Stereoisomers of Antibacteria Component of Avocado," Agric. Biol Chem., vol. 46 (2), pp. 481-485 (1982).

Smola, M., Thesis, "Contribution a l'etude de la formulation et de l'analyse physiochimique de formulations pediatriques microemulsionnees," Unviersite Louis Pastuer Strasbourg I, 2007, 297 pages (English portions included within text).

Rodriguez-Saona, C., et al., "Growth Inhibitory, Insecticidal, and Feeding Deterrent Effects of (12Z, 15Z{-1-Acetoxy-2-Hydroxy-4-Oxo-Heneicosa-12, 15-Diene, a Compound from Avocado Fruit to Spodoptera exigua," Journal of Chemical Ecology, vol. 23, No. 7, (1997), 13 pages.

Rodriguez Carpena, J-G, et al. "Avocado (Persea americana Mill.) Phenolics, in Vitro Antioxidant and Antimicrobial Activities, and Inhibition of Lipid and Protein Oxidation in Porcine Patties," Journal of Agricultural and Food Chemistry, vol. 59, (2011), pp, 5625-5635.

Rayman, M.K., et al., "Nisin: a Possible Alternative or Adjunct to Nitrite in the Preservation of Meats," Applied and Environmental Microbiology, vol. 41, No. 2, Feb. 1981, pp. 375-380.

Ramos-Jerz, M., et al., Dissertation, Phytochemical Analysis of Avocado Seeds (Persea Americana Mill., C.v. Hass), published by Cuvillier Verlag, Oct. 16, 2007, 159 pages.

Prusky, D., et al., "Possible Involvement of an Antifungal Diene in the Latency of Colletotrichum gloeosporioides on Unripe Avocado Fruits," Phytopathotogy, Vo 72, pp. 1578-1582 (1982).

Padron, J.M., et al., "Beta-Hydroxy-alpha. Beta-unsaturated ketones: A new Pharmacophore for the design of anticancer drugs," Bioorganic & Medicinal Chemistry Letters, vol. 16, (2006), pp. 2266-2269.

Oberlies, N.H., et al., "Cytotoxic and Insecticidal Constituents of the Unripe Fruit of Persea americana," J. Nat. Prod., vol. 61, (1998), pp. 781-785.

Neeman, I., et al., "New Antibacterial Agent Isolated from the Avocado Pear," Applied Microbiology, vol. 19, No. 3, Mar. 1970, pp. 470-473.

Murakoshi, S., et al., "Effects of Two Components from the Avocado Leaves (Perseea americana Mill.) and the Related Compounds on the Growth of Silkworm Larvae, Bombyx mori L.," Jap. J. appl. Ent. Zool. vol. 20, pp. 87-91, (1976), Abstract in English.

Maseko, R.B., "Synthesis of Authentic Organic Standards of Antibacterial Compounds Isolated from Avocados," Dissertation, Department of Chemistry and Physics Faculty of Natural Sciences, Tshwane University of Technology, May 2006, 106 pages.

Macleod, J.K., et al., "A Short Enantioselective Synthesis of a Biologically Active Compound from Persea Americana" Journal of Natural Products, vol. 58, No. 8, pp. 1270-1273, Aug. 1995.

Leon, L.G. et al., "beta-Hydroxy-alpha, beta-unsaturated ketones. A new pharmacophore for the design of anticancer drugs, Part 2," ChemMedChem, vol. 3, (2008), pp. 1740-1747.

Kim, O.K., et al., "Novel Nitric Oxide and Superoxide Generation Inhibitors, Persenone A and B, from Avocado Fruit," J Agric Food Chem , vol. 48, (2000), pp. 1557-1563.

Kim, O.K. et al, "Inhibition by (-)—Persenone A-related Compounds of Nitric Oxide and Superoxide Generation from Inflammatory Leukocytes," Biosci Biotechnol Biochem , vol. 64, No. 1, pp. 2500-2503 (2000).

Kim, O.K , et al., An Avocado Constituent, Persenone A, Suppresses Expression of Inducible Forms of Nitric Oxide Synthase and Cyclooxygenase in Macrophages, and Hydrogen Peroxide Generation in Mouse Skin, Biosci. Thotechnol. Biochem., vol. 64, No. 11, p. 2504-2507 (2000).

Kashman, Y., et al , "New Compounds from Avocado Pear," Tetrahedron, vol. 25, pp. 4617-4631, Pergamon Press, (1969).

Kabuki, T. et al., "Characterization of novel antimicrobial compounds from mango (*Mangifera indica* L.) kernel seeds," Food Chemistry, vol. 71, pp. 61-66, (2000).

Hashimura, H. et al., "Acetyl-CoA Carboxylase Inhibitors from Avocado (Persea americana Mill) Fruits," Biosci. Biotechnol. Biochem., vol. 65, No. 7, pp. 1656-1658 (2001).

Greene, T.W. et al., "Protective Groups in Organic Synthesis," Third Edition, Chapter 1: The Role of Protective Groups in Organic Synthesis, 16 pages (1999).

Foucault, A.P. et al., "Counter-current chromatography: instrumentation, solvent selection and some recent applications to natural product purification," Journal of Chromatography A., vol. 808, pp. 3-22 (1998).

Domergue, F. et al , "Antifungal compounds from idioblast cells isolated from avocado fruits," Phytochemistry, vol. 54, pp. 183-189 (2000).

(56) References Cited

OTHER PUBLICATIONS

Chia, T.W.R. et al., "Antimicrobial activity of crude epicarp and seed extracts from mature avocado fruit (Persea americana) of three cultivars," Pharmaceutical Biology, vol. 48, No. 7, pp. 753-756 (2010).
Chang, C-F, et al., "Isolation and Structure Elucidation of Growth Inhibitors for Silk-worm Larvae from Avocado Leaves," Short Communication: Agr. Biol. Chem., vol. 38, No. 5, pp. 1167-1168 (1975).
Canadian Food Directorate, Clostridium botulinum Challenge Testing of Ready-to-Eat Foods, Food Directorate, Health Products and Food Branch. Health Canada, Version No. 1, Issue Date. Nov. 24, 2010, 11 pages.
Butt, A.J. et al., "A novel plant toxin, persin, with in vivo activity in the mammary gland, induces Bim-dependent apoptosis in human breast cancer cells," Molecular Cancer Therapeutics, vol. 5, pp. 2300-2309 (2006).
Bull, S.D. et al., "Synthesis of the Avocado Antifungal, (Z,Z)-2-Hydroxy-4-oxohenicosa-12,15-dien-1-yl Acetate," Aust. J Chem, vol. 47, pp. 1661-1672 (1994).
Brown, B.I., "Isolation of Unpleasant Flavor Compounds in the Avocado (Persea americana)," J. Agr. Food Chem., vol. 20, No. 4, 5 pages (1972).
AOAC Official Method 966.04, Sporicidal Activity of Disinfectants, First Action 1966, Final Action 1967, Revised 2002, 6 pages.
Tang. Y., et al , "Inhibition of Food-Borne Pathogens by T1, a Novel Antimicrobial Peptide as a Potential Food Preservative," USDA National Agricultural Library, International Journal of Food Engineering, vol. 4, No. 4, 2008, (Abstract provided).
First Office Action for China Patent Application No. 201180048894.6 dated Jun. 11, 2014.
Second Office Action for China Patent Application No. 201180048894.6 dated Mar. 13, 2015.
Third Office Action for China Patent Application No. 201180048894.6 dated Oct. 26, 2015.
Notice of Reasons for Rejection for Japanese Patent Application 2013-523692 dated Aug. 24, 2015.
Extended European Search Report for European Patent Application No. 11828227.6 dated Dec. 11, 2013.
Partial European Search Report for European Patent Application No. 14176098.3 dated Feb. 2, 2015.
Idris et al., "Preliminary Phytochemical Screening and Antimicrobial Activity of Seed Extracts of Persea Americana (Avocado Pear)," Bayero Journal of Pure and Applied Sciences 2(1):173-176 (2009).
Extended European Search Report for European Patent Application No. 14176098.3 dated May 29, 2015.
Rodriguez-Saona et al., "Biologically Active Aliphatic Acetogenins from Specialized Idioblast Oil Cells," Current Organic Chemistry 4:1249-1260 (2000).
Rodriguez-Saona et al., "Isolation, Identification,and Biological Activity of Isopersin, a New Compound from Avocado Idioblast Oil Cells," J. Nat. Prod. 61:1168-1170 (1998).
Nagaraj et al., "Antioxidant and Antibacterial Activity of Avocado (Persea gratissima Gaertner) Seed Extract," World Applied Sciences Journal 9(6):695-698 (2010).
Fourth Office Action for China Patent Application No. 201180048894.6 dated Apr. 18, 2016.
Valeri et al., "Phytochemical and Toxicological Study of Pericarp of the Avocado Pear," Rev. Med. Vet. Parasitol (Maracay) vol. 13, pp. 37-58 (1954).
International Preliminary Report on Patentability and Written Opinion for corresponding International Application No. PCT/IB2011/053535 (dated Feb. 12, 2013).
International Search Report and Written Opinion for corresponding International Application No. PCT/IB2011/053535 (dated Aug. 3, 2012).
Chen et al., "Bacteriocins and Their Food Applications," Comprehensive Reviews in Food Science and Food Safety 2(3):82-100 (2003).
Davidson et al., "Antimicrobials in Food," Third Edition, CRC Press, Taylor & Francis Group, Boca Raton, Florida (2005).
Hara-Kudo et al., "Antibacterial Action on Pathogenic Bacterial Spore by Green Tea Catechins," Journal of the Science of Food and Agriculture 85:2354-2361 (2005).
Pierson et al., "Nitrite, Nitrite Alternatives, and the Control of Clostridium Botulinum in Cured Meats," Critical Reviews in Food Science and Nutrition 17(2):141-187 (1983).
Tsukiyama et al., "Antibacterial Activity of Licochalcone A Against Spore-Formng Bacteria," Antimicrobial Agents and Chemotherapy 46(5):1226-1230 (2002).
Castillo-Juarez et al., "Anti-Helicobacter Pylori Activity of Plants Used in Mexican Traditional Medicine for Gastrointestinal Disorders," J. Ethnopharmacol. 122:402-405 (2009).
Hurtado et al., "*Staphylococcus aureus*: Revision of the Mechanisms of Pathogenicity and Physiopathology of *Staphylococcal* Infections," Rev. Soc. Venez. Microbiol. 22:112-118 (2002) (abstract only).
Leite et al., "Chemical Composition, Toxicity and Larvicidal and Antifungal Activities of Persea Americana (Avocado) Seed Extracts," Rev. Soc. Bras. Med. Trop. 42(2):110-113 (2009).
Prusky et al., "The Relationship Between Antifungal Diene Levels and Fungal Inhibition During Quiescent Infection of Unripe Avocado Fruits by Colletotrichum gloeosporioides," Plant Pathol. 40:45-52 (1991).
Raymond-Chia et al., "Antimicrobial Activity of Crude Epicarp and Seed Extracts from Mature Avocado Fruit (Persea Americana) of Three Cultivars," Pharm. Biol. 48:753-756 (2010).
Sivanathan et al., "Biological Activity of Four Antifungal Compounds in Immature Avocado," J. Phytopat. 125:97-109 (1989).
Notice of Reasons for Rejection for Japanese Patent Application 2013-523692 dated Jul. 12, 2016.
Medicinal Chemistry of Natural Products, Nankodo Co., Ltd., pp. 139-141 (2004).
Prusky et al., "Regulation of Natural Resistance of Avocado Fruit for the Control of Postharvest Disease," Proc. of Second World Avocado Congress, pp. 479-484 (1992).
Subsequent Substantive Examination Report for Philippines Patent Application No. 1/2013/500258 dated Jan. 30, 2017.
Office Action for Canadian Patent Application No. 2,807,779 dated Oct. 2, 2017.
Office Action for European Application No. 14176098.3-1454 dated Dec. 13, 2017.
Office Action for Philippines Patent Application No. 1/2013/500258 dated Jan. 5, 2018.
Carman et al., "A Further Synthesis of an Analogue of the Antifungal/Antiherbivore Lipid and Avocado," Aust. J. Chem. 51:955-959 (1998).
Restriction Requirement for U.S. Appl. No. 13/763,262 dated Mar. 3, 2015.
Office Action for U.S. Appl. No. 13/763,262 dated Jun. 5, 2015.
Office Action for U.S. Appl. No. 13/763,262 dated Jan. 6, 2016.
Office Action for Canadian Patent Application No. 2,807,779 dated Jun. 4, 2018.
First Office Action for China Patent Application No. 201610773165.1 dated May 9, 2018 (English Translation).
Office Action for Philippines Patent Application No. 1/2013/500258 dated Jun. 8, 2018.
European Office Action for European Patent Application Serial No. 14176098.3 (dated Jan. 28, 2019).
Chinese Office Action for Chinese Patent Application Serial No. 201610773165.1 (dated Jan. 23, 2019).
Office Action Restriction Requirement for U.S. Appl. No. 15/148,712 (dated Oct. 9, 2018).
Office Action for U.S. Appl. No. 15/148,712 (dated Feb. 11, 2019).
Office Action for U.S. Appl. No. 15/348,740 (dated Feb. 11, 2019).
Office Action Restriction Requirement for U.S. Appl. No. 15/580,933 (dated Jul. 5, 2018).
Office Action for U.S. Appl. No. 15/580,933 (dated Nov. 23, 2018).
Kami et al., "Involvement of Epicatechin in the Regulation of Lipoxygenase Activity During Activation of Quiescent Colletotrichum gloeosporioides Infections of Ripening Avocado Fruits," Physiol. Mol. Plant Pathol. 35:367-74 (1989).

(56) References Cited

OTHER PUBLICATIONS

Kobiler et al., "Compartmentation of Antifungal Compunds in Oil Cells of Avocado Fruit Mesocarp and its Effect on Susceptibility to Colletotrichum gloesporioides," Physiol. Mol. Plant Pathol. 43:319-28 (1993).

Bittner et al., "Isolation and Identification of a Plant Growth Inhibitor from Avocado," Phytochemistry 10:1417-21 (1971).

Gazit et al., "Inhibitor and Auxin Activity in the Avocado Fruit," Physiol. Plant. 27:77-82 (1972).

Kawagishi et al., "Liver Injury Suppressing Compounds from Avocado (Persea americana)," J. Agric. Food Chem. 49:2215-21 (2001).

Kashman et al, "Six New C17-Olefinic and Acetylenic Oxygenated Compounds from Avocado Pear," Israel J. Chem. 2:173-6 (1969).

Prusky, "The use of Antioxidants to Delay the Onset of Anthracnose and Stem End Decay in Avocado Fruits after Harvest," Plant Disease 72:381-4 (1988).

Prusky, "Further Evidence for the Involvement of a Preformed Antifungal Compound in the Latency of Colletotrichum Gloeosporioides on Unripe Avocado Fruits," Physiol. Plant Pathol. 22:189-98 (1983).

\* cited by examiner

INHIBITORY ACTIVITY OF ACETOGENINS AGAINST *LISTERIA MONOCYTOGENES*

This application claims the benefit of U.S. Provisional Patent Application Ser. No. 62/410,193, filed Oct. 19, 2016, which is hereby incorporated by reference in its entirety.

FIELD OF THE INVENTION

The present invention relates to methods of inhibiting growth of *Listeria monocytogenes* on or in products or subjects, and compositions comprising anti-listerial compounds.

BACKGROUND OF THE INVENTION

*Listeria monocytogenes* is a facultative anaerobic Gram-positive bacterium that can cause listeriosis in pregnant women, neonates, elders, and immunocompromised patients. Listeriosis is a foodborne disease with one of the highest mortality rates and can lead to meningitis, sepsis, miscarriage, premature delivery and mother-to-fetus infections (Swaminathan et al., "Listeria Monocytogenes," in Doyle, eds., *Food Microbiology: Fundamentals and Frontiers*, 3rd ed., Washington, D.C.: ASM Press, pp 322-41 (2007) and Schuppler et al., "The Opportunistic Pathogen *Listeria monocytogenes*: Pathogenicity and Interaction With the Mucosal Immune System," *Int. J. Inflam.* 2010:704321-33 (2010). *L. monocytogenes* represents a great challenge to the food industry because of its ability to grow in a wide range of temperatures (0 to 45° C.), pH conditions (4.4 to 9.4), high salt concentrations and persist on food-contact surfaces (Swaminathan et al., "Listeria Monocytogenes," in Doyle, eds., *Food Microbiology: Fundamentals and Frontiers*, 3rd ed., Washington, D.C.: ASM Press, pp 322-41 (2007), and Orgaz et al., "Biofilm Recovery From Chitosan Action: A Possible Clue to Understand *Listeria onocytogenes* Persistence in Food Plants," *Food Control* 32:484-89 (2013). Food products of particular concern are those stored at refrigeration temperatures that are consumed without further cooking, known as ready-to-eat (RTE) foods (Farber et al., "*Listeria monocytogenes*, a Food-Borne Pathogen," *Microbiol. Rev.* 55(3):476-511 (1991), and Zhu et al., "Control of *Listeria monocytogenes* Contamination in Ready-to-Eat Meat Products," *Compr. Rev. Food Sci. Food Saf* 4(2): 34-42 (2005)).

Aware of the risk to consumers, regulatory agencies of different countries have established policies that vary in the degree of control of *L. monocytogenes* in RTE products. These range from zero tolerance in the U.S. (Code of Federal Regulations, "Control of *Listeria monocytogenes* in Ready-to-Eat Meat and Poultry Products," Final Rule, 9 CFR 430 (2003)) to levels below 100 CFU $g^{-1}$ during product shelf life in the E.U. (European Commission, EC European Commission Regulation No. 2073/2005 of 15 Nov. 2005 on "Microbiological Criteria for Foodstuffs," *Off. J. Eur. Union*, L338, 1e26 (2005)). In addition, consumers are increasingly concerned about the presence of synthetic additives in food products, forcing the industry to provide natural alternatives to control food pathogens (Xi et al., "Use of Natural Antimicrobials to Improve the Control of *Listeria monocytogenes* in a Cured Cooked Meat Model System," *Meat Sci.* 88(3):503-11 (2011)).

Acetogenins, naturally occurring lipidic molecules from avocado fruit, have been purified and studied, and show a wide range of bioactivities including antimicrobial, antioxidant, antiplatelet and antithrombotic (WO 2012/042404 A2 to Hernandez-Brenes et al.; Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013); Rodríguez-Sánchez et al., "Activity-Guided Identification of Acetogenins as Novel Lipophilic Antioxidants Present in Avocado Pulp (*Persea americana*)," *J. Chromatogr. B* 942-943:37 45 (2013); and Rodríguez-Sánchez et al., "Isolation and Chemical Identification of Lipid Derivatives From Avocado (*Persea americana*) Pulp With Antiplatelet and Antithrombotic Activities," *Food Funct.* 6(1):193-203 (2015)). Two new structures were reported and, recently, two putative acetogenins were identified in a study with 22 avocado cultivars (Rodríguez-López et al., "A Targeted Metabolomics Approach to Characterize Acetogenin Profiles in Avocado Fruit (*Persea americana* Mill)," *RSC Adv.* 5:106019-29 (2015)), extending the acetogenin pool to eight molecules.

The antimicrobial properties of avocado extracts have been reported against bacteria, yeast, fungi, and protozoa, which represent important pathogens including *Salmonella typhi, Shigella dysenteriae, Candida albicans, Staphylococcus aureus* MRSA, *Mycobacterium tuberculosis, L. monocytogenes* and *Leishmania* (Neeman et al., "New Antibacterial Agent Isolated From the Avocado Pear," *Appl. Microbiol.* 19:470-73 (1970); Sivanathan et al., "Biological Activity of Four Antifungal Compounds in Immature Avocado," *J. Phytopathol.* 125:97-109 (1989); Domergue et al., "Antifungal Compounds From Idioblast Cells Isolated From Avocado Fruits," *Phytochemistry* 54(2):183-9 (2000); Castillo-Juarez et al., "Anti-*Helicobacter pylori* Activity of Plants Used in Mexican Traditional Medicine for Gastrointestinal Disorders," *J. Ethnopharmacol.* 122:402-5 (2009); Leite et al., "Chemical Composition, Toxicity and Larvicidal and Antifungal Activities of *Persea americana* (Avocado) Seed Extracts," *Rev. Soc. Bras. Med. Trop.* 42:110-13 (2009); Ugbogu et al., "The Antimicrobial Effect of Oils From *Pentaclethra macrophylla* Bent, *Chrysophyllum albidum* G. Don and *Persea gratissima* Gaerth F on Some Local Clinical Bacteria Isolates," *Afr. J. Biotechnol.* 8:285-87 (2009); Raymond-Chia et al., "Antimicrobial Activity of Crude Epicarp and Seed Extracts From Mature Avocado Fruit (*Persea americana*) of Three Cultivars," *Pharm. Biol.* 48:753-756 (2010); Rodriguez-Carpena et al., "Avocado (*Persea americana* Mill.) Phenolics, in Vitro Antioxidant and Antimicrobial Activities, and Inhibition of Lipid and Protein Oxidation in Porcine Patties," *J. Agric. Food Chem.* 59(10):5625-35 (2011); Dharmaratne et al., "Antimicrobial and Antileishmanial Active Acetogenins From Avacado (*Persea americana*) Fruits," *Planta Med.* 78:34 (2012); Lu et al., "Secondary Metabolites From the Unripe Pulp of *Persea americana* and Their Antimycobacterial Activities," *Food Chem.* 135:2904-09 (2012); and Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013)). However, these studies encompass multiple extraction methods with a limited number of isolated molecules, and, consequently, activity is rarely linked to chemical identity. Only six acetogenins and their poly-hydroxylated fatty alcohol derivatives have been tested but none against *L. monocytogenes* (Neeman et al., "New Antibacterial Agent Isolated From the Avocado Pear," *Appl. Microbiol.* 19:470-73 (1970); Dharmaratne et al., "Antimicrobial and Antileishmanial Active Acetogenins From Avacado (*Persea americana*) Fruits," *Planta Med.* 78:34 (2012); and Lu et al., "Secondary Metabolites From the Unripe Pulp of *Persea americana* and Their Antimycobacterial Activities," *Food Chem.* 135:2904-09 (2012)). Applicants previously reported that isolated acetogenins control important food pathogens such as sporulated bacteria (WO 2012/042404 A2 (2012) to Hernandez-Brenes et al., and Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013)).

High standards regarding *L. monocytogenes* control, especially in food products, and consumer demands for products without synthetic additives represent a challenge to industry.

The present invention is directed to overcoming these and other deficiencies in the art by providing methods, compounds, and compositions for the control of *L. monocytogenes* on or in products.

SUMMARY OF THE INVENTION

One aspect of the present invention relates to a method of inhibiting growth of *Listeria monocytogenes* on or in a product. This method comprises providing an inhibitor compound of the formula:

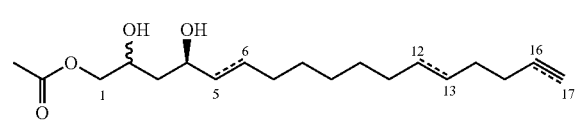

where the dashed lines are optional and represent a double bond or triple bond, and at least one of the dashed lines is present, and applying the inhibitor compound on or in the product to inhibit growth of *Listeria monocytogenes* on or in the product.

A second aspect of the present invention relates to a method of inhibiting growth of *Listeria monocytogenes* on or in a subject. This method comprises providing an inhibitor compound of the formula

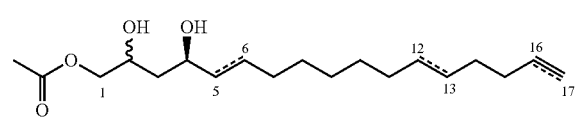

where the dashed lines are optional and represent a double bond or triple bond, and at least one of the dashed lines is present, and treating a subject with the inhibitor compound to inhibit growth of *Listeria monocytogenes* in the subject.

A third aspect of the present invention relates to a pharmaceutical composition comprising an inhibitor compound of either of the following formulae:

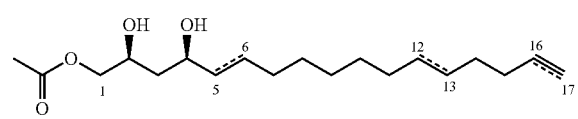

where the dashed lines are optional and represent a double bond or triple bond, and exactly one of the dashed lines is present, or

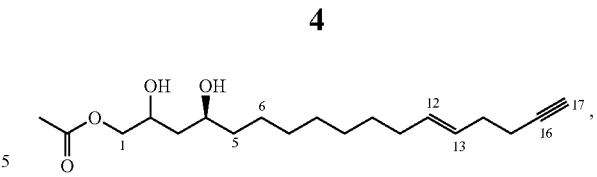

and a pharmaceutically acceptable carrier.

A fourth aspect of the present invention relates to a food product composition comprising a food product and an inhibitor compound of either of the following formulae:

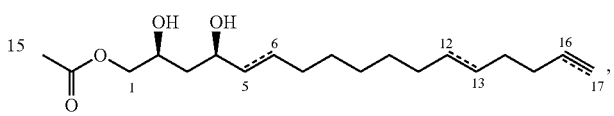

where the dashed lines are optional and represent a double bond or triple bond, and exactly one of the dashed lines is present, or

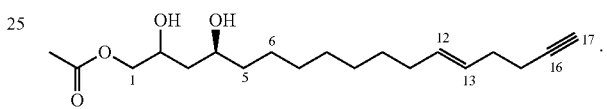

A fifth aspect of the present invention relates to a personal care product composition comprising a personal care product and an inhibitor compound of either of the following formulae:

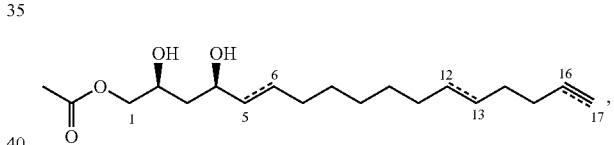

where the dashed lines are optional and represent a double bond or triple bond, and exactly one of the dashed lines is present, or

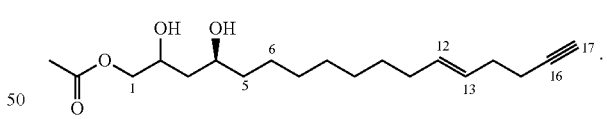

A sixth aspect of the present invention relates to a cleaning product composition comprising a cleaning product and an inhibitor compound of either of the following formulae:

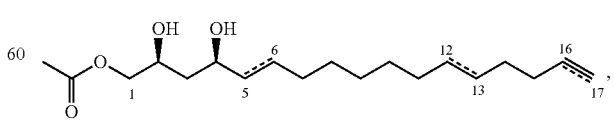

where the dashed lines are optional and represent a double bond or triple bond, and exactly one of the dashed lines is present, or

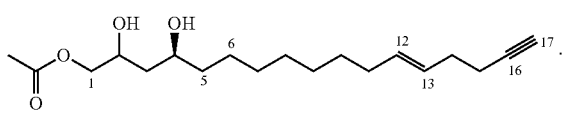 [SMILES: C#CCC/C=C/CCCCCCC[C@H](O)CC(O)COC(C)=O]

An advantage of this invention is that acetogenins possess anti-listerial activity comparable to that of synthetic commercial antimicrobials, and as a result enriched extracts or isolated compounds can be incorporated into ready-to-eat (RTE) foods or other products as natural additives to control *L. monocytogenes*. As a waste product of the industry, avocado seeds represent a good source of these molecules.

BRIEF DESCRIPTION OF THE DRAWINGS

FIG. 6A shows Culture tubes at time 0 h and 24 h. FIG. 6B shows representative flow cytometry (FC) dot plots of propidium iodide (PI) versus SYBR®Safe (SyBR-G) showing bacterial groups at 24 h. FIG. 6C shows median fluorescence intensity of PI histograms from FC analysis at 24 h. FIG. 6D shows percentage of cell debris from FC analysis, lower-left quadrant, at 24 h. MIC values were 15.6 and 32.0 mg L$^{-1}$ for Avosafe® and Mirenat®, respectively. Values represent mean±standard deviation of independent replicates (n=3). Different letters indicate significant differences (LSMeans Student's t, alpha=0.05, n=18).

FIG. 8A shows plate counts of *Listeria monocytogenes*. FIG. 8B shows aerobic plates count of native flora. Values represent average ±SD (n=3).

DETAILED DESCRIPTION OF THE INVENTION

Figures 1A, 1B:
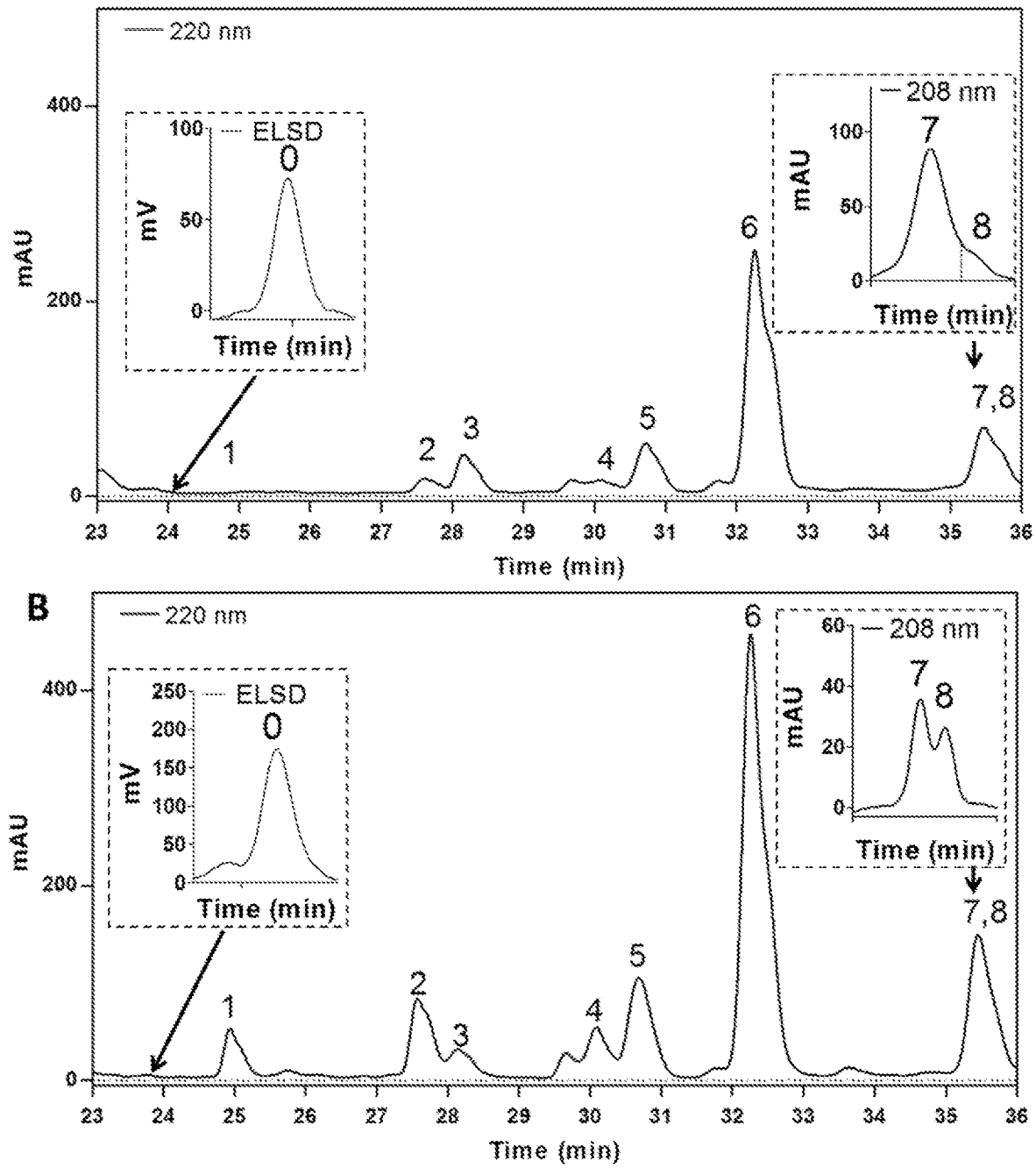
FIGS. 1A-1B shows chromatographic profiles of acetogenins from Hass avocado pulp (FIG. 1A) and seed (FIG. 1B), determined by HPLC separation coupled to ELSD (compound 0), HPLC-PDA at 220 nm (compounds 1-6) and HPL-PDA at 208 nm (compounds 7-8). Each peak corresponds to one acetogenin and numbers were assigned according to elution order from the HPLC column. Details on chemical identity are specified in Table 2.

One aspect of the present invention relates to a method of inhibiting growth of *Listeria monocytogenes* on or in a product. This method comprises providing an inhibitor compound of the formula:

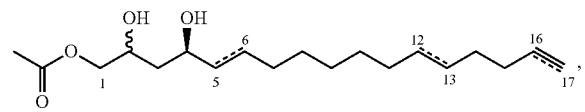

where the dashed lines are optional and represent a double bond or triple bond, and at least one of the dashed lines is present, and applying the inhibitor compound on or in the product to inhibit growth of *Listeria monocytogenes* on or in the product In certain embodiments, the inhibitor compound has the formula:

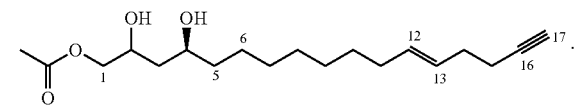 [SMILES: C#CCC/C=C/CCCCCCC[C@H](O)CC(O)COC(C)=O]

In other embodiments, the inhibitor has the formula

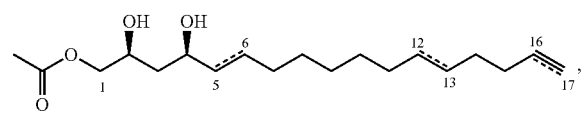

where the dashed lines are optional and represent a double bond or triple bond, and exactly one of the dashed lines is present.

In other embodiments, the inhibitor has the formula

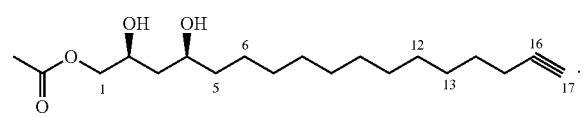

In other embodiments, the inhibitor has the formula

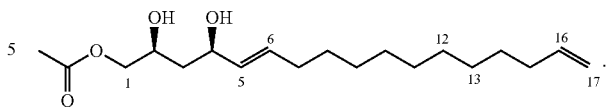

As used herein, inhibiting the growth of *Listeria monocytogenes* encompasses slowing bacterial growth, halting bacterial growth, or preventing bacterial growth of *Listeria monocytogenes*. The slowing, halting, or preventing of bacterial growth of *Listeria monocytogenes* may be described as 'anti-listerial' activity. Inhibiting growth of the bacteria includes killing of the bacteria.

A "treated product", as used herein, refers to a product to which a compound or composition of the present invention has been applied. Application of the compound or composition may be on the product or in the product.

Methods for the detection and enumeration of bacteria are known in the art, including methods for detecting and enumerating *Listeria monocytogenes*. Non-limiting examples of such methods are described, for example, in Hitchins et al., "BAM: Detection and Enumeration of *Listeria monocytogenes*," U.S. Food and Drug Administration Bacteriological Analytical Manual, Chapter 10 (2016), Valimaa et al., "Rapid Detection and Identification Methods for *Listeria monocytogenes* in the Food Chain—A Review," *Food Control*, 55:103-114 (2015), and Jadhav et al., "Methods Used for the Detection and Subtyping of *Listeria monocytogenes*," *Journal of Microbiol. Methods* 88(3):327-341 (2012), which are hereby incorporated by reference in their entirety.

Products to which the present invention may be applied include any product which harbors or may harbor *Listeria monocytogenes*, to which a compound or composition may be applied.

In one embodiment, the product is a food product. It is contemplated that the food product may be selected from the group consisting of fish, crustaceans, fish substitutes, crustacean substitutes, meat, meat substitutes, poultry products, vegetables, fruits, greens, sauces, emulsions, beverages, juices, wines, beers, dairy products, soups, egg-based products, dressings, jams, jellies, syrups, honeys, grain-based products, baked goods, snacks, confectionery products, purees, and combinations thereof. It is further contemplated that the food product may be a refrigerated food product.

The term "food" or "food product" encompasses all edible nutritive substances and compositions, especially those intended for human consumption, and includes unprocessed, as well as processed, e.g., cooked, nutritive substances and compositions. The expression "on or in a food product" refers to all external surfaces and interior surfaces and/or portions of a food that are resident or possibly resident to *Listeria monocytogenes*.

The present method and system provide for applying an inhibitor compound or composition employing any method or apparatus suitable for application. For example, the method can be carried out by applying the compound or composition by spray, immersion, foam treatment, gel treatment, or any other method known to those of skill in the art for applying compounds or compositions on or in food products.

Application of the compound or composition can be carried out under any conditions sufficient to result in anti-listerial activity. Conditions sufficient to result in antilisterial activity vary depending on the compound or composition being used and the product being treated. Conditions that may vary include, but are not limited to application method, exposure time, temperature, pH, drying time, salinity, and water content.

One method for application in or on a food product employs a pressure spray including the compound or composition. During application of the spray solution on the food product, the surface of the food product can be moved with mechanical action, preferably agitated, rubbed, brushed, etc. Agitation can be by physical scrubbing of the food product, through the action of the spray solution under pressure, through sonication, or by other methods. Agitation increases the efficacy of the spray solution in inhibiting the growth of Listeria monocytogenes, perhaps due to better exposure of the solution into the crevasses or small colonies containing the micro-organisms. The spray solution, before application, can optionally be heated to increase efficacy. The spray anti-listerial composition can be left on the food product for a sufficient amount of time to suitably inhibit the growth of Listeria monocytogenes, and then rinsed, drained, or evaporated off the food product.

Application of the material by spray can be accomplished using a manual spray wand, an automatic spray of food product moving along a production line using multiple spray heads to ensure complete contact, or other spray apparatus. One automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the compounds and compositions of the invention. These steam jets can be used in combination with cooling water to ensure that the treatment reaching the food product surface is less than 65° C., preferably less than 60° C. The temperature of the spray on the food product is important to ensure that the food product is not substantially altered (cooked) by the temperature of the spray. Virtually any useful spray pattern can be utilized.

Immersing a food product in a liquid composition can be accomplished by any of a variety of methods known to those of skill in the art. For example, the food product can be placed into a tank or bath containing the composition. Alternatively, the food product can be transported or processed in a flume of the composition. The washing solution may be agitated to increase the efficacy of the solution. Agitation can be obtained by conventional methods, including ultrasonics, aeration by bubbling air through the solution, by mechanical methods, such as strainers, paddles, brushes, pump driven liquid jets, or by combinations of these methods. The composition can be heated to increase the efficacy of the solution. After the food product has been immersed for a time sufficient for the desired anti-listerial effect, the food product can be removed from the bath or flume and the composition can be rinsed, drained, or evaporated off the food product.

The food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. At time of use, compressed air can be injected into the mixture, then applied to the food product surface through a foam application device such as a tank roamer or an aspirated wall mounted roamer.

In another alternative embodiment of the present invention, the food product can be treated with a thickened or gelled version of the composition. In the thickened or gelled state, the washing solution remains in contact with the food product surface for longer periods of time, thus increasing the anti-listerial efficacy. The thickened or gelled solution will also adhere to vertical surfaces. The composition can be thickened or gelled using existing technologies such as: propylene glycol, xanthan gum, polymeric thickeners, cellulose thickeners, or the like. Rod micelle forming systems, such as amine oxides, and anionic counter ions could also be used. The thickeners or gel forming agents can be used either in the concentrated product or mixing with the washing solution, at time of use.

In one embodiment, the product is a personal care product.

Personal care product compositions are used to form a personal care product in an appropriate application form and packaging, as is well-known in the art.

Personal care products and compositions to form them as described herein are used for the purpose of cleansing, conditioning, grooming, beautifying, promoting attractiveness, or otherwise enhancing or altering the appearance of the human body and are applied to the human skin or scalp.

These include products applied to and left on the skin or scalp, for example creams, salves, lotions, and ointments for hand, face or body, perfumes, eau de Cologne, eau de toilet, deodorants, antiperspirants, and products applied but rinsed off such as soaps, liquid soaps, shower gels, shampoos.

These products can, for example, take various forms of application, for example sticks, roll-ons, sprays, pump-sprays, aerosols, soap bars, powders, solutions, gels, creams, balms and lotions.

Many personal care products will be formulated as an emulsion or other lipid-containing products and these form a particular aspect. Lipids are often included for example into washing formulations including liquid soaps or washing lotions to provide an oil replenishing effect. Preservative-enhancing compounds as hereinabove defined allow the formulation of preserved emulsions or formulations comprising lipids and/or detergents where the activity (the bactericidal, fungicidal and in particular the sporicidal effect) is not lost due to the presence of the lipid base and/or detergents or surfactants.

Depending on the nature of the personal care product, compounds of the present invention may also be combined with art-recognized quantities of other excipients commonly employed in these products; useful selections may be found in CTFA Cosmetic Ingredient Handbook, J. M. Nikitakis (ed.), 1st ed., The Cosmetic, Toiletry and Fragrance Association, Inc., Washington, 1988, which is hereby incorporated by reference in its entirety.

In general, excipients may, for example, include colorants, fragrances, solvents, surfactants, colorants, opacifiers, buffers, antioxidants, vitamins, emulsifiers, UV absorbers, silicones and the like. All products can also be buffered to the desired pH using commonly-available excipients in a known manner.

It is contemplated that the personal care product may be selected from the group consisting of creams, gels, powders, lotions, sunscreens, lipstick, body wash, herbal extracts, toothpaste, mouthwash, deodorant, antiperspirant, formulations that support or prevent the growth of bacteria, and combinations thereof In one embodiment, the product is a surface to be treated.

The compounds and composition of this invention may be used for inhibiting the growth of *Listeria monocytogenes* on a variety of surfaces. The compositions of this invention are contacted with the surface to be treated in any of a variety of methods. Conventional sanitizers, disinfectants or cleaners are applied to a surface (e.g. spray, immersion, wipe, etc.). The composition is then permitted to remain in contact with the surface being treated for a period of time sufficient to inhibit the growth of *Listeria monocytogenes* on the treated surface. The time required for effective treatment of a given surface is dependent upon a variety of factors including, but not limited to, the particular anti-listerial composition applied, quantity of *Listeria monocytogenes* present and ambient conditions. While not required, the surface can then be rinsed or wiped clean to remove the composition. In some embodiments, the surface is a hard surface.

It is contemplated that the surface to be treated is selected from the group consisting of counter tops, doors, windows, handles, surgical equipment, medical tools, slaughterhouse equipment, food processing equipment, food storage containers, contact surfaces that can contaminate humans or animals, and combinations thereof.

In certain embodiments, the surface to be treated is a food processing equipment product or a food storage container product. It is contemplated that the food processing equipment product or food storage container product is selected from the group consisting of meat mincer, grinder, tenderizer, cutter, slicer, meat saw, poultry cutter, stuffer, mixer, vacuum tumbler, fruit cutter, fruit peeler; ice-cream machine, vacuum sealer, packaging equipment, conveyor belt, sandwich preparation table, pizza preparation table, salad case, refrigerator, freezer, display cabinet, ice-cream display cabinet, cake show case, supermarket showcase, cold storage room, pickle refrigeration, countertop refrigerator, or combinations thereof.

In one embodiment, the inhibitor compound is applied as a component of a composition, with the composition further comprising a carrier. Non-limiting examples of carriers include water, solvent such as an oil, alcohol or polyol, or encapsulating material. Compositions of the present invention are formulated in accordance with their mode of application. Compositions may be formulated in any food grade vehicle or carrier. Such carriers are known in the art. Non-limiting examples of food grade vehicles or carriers include agar, maltodextrin, gelatin, cellulose, starch, chitosan, pectin, β-cyclodextrin, glycols such as propylene glycol, polyols such as glycerine, sorbitol, mannitol, or polyethylene glycol, oil such as peanut oil, cottonseed oil, sunflower oil, sesame oil, olive oil, corn oil, or soybean oil, coconut oil, cocoa butter, polyoxyethylene sorbitan monolaurate (Tween 20), polyoxyethylene sorbitan monooleate (Tween 80), ethanol, dimethyl sulfoxide, soy lecithin, propylethilene glycol, whey protein, and mixtures thereof. In certain embodiments, the carrier is present at about 0.01 wt % to about 99.9 wt %. In other embodiments, the carrier is present at about 3 wt % to about 99.9 wt %, about 25 wt % to about 99.9 wt %, about 50 wt % to about 99.9 wt %, about 75 wt % to about 99.9%, about 85 wt % to about 99.9 wt %, about 90 wt % to about 99.9 wt %, or about 95 wt % to about 99.9 wt %.

In one embodiment, the inhibitor compound is applied as a component of a composition, with the composition further comprising a surfactant. The surfactant can be nonionic, anionic or cationic in nature. Examples of useful surfactant types include, but are not limited to the following: lecithin, polyoxyethylene sorbitan monolaureate (Tween 20), polyoxyethylene sorbitan monooleate (Tween 80), macrogol 15 hydroxystearate, polyglyceryl-6 dioleate, fatty acids, monoglycerides.

All compositions can be buffered to a desired pH in a known manner. In certain embodiments, the pH range is between about 2 to about 10.

In certain embodiments, the composition further comprises an antimicrobial sub stance.

Antimicrobial substances may kill or inhibit the growth of any microbe, including, but not limited to fungi, viruses, protozoa, archaea, and bacteria including *Listeria monocytogenes*. Non-limiting examples of antimicrobial substances include nitrite compounds, nisin, bacteriocins, ethyl lauroyl arginate, ethylene diaminetetraacetic acid compounds, ascorbic acid compounds, benzoic acid compounds, lysosome, sorbic acid compounds, parabens, sulfur dioxide compounds, sulfite compounds, acetic acid compounds, boric acid compounds, lactic acid compounds, dimethyl dicarbonate, diethyl dicarbonate, natamycin, lactoferrin, fatty acids, esters, and combinations thereof. In certain embodiments, the antimicrobial substance is present at a concentration of about 0.1 mg/L to about 512 mg/L. In other embodiments, the antimicrobial substance is present at a concentration of about 0.01 mg/L to about 128 mg/L, about 0.01 mg/L to about 32 mg/L, about 0.01 mg/L to about 16 mg/L, about 0.01 mg/L to about 8 mg/L, about 0.01 mg/L to about 4 mg/L, about 0.01 mg/L to about 2 mg/L, or about 0.01 mg/L to about 1 mg/L.

In certain embodiments, the composition can be subjected to further processing to produce micro or nanoparticle systems improving the color, flavor, solubility, sensitivity to pressure, and sensitivity to heat and light of the inhibitor compound. Such processing can include top-down or mechanical methods, which involve particle size reduction, and bottom-up methods or chemical processes, in which micro or nanoparticles are created from smaller molecules, such as lipids or proteins.

Effective amounts of the compounds or compositions of the present invention will depend upon the mode of application.

In certain embodiments, the inhibitor compound in the composition is applied at a concentration of at least about 15.6 mg L$^{-1}$ to at least about 31.2 mg L$^{-1}$.

In certain embodiments, inhibition is carried out against the non-motile stage of *Listeria monocytogenes*.

As used herein, the "non-motile stage of *Listeria monocytogenes*" refers to conditions under which the *Listeria monocytogenes* do not synthesize flagella, for example, at human body temperatures (37° C.).

A second aspect of the present invention relates to a method of inhibiting growth of *Listeria monocytogenes* on or in a subject. This method comprises providing an inhibitor compound of the formula where the dashed lines are optional and represent a double bond or triple bond, and at least one of the dashed lines is present, and treating a subject with the inhibitor compound to inhibit growth of *Listeria monocytogenes* on or in the subject.

In certain embodiments, the inhibitor compound has the formula:

![structure with OH at position 3, OH at position 5, double bond between 12-13, triple bond between 16-17]

In other embodiments, the inhibitor has the formula

![structure with OH groups and dashed bonds between 5-6, 12-13, and 16-17]

where the dashed lines are optional and represent a double bond or triple bond, and exactly one of the dashed lines is present.

In other embodiments, the inhibitor has the formula

![structure with OH groups and triple bond between 16-17]

In other embodiments, the inhibitor has the formula

![structure with OH groups, double bond between 5-6, and double bond between 16-17]

In one embodiment the method further comprises selecting a subject having *Listeria monocytogenes*, where the inhibitor compound is administered to the selected subject.

In the context of a subject having *Listeria monocytogenes*, inhibiting the growth of *Listeria monocytogenes* on or in said subject includes, without limitation, slowing growth of the *Listeria monocytogenes*, halting growth of the *Listeria monocytogenes*, killing the *Listeria monocytogenes*, and/or eliminating the *Listeria monocytogenes* from the subject.

In another embodiment, the method further comprises selecting a subject susceptible to having *Listeria monocytogenes*, where the inhibitor compound is administered to the selected subject.

In the context of a subject susceptible to having *Listeria monocytogenes*, treatment of said subject includes, without limitation, preventing the growth of *Listeria monocytogenes* on or in the subject, and reducing the risk of the growth of *Listeria monocytogenes* on or in a subject.

A subject having *Listeria monocytogenes* may also be describe as having a *Listeria monocytogenes* infection, although as is understood in the art, a subject having *Listeria monocytogenes* may have a sub-clinical amount of *Listeria monocytogenes*, which has not yet developed to the point of infection.

A "treated subject", as used herein, refers to a subject to which a compound or composition of the present invention has been administered.

In accordance with this aspect, the target "subject" encompasses any animal, for example, a mammal, such as a human. In the context of administering a composition of the disclosure for purposes of inhibiting the growth of *Listeria monocytogenes* in a subject, the target subject encompasses any subject that has or is at risk of having *Listeria monocytogenes*. Susceptible subjects include infants and juveniles, as well as immunocompromised juvenile, adults, and elderly adults. However, any infant, juvenile, adult, or elderly adult or immunocompromised individual having or at risk for having *Listeria monocytogenes* can be treated in accordance with the methods described herein. Other suitable subjects include those subjects which may have or are at risk for developing a condition resulting from *Listeria monocytogenes*, i.e., listeriosis.

In one embodiment, the compound or compositions are administered prophylactically to prevent, delay, or inhibit the development of *Listeria monocytogenes* in a subject at risk of developing a listerial infection or associated condition. In one aspect, prophylactic administration of one or more compounds described herein is effective to fully prevent growth of *Listeria monocytogenes* on or in an individual. In other embodiments, prophylactic administration is effective to prevent the full extent of bacterial growth or infection that would otherwise develop in the absence of such administration, i.e., substantially prevent, inhibit, or minimize *Listeria monocytogenes* on or in an individual.

In another embodiment, the compounds or compositions as described herein are administered therapeutically to an individual having *Listeria monocytogenes* to inhibit the progression and further bacterial growth or development of infection, i.e., to inhibit and/or prevent the spread of *Listeria monocytogenes* or a *Listeria monocytogenes* infection to other cells in an individual, decrease infection, and to treat or alleviate one or more symptoms of infection.

Therapeutically effective amounts of the compounds describe herein are determined in accordance with standard procedures, which take numerous factors into account, including, for example, the concentrations of the compound in a pharmaceutical composition, the mode and frequency of administration, the severity of the *Listeria monocytogenes* infection to be treated (or prevented), and subject details, such as age, weight and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer a composition comprising the compounds described herein in a single dose or in accordance with a multi-dosing protocol until a dosage is reached that provides the desired or required prophylactic or therapeutic effect. The progress of this therapy can be easily monitored by conventional assays. In prophylactic applications, a relatively low dosage is administered at relatively infrequent intervals over a long period of time. In therapeutic applications, a relatively high dosage at relatively short intervals (e.g., as little as 15 minutes, 30 minutes, 60 minutes, 90 minutes or even 2 or 3 hours) is sometimes required until progression of the disease is reduced or terminated, and preferably until the subject shows partial or complete amelioration of symptoms of disease.

The therapeutically effective amount, i.e., the dosage sufficient for a subject having *Listeria monocytogenes* that is sufficient to slow or prevent the spread or severity of *Listeria monocytogenes* or a *Listeria* infection, and/or the dosage sufficient to prevent, alleviate (either partially or completely) a Listerial infection associated condition. Such therapeutically effective amounts vary by individual, but may range from 0.1 to 10 mg/kg body weight, for example 1, 2, 3, 4, 5, 6, 7, 8, 9 or 10 mg/kg, but may even higher, for example 15, 20, 30, 40, 50, 60, 70, 80, 90 or 100 mg/kg. A fixed unit dose may also be given, for example, 50, 100, 200, 500 or 1000 mg, or the dose may be based on the patient's surface area, e.g., 400, 300, 250, 200, or 100 mg/m$^2$. Usually between 1 and 8 doses, (e.g., 1, 2, 3, 4, 5, 6, 7 or 8) may be administered to treat infection, but 10, 12, 20 or more doses may be given depending on the severity of infection. Administration of compounds of the present disclosure may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

The therapeutic compositions of the present disclosure can be administered alone or as part of a combination therapy in conjunction with one or more other active agents, depending upon the nature of the *Listeria monocytogenes* that is being treated. Such additional active agents include anti-infective agents, antibiotic agents, and antimicrobial agents that are readily known in the art.

The mode of administration of the compounds and compositions described herein may be any suitable route that delivers the compound(s) to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by, for example, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

It is contemplated that administering may be carried out orally, dermally, parenterally, nasally, opthalmically, optically, sub-lingually, rectally, gastricly, vaginally, or using combinations thereof.

In one embodiment, the inhibitor compound is applied as a component of a composition, and the composition further comprises a pharmaceutical carrier.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material, involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Selection of a suitable pharmaceutical carrier may depend on the route of administration. In accordance with this aspect of the present invention, the composition can be formulated for oral, rectal, intravenous, intramuscular, intraperitoneal, intranasal (e.g., by nasogastric tube), parenteral, topical, subcutaneous, intra-arterial, intracranial, or intradermal administration.

In certain embodiments, the inhibitor compound is applied as a component of a composition, with the composition further comprising a surfactant. The surfactant can be nonionic, anionic or cationic in nature. Examples of useful surfactant types include, but are not limited to the following: lecithin, polyoxyethylene sorbitan monolaureate (Tween 20), polyoxyethylene sorbitan monooleate (Tween 80), macrogol 15 hydroxystearate, polyglyceryl-6 dioleate, fatty acids, monoglycerides.

In certain embodiments, the composition further comprises an antimicrobial substance.

Antimicrobial substances may kill or inhibit the growth of any microbe, including, but not limited to fungi, viruses, protozoa, archaea, and bacteria, including but not limited to *Listeria monocytogenes*. Non-limiting examples of antimicrobial substances include nitrite compounds, nisin, bacteriocins, ethyl lauroyl arginate, ethylene diaminetetraacetic acid compounds, ascorbic acid compounds, benzoic acid compounds, lysosome, sorbic acid compounds, parabens, sulfur dioxide compounds, sulfite compounds, acetic acid compounds, boric acid compounds, lactic acid compounds, dimethyl dicarbonate, diethyl dicarbonate, natamycin, lactoferrin, fatty acids, esters, and combinations thereof.

In certain embodiments, the composition can be subjected to further processing to produce micro or nanoparticle systems improving the color, flavor, solubility, sensitivity to pressure, and sensitivity to heat and light of the inhibitor compound. These processing can include top-down or mechanical methods, which involve particle size reduction, and bottom-up methods or chemical processes, in which micro or nanoparticles are created from smaller molecules, such as lipids or proteins.

Effective amounts of the compounds or compositions of the present invention will depend upon the mode of application.

In certain embodiments, the inhibitor compound in the composition is applied at a concentration of at least about 15.6 mg L$^{-1}$ to at least about 31.2 mg L$^{-1}$.

In certain embodiments, inhibition is carried out against the non-motile stage of said *Listeria monocytogenes*.

By "compound(s) of the invention" and equivalent expressions, it is meant compounds herein described, which expression includes the prodrugs, the pharmaceutically acceptable salts, the oxides, and the solvates, e.g. hydrates, where the context so permits.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

The term "solvate" refers to a compound in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in *Remington, The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed by the present invention.

The term "pharmaceutically acceptable salt" refers to salts prepared from pharmaceutically acceptable non-toxic acids or bases including inorganic acids and bases and organic acids and bases.

A third aspect of the present invention relates to a pharmaceutical composition comprising an inhibitor compound of either of the following formulae:

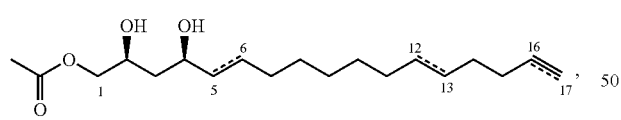

where the dashed lines are optional and represent a double bond or triple bond, and exactly one of the dashed lines is present, or

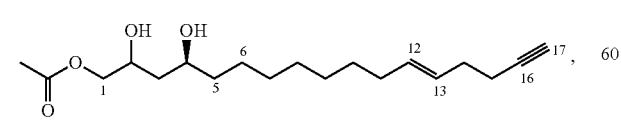

and a pharmaceutically acceptable carrier. The compositions of this aspect of the invention can be formulated as described supra.

In certain embodiments, the inhibitor has the formula

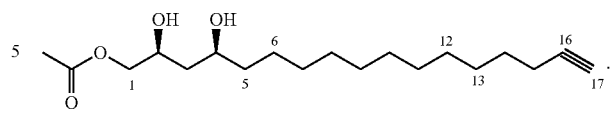

In other embodiments, the inhibitor has the formula

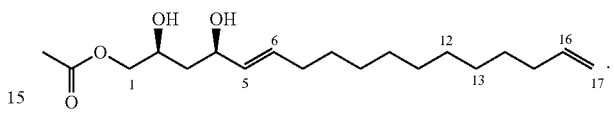

A fourth aspect of the present invention relates to a food product composition comprising a food product and an inhibitor compound of either of the following formulae:

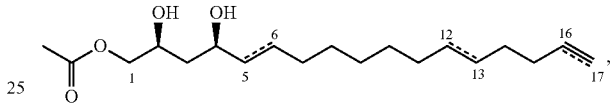

where the dashed lines are optional and represent a double bond or triple bond, and exactly one of the dashed lines is present, or

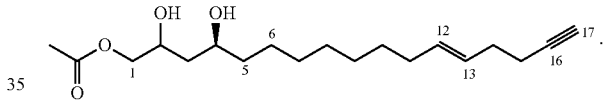

The compositions of this aspect of the invention can be formulated as described supra.

In certain embodiments, the inhibitor has the formula

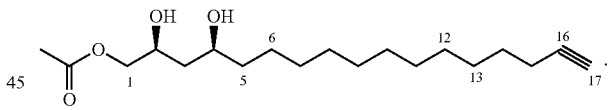

In other embodiments, the inhibitor has the formula

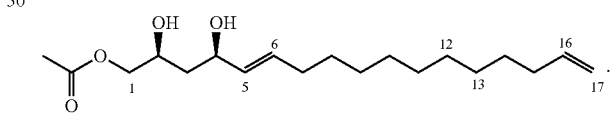

A fifth aspect of the present invention relates to a personal care product composition comprising a personal care product and an inhibitor compound of either of the following formulae:

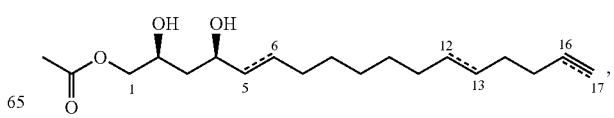

where the dashed lines are optional and represent a double bond or triple bond, and exactly one of the dashed lines is present, or

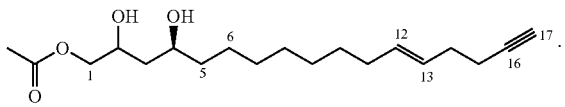 [SMILES: C#CCC/C=C/CCCCCCC[C@H](O)CC(O)COC(C)=O]

The compositions of this aspect of the invention can be formulated as described supra.

In certain embodiments, the inhibitor has the formula

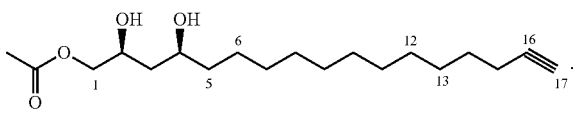

In other embodiments, the inhibitor has the formula

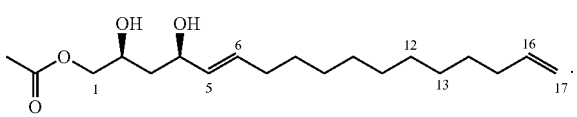 [SMILES: C=CCCCCCCCCC/C=C/[C@H](O)C[C@H](O)COC(C)=O]

A sixth aspect of the present invention relates to a cleaning product composition comprising a cleaning product and an inhibitor compound of either of the following formulae:

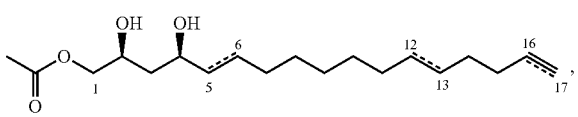

where the dashed lines are optional and represent a double bond or triple bond, and exactly one of the dashed lines is present, or

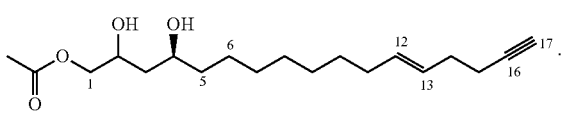 [SMILES: C#CCC/C=C/CCCCCCC[C@H](O)CC(O)COC(C)=O]

In certain embodiments, the inhibitor has the formula

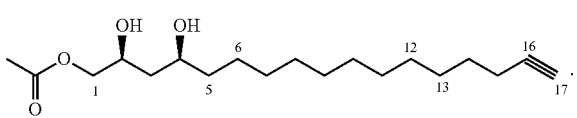

In other embodiments, the inhibitor has the formula

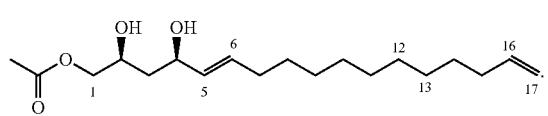 [SMILES: C=CCCCCCCCCC/C=C/[C@H](O)C[C@H](O)COC(C)=O]

The compositions of this aspect of the invention can be formulated as described supra.

EXAMPLES

The main objective of this study was to chemically characterize and determine the anti-listerial properties of an enriched acetogenin extract (EAE) from avocado seed, and its major acetogenin components, and compare it to two food grade commercial antimicrobials; an avocado seed oil enriched in acetogenins (Avosafe®) and a synthetic lipophilic product (Mirenat®), commonly used to control *Listeria*. In addition, the acetogenin composition in pulp and seeds of the commercially relevant Hass avocado cultivar was determined.

High standards regarding *L. monocytogenes* control and consumer demands for food products without synthetic additives represent a challenge to food industry. Here, the anti-listerial properties of an enriched acetogenin extract (EAE) from avocado seed were determined and compared to two commercial antimicrobials (one enriched in avocado acetogenins). Purified molecules were also tested. Acetogenin composition in pulp and seed of Hass avocado was quantified. EAE were obtained by two sequential centrifuge partition chromatography separations and molecules purified by preparative chromatography and quantified by HPLC-MS-TOF and HPLC-PDA. Avocado seed extracts, EAE and the commercially available antimicrobial Avosafe®, presented similar inhibition zones and chemical profiles. MIC values of extracts and two isolated acetogenins varied between 7.8-15.6 mg $L^{-1}$, were effective at 37 and 4° C., and showed a bactericidal effect, probably caused by increased membrane permeability and lytic effects, evidenced by flow cytometry at 10-100×MIC. Activity was comparable to Mirenat®. Most potent acetogenins were Persenone C (Compound 5 in Table 2), Persenone A (Compound 6 in Table 2), and AcO-avocadenyne (Compound 1 in Table 2), the latter exclusively present in seed. Common features of bioactive molecules were the acetyl moiety and multiple unsaturations (Compounds 2 to 3 in Table 2) in the aliphatic chain, and some persenones also featured a trans-enone group. Seeds contained 1.6 times higher levels of acetogenins than pulp (5048.1±575.5 and 3107.0±207.2 mg $kg^{-1}$ fresh weight, respectively), and total content in pulp was 199-398 times higher than MIC values. Therefore, acetogenin levels potentially consumed by humans are higher than inhibitory concentrations. Results document properties of avocado seed acetogenins as natural anti-listerial food additives.

Example 1—Chemicals

Reagent grade acetone, methanol (MetOH), ethyl acetate (EtOAc), heptane (Hept), and double distilled water ($ddH_2O$) were purchased from DEQ (San Nicolas de los Garza, NL, Mexico). HPLC grade methanol and isopropanol were supplied by Fisher Scientific (Springfield, N.J., USA) and VWR International (West Chester, Pa., USA), respectively. Standards of acetogenins were purified (>97% purity) from avocado seed and their identity confirmed by NMR and/or MS-TOF (Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30): 7403-11 (2013) and Rodríguez-Sánchez et al., "Isolation and Chemical Identification of Lipid Derivatives From Avocado (*Persea americana*) Pulp With Antiplatelet and Antithrombotic Activities," *Food Funct.* 6(1):193-203 (2015), which are hereby incorporated by reference in their entirety). Compounds included 1-acetoxy-2,4-dihydroxy-heptadec-16-yne (AcO-avocadyne, Compound 0 in Table 2), 1-acetoxy-2,4-dihydroxy-heptadec-12-en-16-yne (AcO-avocadenyne, Compound 1 in Table 2), (2S,4S)-1-acetoxy-2,4-dihydroxy-n-heptadeca-16-ene (AcO-avocadene, Compound 2 in Table 2), 1-Acetoxy-2,4-dihydroxy-heptadeca-5,16-diene (AcO-avocadiene A, Compound 3 in Table 2), (2R,5E,16E)-1-acetoxy-2-hydroxy-4-oxononadeca-5,16-diene (Persenone C, Compound 5 in Table 2); (2R,5E,12Z,15Z)-1-acetoxy-2-hydroxy-4-oxoheneicosa-5,12,15-triene (Persenone A, Compound 6 in Table 2), (2R,12Z,15Z)-1-acetoxy-2-hydroxy-4-oxoheneicosa-12,15-diene (Persin, Compound 7 in Table 2) and (5E)-1-acetoxy-2-hydroxy-4-oxononadeca-5-ene (Persenone B, Compound 8 in Table 2).

Commercial antimicrobial Mirenat® was purchased from LAMIRSA (Terrassa, Barcelona, Spain) and contained 14.5 wt % lauroyl arginate ethyl (LAE). Avosafe®, a commercial avocado seed oil enriched in acetogenins, was kindly donated by ITESM, Centro de Biotecnologia-FEMSA (Monterrey, NL, Mexico). Vehicle selection for Mirenat® and Avosafe® depended on the antimicrobial test, as described in the following sections.

Example 2—Plant Material

Avocado fruits (*Persea americana* Mill cv. var. Hass) at commercial maturity were donated by Avomex Intl. S.A. de C.V. (Sabinas, COA, Mexico). These fruits were used to prepare the acetogenin extracts from the seeds. Seeds were manually separated from the pulp, washed with water, vacuum packed, and stored at −20° C. until use. To determined acetogenin composition in pulp and seed of Hass avocados, fruits were obtained from a local market. Commercial mature fruits were selected accordingly to color and size uniformity.

Example 3—Primary Extraction

Unfrozen seeds were ground in a Torrey MJ-12 meat mincer (Monterrey, NL, Mexico). Compounds were extracted from ground seeds (6 kg) with acetone (1:2 w/v) for 24 h at room temperature. Extracts were then vacuum filtered with Whatman No. 1 paper. The filtrate was evaporated under reduced pressure in a rotatory evaporator (BUCHI Labortechnik AG, Flawil, Switzerland) at 35° C. to obtain crude extract E01. Then, E01 was partitioned in a separatory funnel with Hept:MetOH (1:1 v/v) and the upper phase (Hept) recovered and concentrated under reduced pressure to obtain extract E02.

Example 4—Fractionation of Extract E02

The previously selected Hept:MetOH 1:1 (v/v) biphasic solvent system (Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30): 7403-11 (2013), which is hereby incorporated by reference in its entirety) was used to fractionate extract E02 in a 1 L Fast centrifugal partition chromatography (CPC) system (Kromaton Technologies, Angers, ML, France) coupled to a UV detector set at 220 nm. The CPC column, spinning at 800 rpm, was entirely filled with the Hept upper phase (UP) of the solvent system and acted as the stationary phase. Then, the lower phase (LP) was pumped at a flow rate of 10 mL min$^{-1}$ to establish hydrodynamic equilibrium. Extract E02 was diluted in 50 mL of UP:LP (1:1 v/v) and injected to the FCPC column at 10 mL min$^{-1}$. LP was used to elute fractions for 170 min and, after, UP was pumped for 100 min, both at a flow rate of 10 mL min$^{-1}$ and in descending mode. A total of 270 fractions of 10 mL each were collected and their corresponding liquid-liquid distribution ratio ($K_D$) was calculated as described by Friesen et al., "Performance Characteristics of Countercurrent Separation in Analysis of Natural Products of Agricultural Significance," *J. Agric. Food Chem.* 56:19-28 (2008), which is hereby incorporated by reference in its entirety. After HPLC analysis, described in the following section, fractions exhibiting the highest acetogenin content ($K_D$=0.52-0.92) were pooled and evaporated under reduced pressure to obtain extract E03.

Example 5—Solvent Selection for Fractionation of Extract E03

Four different compositions of a Hept:EtOAc:MetOH:ddH2O solvent system were evaluated to further fractionate extract E03 (Table 1). For each system, 8 mg of E03 were dissolved in 4 mL of UP and 4 mL of LP. The systems were vortex for 1 min at 3000 rpm and, after phase separation, 1 mL aliquot of each phase was collected and the solvent evaporated. The dried sample was diluted in 1 mL isopropanol for acetogenin content determination by HPLC as described in the following section. As shown in Table 1, the biphasic system with a ratio of compound of interest (total acetogenins) in the UP to LP closer to 1, that is 9:1:9:1 (v/v/v/v) Hept:EtOAc:MetOH:ddH2O, was selected for further purification (Friesen et al., "G.U.E.S.S.—A Generally Useful Estimate of Solvent Systems for CCC," *J. Liq. Chrom. Relat. Tech.* 28:2777-806 (2005) and Friesen et al., "Performance Characteristics of Countercurrent Separation in Analysis of Natural Products of Agricultural Significance," *J. Agric. Food Chem.* 56:19-28 (2008), which are hereby incorporated by reference in their entirety).

TABLE 1

Composition and Partition Coefficient (K) of Solvent Systems Evaluated for Centrifugal Partition Chromatography (CPC) Fractionation of Extract E03.

| Solvent system | Composition (heptane:ethyl acetate:methanol:water) | Partition coefficient (K) [a] |
|---|---|---|
| 1 | 1:0:1:0 | 0.21 |
| 2 | 9:1:9:1 | 1.18 |
| 3 | 4:1:4:1 | 4.94 |
| 4 | 2:1:2:1 | 10.36 |

[a] According to Friesen et al., "G.U.E.S.S.—A Generally Useful Estimate of Solvent Systems for CCC," *J. Liq. Chrom. Relat. Tech.* 28: 2777-806 (2005) and Friesen et al., "Performance Characteristics of Countercurrent Separation in Analysis of Natural Products of Agricultural Significance," *J. Agric. Food Chem.* 56: 19-28 (2008), which are hereby incorporated by reference in their entirety, K represents the concentration ratio of compound of interest in the upper to lower phase. The solvent system with K ≈ 1 was selected for further purification by CPC fractionation.

Example 6—Fractionation of Extract

A subsequent CPC fractionation of E03 was carried out as previously described using the selected solvent system, 9:1:9:1 (v/v/v/v) Hept:EtOAc:MetOH:ddH2O. The UP, mainly Hept:EtOAc saturated with MetOH:ddH2O, served as the stationary phase. A total of 260 fractions (10 mL each) were collected, eluted with LP during 160 min and then with UP for 100 min. Fractions exclusively containing acetogenins ($K_D$=0.44-0.64) were pooled and evaporated under reduced pressure to obtain the EAE (100% w/w purity) that was used in antimicrobial assays.

Example 7—Purification of Individual Acetogenins

Acetogenins were further isolated from the EAE using a preparative Agilent 1100 HPLC system equipped with a G1315B photodiode array detector and G1364B fraction collector, as previously described by Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013), which is hereby incorporated by reference in its entirety. Detected peaks were collected independently by pooling and concentrating the corresponding fractions in a nitrogen stream. Purified compounds were stored at −20° C. until use.

Example 8—Acetogenin Composition of Avocado Pulp and Seed

As described by Rodríguez-López et al., "A Targeted Metabolomics Approach to Characterize Acetogenin Profiles in Avocado Fruit (*Persea americana* Mill)," *RSC Adv.* 5:106019-29 (2015), which is hereby incorporated by reference in its entirety, ground seed and pulp (5 g each) were homogenized independently with acetone (1:5 w/v) using an Ultra-Turrax T25 homogenizer (IKA Works, Willmington, N.C., USA) at 11000 rpm for 3 min, sonicated (5 min) and centrifuged at 3600 rpm, 5° C., for 6 min. Supernatants were collected and the precipitated material was extracted again two times, as mentioned above. Both supernatants were mixed, dried with nitrogen gas and dissolved in 3.5 mL dichloromethane with 3.5 mL deionized water. After 30 s of vortex, phases were separated by centrifugation (4000 rpm, 10 min) and the organic phase recovered, taken to dryness under nitrogen gas, resuspended in 1 mL isopropanol and passed through a 0.45 um PTFE filter prior to HPLC injection.

Example 9—Identification and Quantification of Acetogenins by HPLC

Acetogenins in samples were identified and quantified as reported by Rodríguez-López et al., "A Targeted Metabolomics Approach to Characterize Acetogenin Profiles in Avocado Fruit (*Persea americana* Mill)," *RSC Adv.* 5:106019-29 (2015), which is hereby incorporated by reference in its entirety, with some modifications. Two Agilent HPLC systems (Santa Clara, Calif., USA) were used, a 1260 Infinity series coupled to a G4212B photodiode array detector (PDA)/G4218A evaporative light scattering detector (ELSD) and a 1100 series coupled to an G1969A electrospray ionization-time-of-flight-mass spectrometry detector (ESI-TOF MS). The PDA detector was set at 220 and 208 nm, since the latter wavelength enabled Persin (Compound 7 in Table 2) identification (Rodríguez-López et al., "A Targeted Metabolomics Approach to Characterize Acetogenin Profiles in Avocado Fruit (*Persea americana* Mill)," *RSC Adv.* 5:106019-29 (2015), which is hereby incorporated by reference in its entirety). ELSD parameters were set as follows: N2 pressure=3.3 bar, temperature=40° C., gain=8 (maximum gain=12). The mobile phases consisted of water 100% (A) and methanol 100% (B), with 0.1% formic acid for LC-MS. Solvents were pumped at 1 mL min$^{-1}$ using a gradient of 0-15 min, 80-95% B; 15-25 min, 95-100% B; and 25-30 min, 100-80% B, followed by 10 min re-equilibration. Both methods were carried out in a Synergy Hydro RP $C_{18}$ column of 4.6×250 mm, 4 µm (Phenomenex, CA, USA), kept at 35° C. For quantification, calibration curves in triplicate were made for every purified compound dissolved in isopropanol. Persediene (Compound 4 in Table 2) was quantified as Persenone C (Compound 5 in Table 2) equivalents. Elucidation of chemical identity for compounds 1, 2, 4, 5, 6, 7, and 8 in Table 2 was possible by comparison of retention times and spectroscopic data to analytical standards as previously described (Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013), and Rodríguez-López et al., "A Targeted Metabolomics Approach to Characterize Acetogenin Profiles in Avocado Fruit (*Persea americana* Mill)," *RSC Adv.* 5:106019-29 (2015), which are hereby incorporated by reference in their entirety). For quantification, calibration curves in triplicate were made for every purified compound dissolved in isopropanol. Persediene (Compound 4 in Table 2) was quantified as Persenone C (Compound 5 in Table 2) equivalents.

The identity of compounds 0 and 3 in Table 2 was assigned by comparing their spectroscopic data (generated by LC-ESI-MS(/MS) with data reported by Ramos-Jerz, M. R., "Phytochemical Analysis of Avocado Seeds (*Persea americana* Mill., c.v. Hass) [PhD thesis]. Gottingen, Germany: Universitat Carolo-Wilhelmina. 311 p. Available from: Cuvillier Verlag Webshop, Gottingen, Germany, which are hereby incorporated by reference in their entirety. LC-ESI-MS(/MS) was performed using a Quattro Premier XE Micromass (Waters, Milford, Mass., USA) tandem quadrupole mass spectrometer connected to an Acquity UPLC chromatograph (Waters, Milford, Mass., USA). The chromatographic separation was achieved on a BEH C18 ACQUITY column (2.1 mm×100 mm, 1.7 µm, Waters, Milford, Mass., USA), and the column was thermostatized at 35° C. Solvent was pumped at 0.25 mL/min using a gradient of 0-5 min, 80-84% B linear; 5-10 min, 84-88% B linear; 10-10.5 min, 88-100% B linear; 10.5-12 min, 100% B isocratic, followed by 5 min of re-equilibration. The measurements were performed in the positive ion mode (ESI$^+$) controlled by the MassLynx 4.1™ software. Parameters of chromatogram and spectra acquisition were: Capillary voltage: 2.5 kV, sample cone voltage: 40 V, extraction cone voltage: 3 V, desolvation temperature: 40° C., source temperature: 120° C., cone gas ($N_2$): 50 l h$^{-}$1, desolvation gas ($N_2$): 250 l h$^{-}$1, scan range: m/z 200-800. For ESI-MS/MS (positive ion mode), sample was introduced to Quattro Premier XE Micromass (Waters, Milford, Mass., USA) tandem quadrupole mass spectrometer via a syringe pump at a flow rate of 20 µl/min, drying gas nitrogen (200 l/h at 40° C.), capillary 4 kV, cone 4V, extractor 5V, source temperature 120° C. The collision energy was set to 10 or 20 V with a spread of ±1 V and collision gas (Ar) at 1×10$^{-4}$ mbar.

Example 10—Antimicrobial Activity

*Listeria monocytogenes* (ATCC 35152) was acquired from the American Type Culture Collection (Manassas, Va., USA). For experimentation, frozen stocks were first activated in Brain Heart Infusion (BHI) broth (Becton, Dickinson and Co., Franklin Lakes, N.J., USA) for 16-18 h at 37° C. A sub-culture was prepared under the same growth conditions to ¾ log phase (6-7 h). At this stage, cells were adjusted with BHI to an initial optical density (OD) at 600 nm of 0.15, which corresponded to $8 \times 10^6$ CFU $mL^{-1}$ and served as the inoculum for the following antimicrobial assays.

Example 11—Disc Diffusion Assay

Aliquots (100 μL) of the cell suspension described above were evenly spread with a sterile plastic rod on the surface of agar plates. Sterile filter paper disks (Whatman No. 1, 6 mm) were impregnated with aliquots (5 μL) of the antimicrobial solution (EAE, Avosafe® and isolated acetogenins) freshly prepared at 3000 ppm in 96% food grade ethanol to delivered 15 μg $disc^{-1}$ of active compounds. All solutions were sonicated for 5 min (Branson 2510, Branson Ultrasonics, Danbury, Conn., USA) and vortexed for 30 s before dispensing the corresponding volumes. The disks were air-dried for approximately 1 h in a biological safety cabinet before placed into the inoculated plate. Antimicrobials were tested in triplicate, one disk per plate to account for plate variability. Vehicle and positive controls were also incorporated into each plate and contemplated 5 μl of 96% ethanol and Mirenat® at 3000 ppm LAE in sterile deionized water. Each plate contained at most six disks evenly distributed. Plates were incubated for 24 h at 37° C. After, diameters of inhibition zones were measured to the nearest millimeter.

Example 12—Minimum Inhibitory Concentration (MIC) and Minimum Bactericidal

Concentration (MBC)

Stock solutions (25000-5000 ppm) of EAE, Avosafe® and isolated molecules were prepared in ≥99.5% food-grade propylene glycol (PG) (Sigma Aldrich, St. Louis, Mo., USA) and stored in brown vials at −80° C. Working solutions in culture media were prepared from room temperature acclimatized stock solutions that were sonicated (5 min) and vortexed (30 s) as described above. Culture medium was adjusted to 4% w/v PG to account for the effect of the vehicle in all concentrations tested and sets of experiments. Prior tests were conducted to confirm that 4% PG had no effect on growth. Serial 2-fold dilutions of samples, in a range of concentrations from 125 to 0.98 ppm, were prepared in sterile 96-well clear polystyrene microplates (Cat. No. 3370, Corning, Corning, N.Y., USA) or disposable test tubes (VWR, Radnor, Pa., USA) to a final volume of 300 μL or 1 mL, respectively. The experimentation scale was determined by the amount of test product available. Each well or tube was inoculated with 10% v/v liquid phase of the cell suspension (OD600 nm 0.15) as previously described. A growth control (no antimicrobial added), an aseptic control (uninoculated), and a positive control (Mirenat®) were also examined. After 24 h at 37° C., the MIC was defined as the lowest concentration at which no visual growth was assessed by turbidity (Levison, M. E., "Pharmacodynamics of Antimicrobial Drugs," Infect. Dis. Clin. North. Am. 18(3):451-65 (2004), which is hereby incorporated by reference in its entirety). To evaluate a bactericidal effect, cultures at and above the MIC were washed two times with BHI medium by generating a cell pellet (4000 rpm, 6 min). Then, the pellet was resuspended in antimicrobial-free medium and incubated for 24 h at 37° C. The MBC was defined as the lowest concentration showing no growth (Levison, M. E., "Pharmacodynamics of Antimicrobial Drugs," Infect. Dis. Clin. North. Am. 18(3):451-65 (2004), which is hereby incorporated by reference in its entirety). All tests were independently replicated (n=3) and performed with technical triplicates.

Example 13—Lysis Assay

To determine if an enriched acetogenin extract possess a lytic effect on cells, the commercial avocado seed oil (Avosafe®) was used. Cells at late exponential phase (OD600 nm 0.8-0.9) were exposed to 10 and 100×MIC value for 24 h at 37° C. (Ling et al., "A New Antibiotic Kills Pathogens Without Detectable Resistance," Nature 517:455-59 (2015), which is hereby incorporated by reference in its entirety). After, turbidity of the cell suspension was recorded and compared to a positive and negative growth control. In addition, treated cells were evaluated by flow cytometery, as described in the following section. Mirenat® was also used as an antimicrobial control. Then, all cultures were centrifuged, washed twice and resuspended in BHI medium without antimicrobial for a second inoculation to determined bactericidal effect. Experiments were performed with technical triplicates.

Example 14—Flow Cytometery

Cell suspensions after antimicrobial exposure of lethal concentrations (10-100×MIC) were analyzed by flow cytometry (FC). Cells were first washed twice with phosphate buffer solution (PBS) by centrifugation (5000 RCF, 5 min, room temperature) and the OD600 nm adjusted to $10^6$ cell mL-1 with PBS. After, the solution was sonicated (3 s, maximum intensity) to separate groups of cells before staining. A double-stain procedure with two fluorescent nucleic acid stains was followed by adding 1 μL of a 1 mg $mL^{-1}$ propidium iodide (PI) (Cat. No. P4170, Sigma Aldrich, St. Louis, Mo., USA) solution in ddH2O and 5 μL of a 100×SYBR®Safe (SyBR-G) (Cat. No. 533102, Life Technologies, Carlsbad, Calif., USA) solution in dimethyl sulfoxide to 250 μL of cell solution (Harry et al., "Impact of Treated Sewage Effluent on the Microbiology of a Small Brook Using Flow Cytometry as a DiagnosticTool," Water Air Soil Poll 227(2):57-11 (2016), which is hereby incorporated by reference in its entirety). Then, the solution was incubated before analysis (15 min, dark, room temperature). The cytometer (BD FACSCanto II, BD, San Jose, Calif., USA) was configured with channel PerCP (670 LP nm band-pass filter) and FITC (530/30 nm band-pass filter) for PI and SyBR-G fluorescence acquisition, respectively. A total of 50000 events per sample were collected at low flow rate. Signals were collected in a logarithmic scale in forward (FSC) and side scatter (SSC), and bacteria groups (intact and membrane-damage cells) were double discriminated on their green and red fluorescence properties. SyBR-G stains both intact and membrane-damaged cells and produce green fluorescence while PI produce red fluorescence and exclusively penetrates cells with damaged membranes resulting in a distinct shift in fluorescence (Harry et al., "Impact of Treated Sewage Effluent on the Microbiology of a Small Brook Using Flow Cytometry as a DiagnosticTool," Water Air Soil Poll 227(2):57-11 (2016), which is hereby incorporated by reference in its entirety). An additional control (dead cells) was included by heating (70° C., 30 min) a portion of the growth control. Data was analyzed with FlowJo software v.8.8.6 (Tree Star, Inc., Ashland, Oreg., USA) and the experiment was independently replicated (n=3).

Example 15—Statistical Analysis

All samples were analyzed in triplicate and data expressed as the mean±standard deviation. JMP software version 5.0

(SAS Institute Inc., Cary, N.C., USA) was used for data analysis, by one-way ANOVA, and mean comparison using LSMean Student's t test (P<0.05).

Example 16—Chemical Characterization of an Enriched Acetogenin Extract (EAE)

EAE contained seven molecules of the eight acetogenins reported by Rodríguez-López et al., "A Targeted Metabolomics Approach to Characterize Acetogenin Profiles in Avocado Fruit (Persea americana Mill)," RSC Adv. 5:106019-29 (2015), which is hereby incorporated by reference in its entirety (Table 2; FIGS. 1A-1B). Mass spectra of these molecules, identified by HPLC separation coupled to ELSD (compound 0), and HPLC-PDA (compounds 1-8), displayed the ion pattern characteristic of acetogenins (Domergue et al., "Antifungal Compounds From Idioblast Cells Isolated From Avocado Fruits," Phytochemistry 54(2):183-9 (2000); Degenhardt et al., "Bitter-Tasting and Kokumi-Enhancing Molecules in Thermally Processed Avocado (Persea americana Mill.)," J. Agric. Food Chem. 58(24):12906-15 (2010); Rodríguez-Sánchez et al., "Isolation and Structure Elucidation of Avocado Seed (Persea americana) Lipid Derivatives That Inhibit Clostridium sporogenes Endospore Germination," J. Agric. Food Chem. 61(30):7403-11 (2013); and Rodríguez-López et al., "A Targeted Metabolomics Approach to Characterize Acetogenin Profiles in Avocado Fruit (Persea americana Mill)," RSC Adv. 5:106019-29 (2015), which are hereby incorporated by reference in their entirety), which consisted of a molecular ion, its corresponding sodium adduct and fragments showing losses of $H_2O$ and/or acetoxy group (losses of 18, 78, 60 mass units, respectively). Chemical identities of compounds 2, 4, 5, 6, 7, and 8 in Table 2 were assigned by comparing their retention times and mass spectra to those of previous NMR-confirmed analytical standards (Rodríguez-Sánchez et al., "Isolation and Structure Elucidation of Avocado Seed (Persea americana) Lipid Derivatives That Inhibit Clostridium sporogenes Endospore Germination," J. Agric. Food Chem. 61(30):7403-11 (2013), which is hereby incorporated by reference in its entirety). Compounds were identified as: AcO-avocadene (Compound 2 in Table 2), persediene (Compound 4 in Table 2), Persenone C (Compound 5 in Table 2), Persenone A (Compound 6 in Table 2), Persin (Compound 7 in Table 2) and Persenone B (Compound 8 in Table 2). In addition, using similar chromatographic conditions, Compound 1 in Table 2 was detected and tentatively identified by Rodríguez-López et al., "A Targeted Metabolomics Approach to Characterize Acetogenin Profiles in Avocado Fruit (Persea americana Mill)," RSC Adv. 5:106019-29 (2015), which is hereby incorporated by reference in its entirety as 1-acetoxy-2,4-dihydroxy-heptadec-12-en-16-yne (AcO-avocadenyne, Compound 1 in Table 2) based on the ion pattern reported by Ramos-Jerz, M. R., "Phytochemical Analysis of Avocado Seeds (Persea americana Mill., c.v. Hass) [PhD thesis]. Gottingen, Germany: Universitat Carolo-Wilhelmina. 311 p. Available from: Cuvillier Verlag Webshop, Gottingen, Germany, which is hereby incorporated by reference in its entirety.

TABLE 2

Chemical Structure of Acetogenins from Avocado Extracts.

| Compound (number)[a] | [M + H]+/ Ions Pattern (m/z)[b] | Molecular formula | Structure | References[c] |
|---|---|---|---|---|
| AcO-avocadyne (0) | 327/349, 309, 267, 249, 231 | $C_{19}H_{32}O_4$ | | (Ramos-Jerz 2007; Domergue et al. 2000) |
| AcO-avocadenyne (1) | 325/347, 307, 265 | $C_{19}H_{32}O_4$ | 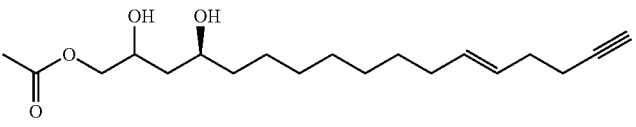 [SMILES: C#CCC/C=C/CCCCCCC[C@H](O)CC(O)COC(C)=O] | (Ramos-Jerz 2007; Rodríguez-López et al. 2015) |
| AcO-avocadene (2) | 329/351, 311, 269, 251 | $C_{19}H_{36}O_4$ | 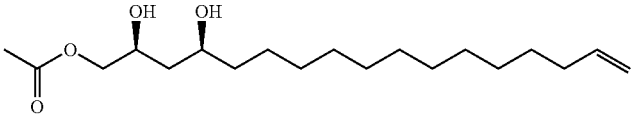 [SMILES: C=CCCCCCCCCCCC[C@H](O)C[C@H](O)COC(C)=O] | (Domergue et al. 2000) |
| AcO-avocadiene A (3) | 327/349, 309, 267, 249, 231 | $C_{19}H_{34}O_4$ | | (Ramos-Jerz 2007; Rodríguez-López et al. 2015) |
| Persediene (4) | 353/375, 335, 293 | $C_{21}H_{36}O_4$ | 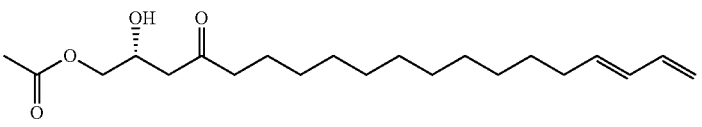 [SMILES: C=C/C=C/CCCCCCCCCCCC(=O)C[C@@H](O)COC(C)=O] | (Rodríguez-Sánchez et al. 2013a) |

TABLE 2-continued

Chemical Structure of Acetogenins from Avocado Extracts.

| Compound (number)[a] | [M + H]+/ Ions Pattern (m/z)[b] | Molecular formula | Structure | References[c] |
|---|---|---|---|---|
| Persenone C (5) | 353/375, 335, 293 | $C_{21}H_{36}O_4$ | 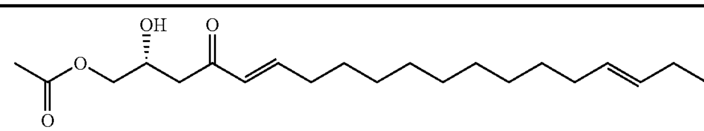 | (Rodríguez-Sánchez et al. 2013a) |
| Persenone A (6) | 379/401, 361, 319, 301 | $C_{23}H_{38}O_4$ | 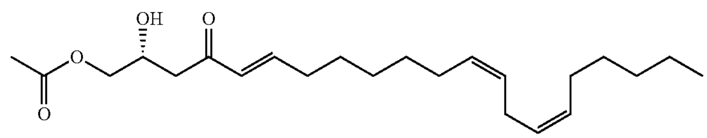 [SMILES: CCCCC/C=C\C/C=C\CCCCC/C=C/C(=O)C[C@@H](O)COC(C)=O] | (Domergue et al. 2000) |
| Persin (7) | 381/403, 363, 321, 303 | $C_{23}H_{40}O_4$ | 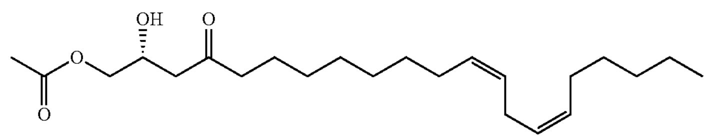 [SMILES: CCCCC/C=C\C/C=C\CCCCCCCC(=O)C[C@@H](O)COC(C)=O] | (Kawagishi et al. 2001) |
| Persenone B (8) | 355/377, 337, 295 | $C_{21}H_{38}O_4$ | 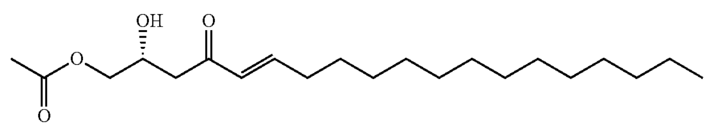 [SMILES: CCCCCCCCCCCCC/C=C/C(=O)C[C@@H](O)COC(C)=O] | (Kim et al. 2000) |

[a]Compound numbers from 0 to 8 were assigned according to order of elution from the HPLC column as shown in FIGs 1A-1B.
[b]Time of Flight Mass Spectrometry MS/TOF detection using electrospray ionization interface in positive-ion mode of analysis.
[c]Ramos-Jerz, M. R., "Phytochemical Analysis of Avocado Seeds (*Persea americana* Mill., c.v. Hass) [PhD thesis]. Gottingen, Germany: Universitat Carolo-Wilhelmina. 311 p. Available from: Cuvillier Verlag Webshop, Gottingen, Germany; Rodríguez-López et al., "A Targeted Metabolomics Approach to Characterize Acetogenin Profiles in Avocado Fruit (*Persea americana* Mill.)," *RSC Adv.* 5: 106019-29 (2015); Domergue et al., "Antifungal Compounds From Idioblast Cells Isolated From Avocado Fruits," *Phytochemistry* 54(2): 183-9 (2000); Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30): 7403-11 (2013); Kawagishi et al., "Liver Injury Suppressing Compounds From Avocado (*Persea americana*)." *J. Agric. Food Chem.* 49(5): 2215-21 (2001); and Kim et al. "Novel Nitric Oxide and Superoxide Generation Inhibitors, Persenone A and B, from Avocado Fruit," *J. Agric. Food Chem.* 48(5): 1557-63 (2000), which are hereby incorporated by reference in their entirety.

Example 17—Antimicrobial Activity of Extracts

Figure 2:
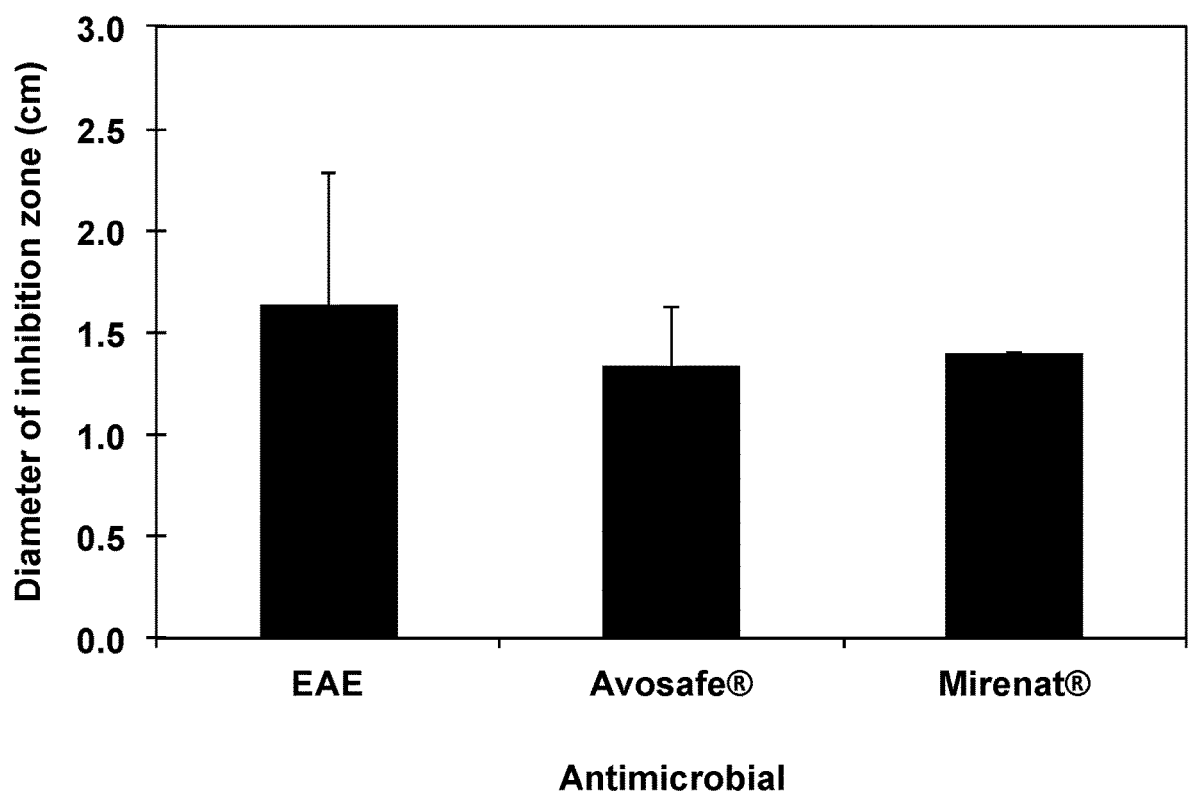
FIG. 2 shows the diameter of inhibition zones of an enriched acetogenin extract (EAE) from avocado seed, Avosafe® (commercial avocado seed oil enriched in acetogenins) and Mirenat® (commercial antimicrobial) against *Listeria monocytogenes* (37° C., 24 h). Values represent mean±standard deviation of technical replicates (n=3). Data was duplicated. EAE and Avosafe® were tested at 15 μg disc$^{-1}$ total acetogenins and Mirenat® at 15 μg disc$^{-1}$ of lauroyl arginate ethyl (LAE). No significant differences among data (LSMeans Student's t, P=0.867, n=9).

EAE showed antimicrobial activity against *L. monocytogenes* similar to that of commercial antimicrobials, Avosafe® and Mirenat® (FIG. 2). Inhibition zones observed in the disk diffusion assay were not significantly different (ANOVA, P=0.8682, n=9) among commercial antimicrobials tested (1.6±0.7 cm for EAE compared to 1.3±0.3 and 1.4±0.0 cm for Avosafe® and Mirenat®, respectively). As expected, Avosafe® activity was comparable to EAE, as both are concentrated oil extracts from avocado seed.

Example 18—Relative Acetogenin Concentrations in Extracts

Figures 3A, 3B:
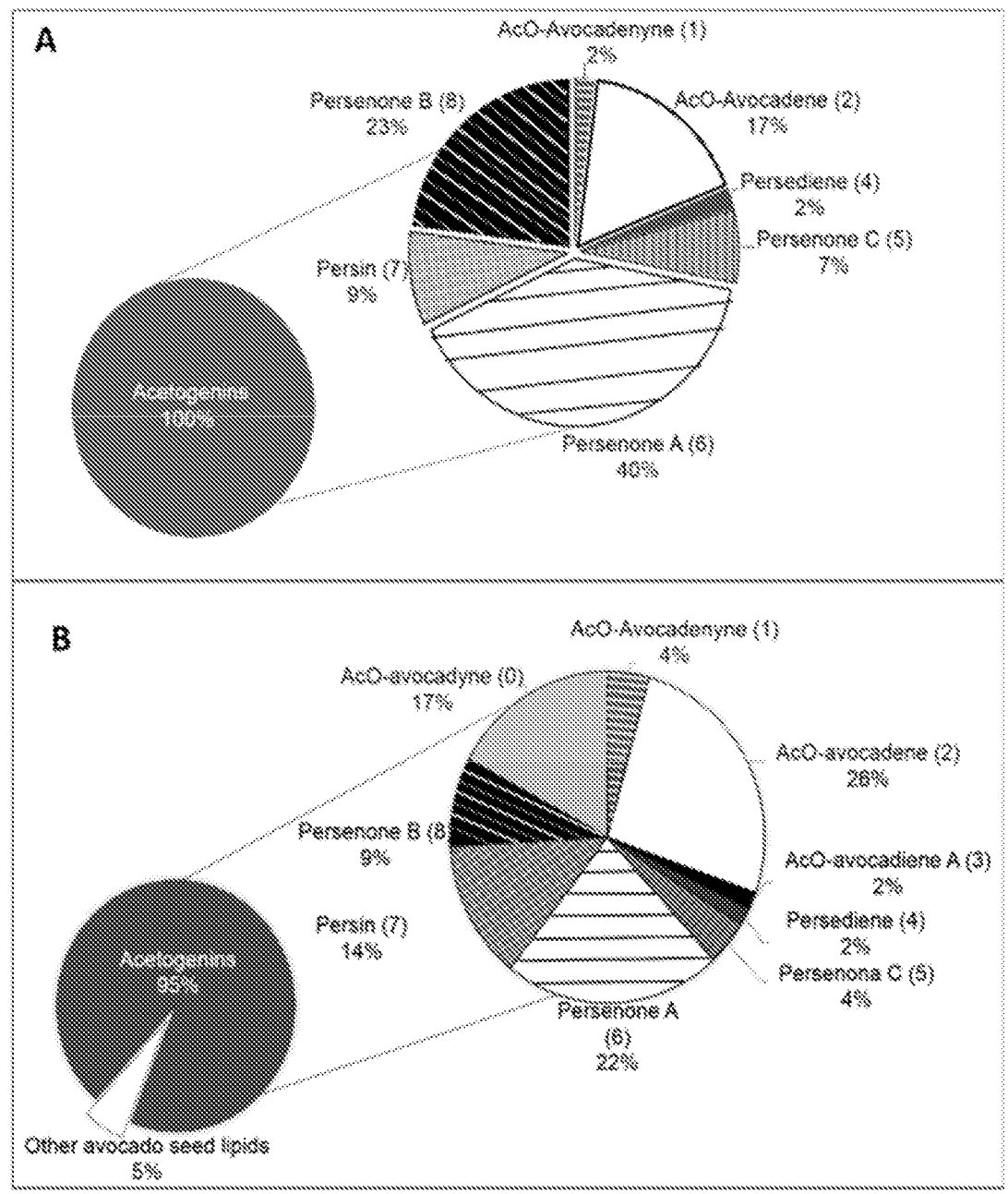
FIGS. 3A-3B show relative concentration of individual acetogenins in an enriched acetogenin extract (EAE) from avocado seed (FIG. 3A), obtained by centrifugal partition chromatography, and Avosafe® (FIG. 3B), a commercial avocado seed oil enriched in acetogenins.
Figures 10A, 10B:
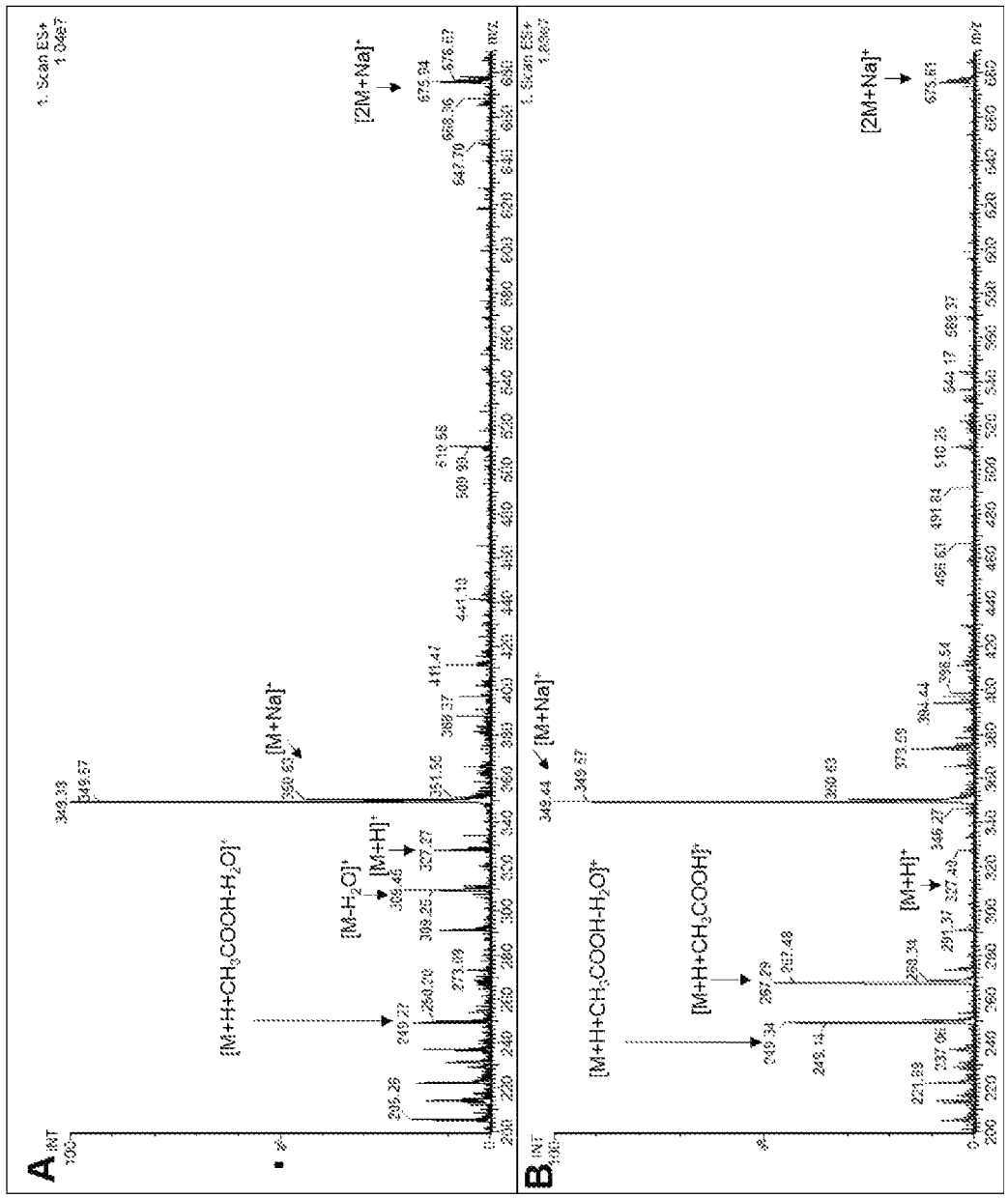
FIGS. 10A-10B show LC-ESI-MS/MS spectra of AcO-avocadyne (Compound 0, FIG. 10A) and compound AcO-avocadiene A (Compound 3, FIG. 10B). LC-ESI-MS/MS was performed using a Quattro Premier XE Micromass (Waters, Inc.) tandem quadrupole mass spectrometer connected to a Acquity UPLC chromatograph (Waters, Milford, Mass., USA). Separation took place in a BEH C18 ACQUITY column (2.1 mm×100 mm, 1.7 μm, Waters), and the column was thermostatized at 35° C. Solvent was pumped at 0.25 mL/min using a gradient of 0-5 min, 80-84% B linear; 5-10 min, 84-88% B linear; 10-10.5 min, 88-100% B linear; 10.5-12 min, 100% B isocratic, followed by 5 min of re-equilibration.
Figures 11A, 11B, 11C:
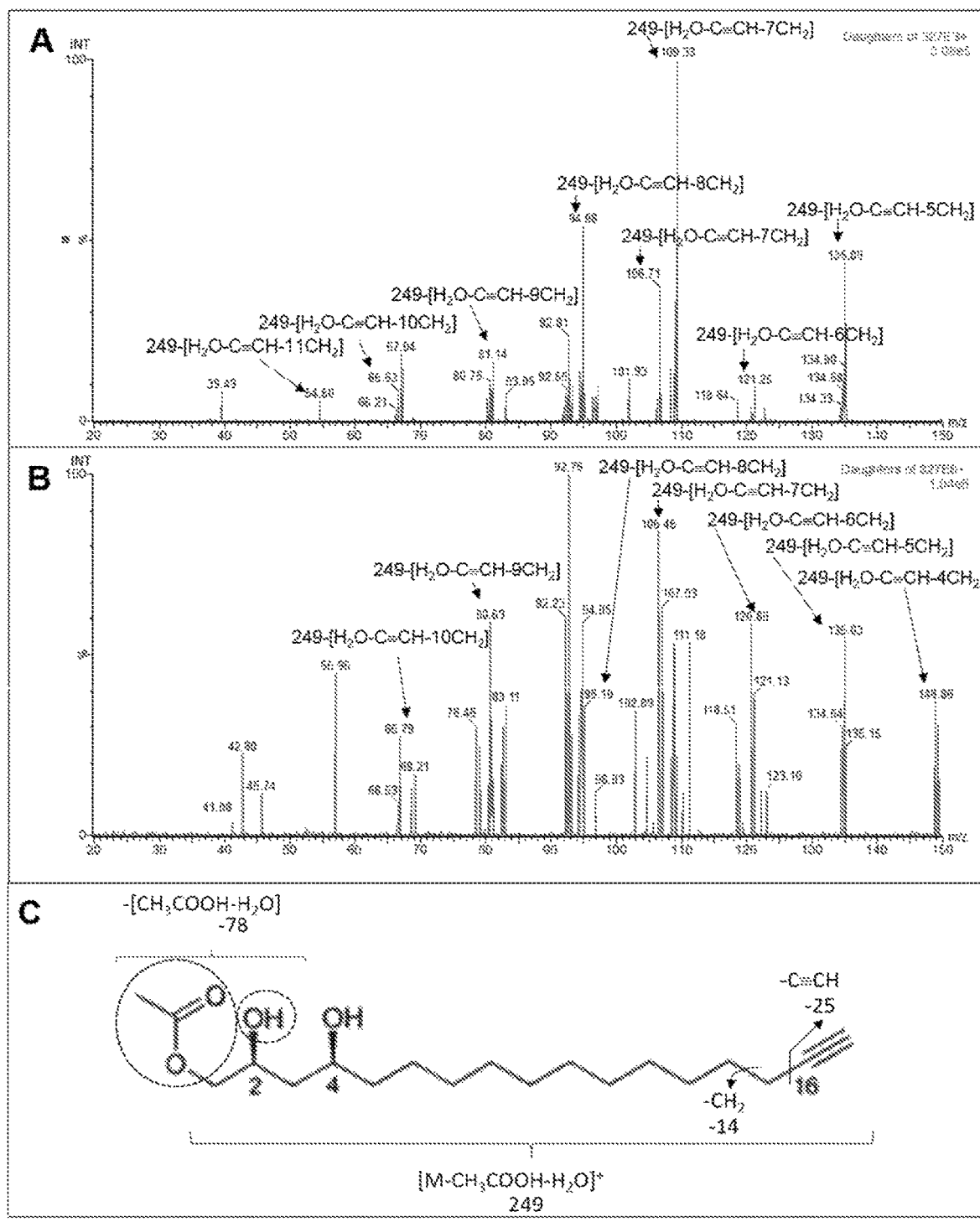
FIGS. 11A-11C show ESI-MS/MS spectra of AcO-avocadyne (Compound 0, total ion at 327 and a daughter ion at 249 m/z) at 10 eV (FIG. 11A) and 20 eV (FIG. 11B), and its characteristic fragmentation pattern (FIG. 11C). ESI-MS/MS was performed using a Quattro Premier XE Micromass (Waters, Inc.) tandem quadrupole mass spectrometer. Sample was introduced via a syringe pump at a flow rate of 20 μl/min, drying gas nitrogen (200 l/h at 40° C.). ESI-MS/MS (positive ion mode): capillary 4000 V, cone 4V, extractor 5V, source temperature 120° C. The collision energy was set to 10 or 20 V with a spread of ±1 V.
Figures 12A, 12B, 12C:
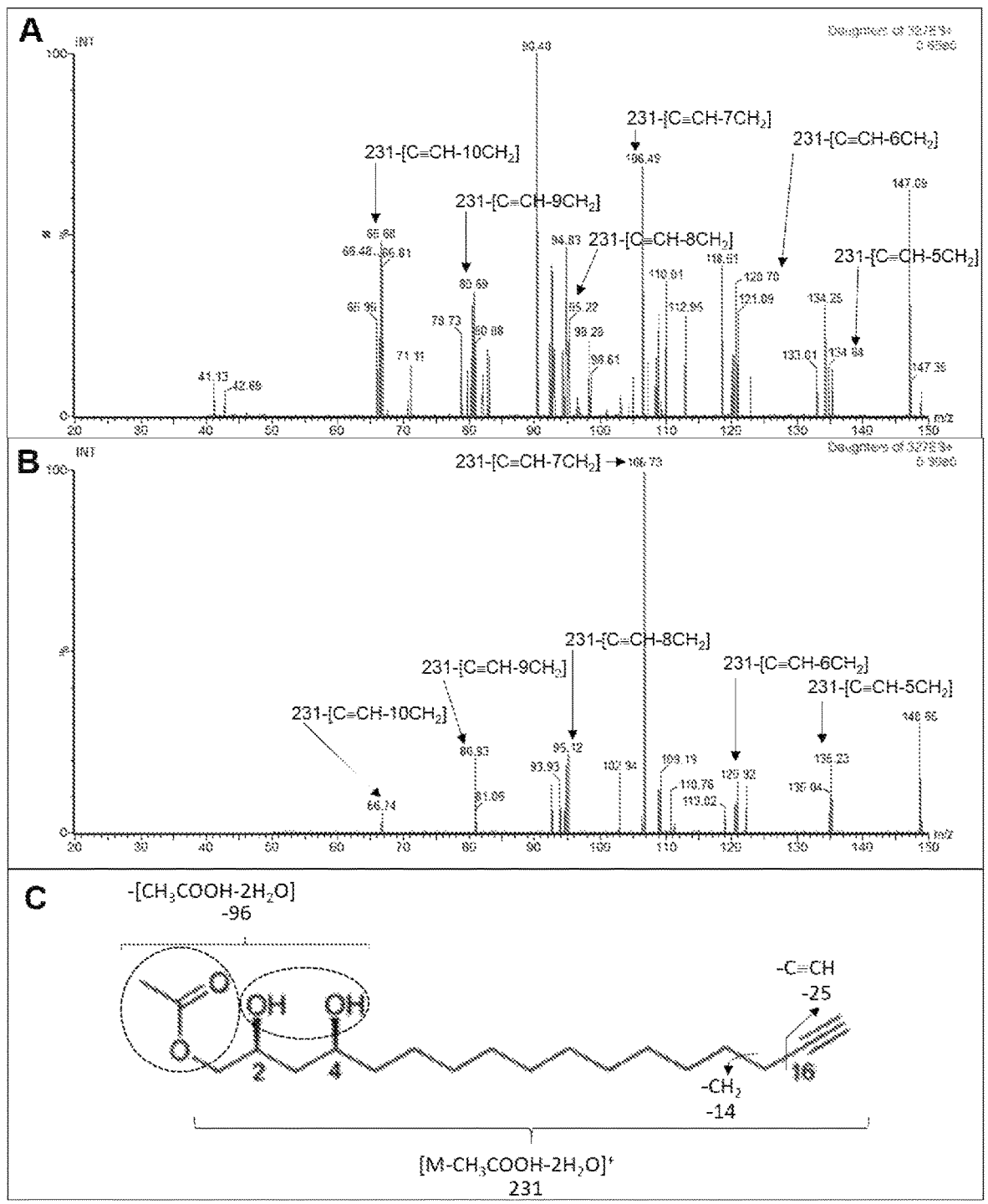
FIGS. 12A-12C show ESI-MS/MS spectra of AcO-avocadyne (Compound 0, total ion at 327 and a daughter ion at 231 m/z) at 10 eV (FIG. 12A) and 20 eV (FIG. 12B), and its characteristic fragmentation pattern (FIG. 12C). ESI-MS/MS was performed using a Quattro Premier XE Micromass (Waters, Inc.) tandem quadrupole mass spectrometer. Sample was introduced via a syringe pump at a flow rate of 20 μl/min, drying gas nitrogen (200 l/h at 40° C.). ESI-MS/MS (positive ion mode): capillary 4000 V, cone 4V, extractor 5V, source temperature 120° C. The collision energy was set to 10 or 20 V with a spread of ±1 V.
Figures 13A, 13B, 13C:
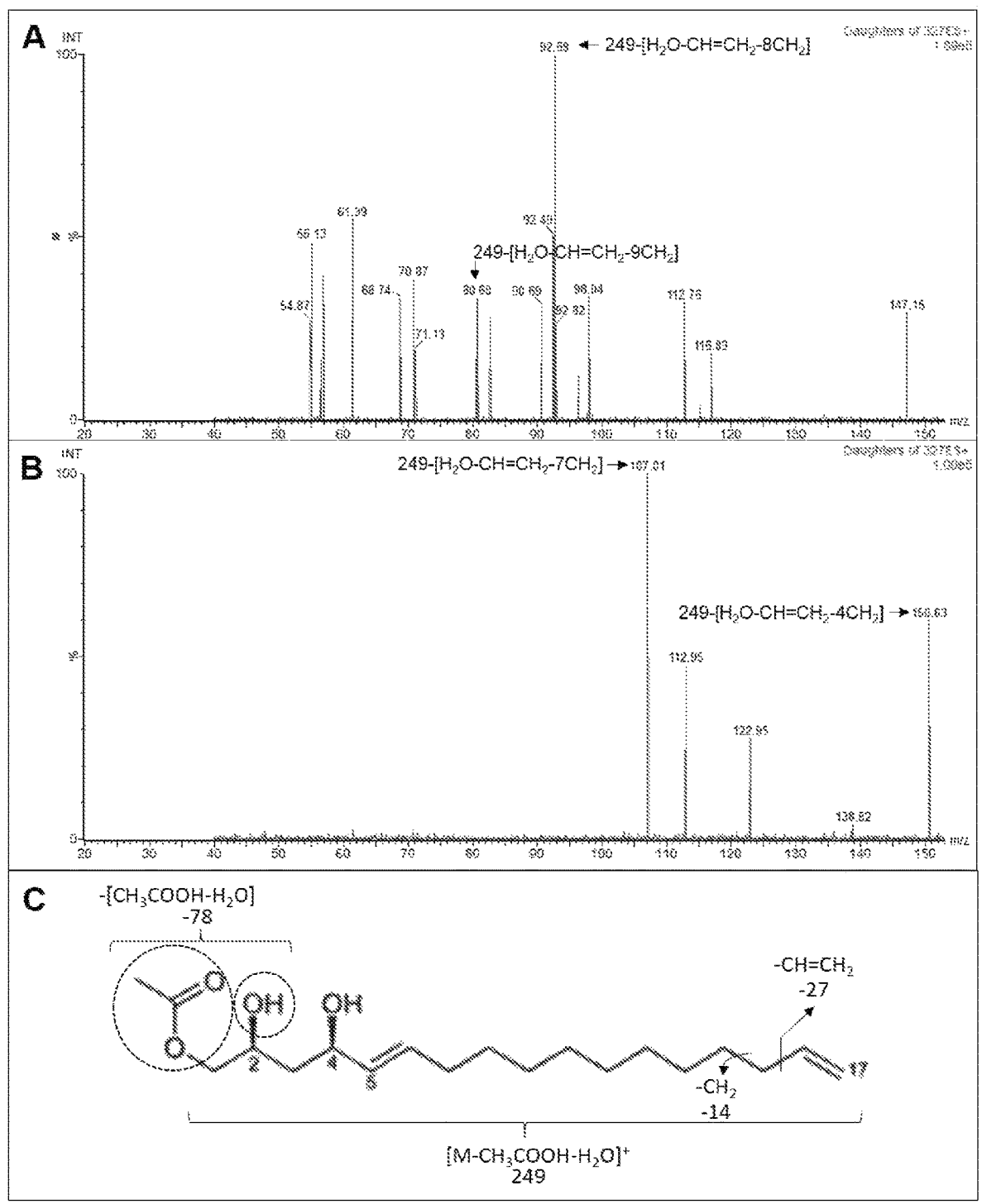
FIGS. 13A-13C show ESI-MS/MS spectra of AcO-avocadiene A (Compound 3, total ion at 327 and a daughter ion at 249 m/z) at 10 eV (FIG. 13A) and 20 eV (FIG. 13B), and its characteristic fragmentation pattern (13C). ESI-MS/MS was performed using a Quattro Premier XE Micromass (Waters, Inc.) tandem quadrupole mass spectrometer. Sample was introduced via a syringe pump at a flow rate of 20 μl/min, drying gas nitrogen (200 l/h at 40° C.). ESI-MS/MS (positive ion mode): capillary 4000 V, cone 4V, extractor 5V, source temperature 120° C. The collision energy was set to 10 or 20 V with a spread of ±1 V.
Figures 14A, 14B, 14C:
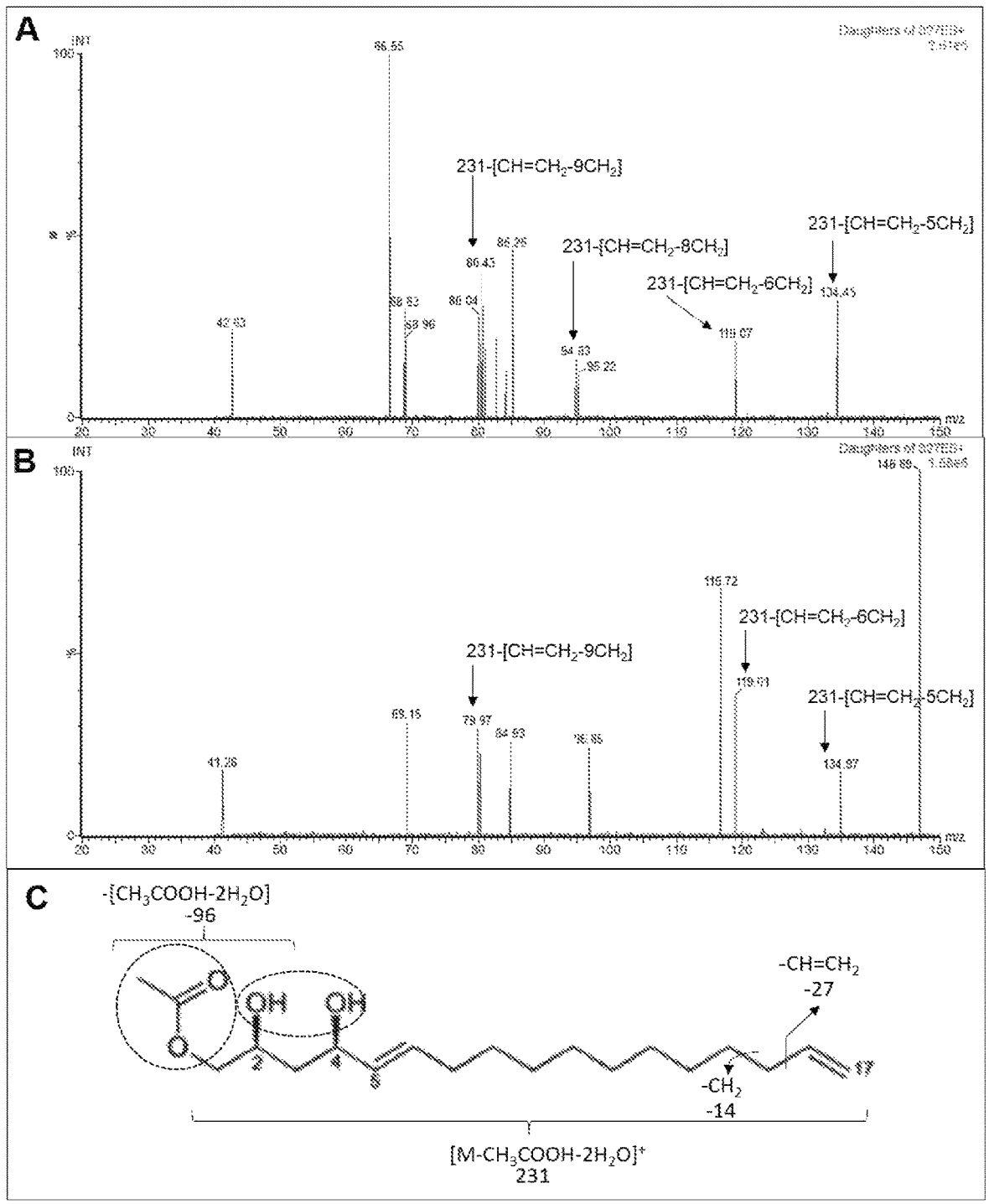
FIGS. 14A-14C show ESI-MS/MS spectra of AcO-avocadiene A (Compound 3, total ion at 327 and a daughter ion at 231 m/z) at 10 eV (FIG. 14A) and 20 eV (FIG. 14B), and its characteristic fragmentation pattern (FIG. 14C). ESI-MS/MS was performed using a Quattro Premier XE Micromass (Waters, Inc.) tandem quadrupole mass spectrometer. Sample was introduced via a syringe pump at a flow rate of 20 μl/min, drying gas nitrogen (200 l/h at 40° C.). ESI-MS/MS (positive ion mode): capillary 4000 V, cone 4V, extractor 5V, source temperature 120° C. The collision energy was set to 10 or 20 V with a spread of ±1 V.

Avocado seed extracts (EAE and Avosafe®) possessed similar acetogenin profiles, except for the presence of Compound 0 and 3 in Table 2, respectively) and other lipids in Avosafe® (FIGS. 3A-3B). Mass spectra of these two molecules (FIGS. 10A-10B), generated by LC-ESI-MS, displayed the characteristic ion pattern of acetogenins, both consisting of a molecular ion ([M+H]+=327), its corresponding sodium adduct ([M+Na]+=349), a dimer with sodium adduct ([2M+Na]+=675), and fragments showing losses of water ([M−H$_2$O]+=309) and/or acetoxy group ([M+CH$_3$COOH−H$_2$O]+=249/[M+H+CH$_3$COOH]+=267), that represented losses of 18, 78, 60 mass units from the molecular ion, respectively. This fragmentation pattern corresponded to three reported acetogenins by Ramos-Jerz, M. R., "Phytochemical Analysis of Avocado Seeds (*Persea americana* Mill., c.v. Hass) [PhD thesis]. Gottingen, Germany: Universitat Carolo-Wilhelmina. 311 p. Available from: Cuvillier Verlag Webshop, Gottingen, Germany, which is hereby incorporated by reference in its entirety, that only differ in the position of the unsaturated bonds. However, collision-induced dissociation (CID), through ESI-MS/MS (FIGS. 11A-11C, 12A-12C, 13A-13C, and 14A-14C) produced more fragmentation of the precursor (total ion at 327) and daughter ions ([M+H+CH$_3$COOH−H$_2$O]+=249 and [M+H+CH$_3$COOH−2H$_2$O]+=231 m/z), that provided additional structural information for the identification. CID (10 and 20 eV) of Compound 0 showed fragments that corresponded to the loss of a terminal triple bond (25 units), water (18 units, only in the case of daughter ion 249) and multiple losses (from 4 up to 11, at 20 eV) of CH$_2$ groups (14 units, each group), as shown in FIGS. 11A-11C and 12A-12C. From this pattern it was possible to determine that the structure of Compound 0 corresponds to 1-Acetoxy-2,4-dihydroxy-heptadec-16-yne (Table 2), compound previously reported by Ramos-Jerz, M. R., "Phytochemical Analysis of Avocado Seeds (*Persea americana* Mill., c.v. Hass) [PhD thesis]. Gottingen, Germany: Universitat Carolo-Wilhelmina. 311 p. Available from: Cuvillier Verlag Webshop, Gottingen, Germany, which is hereby incorporated by reference in its entirety; since it presents a terminal double bond (C16-C17), and therefore and aliphatic chain of C11 (from C-5 to C-15). While CID (10 and 20 eV) of Compound 3 showed fragments that corresponded to the loss of a terminal double bond (27 units), water (18 units, only in the case of daughter ion 249) and multiple losses (from 4 up to 9, at 20 eV) of $CH_2$ groups (14 units, each group), as shown in FIGS. 13A-13C and 14A-14C. From this pattern it was possible to determine that the structure of Compound 3 corresponds to 1-Acetoxy-2,4-dihydroxy-heptadeca-5,16-diene (Table 2), previously reported by Ramos-Jerz, M. R., "Phytochemical Analysis of Avocado Seeds (*Persea americana* Mill., c.v. Hass) [PhD thesis]. Gottingen, Germany: Universitat Carolo-Wilhelmina. 311 p. Available from: Cuvillier Verlag Webshop, Gottingen, Germany, which is hereby incorporated by reference in its entirety; since it presents a terminal double bond (C16-C17) and a C5-C6 double, and therefore and aliphatic chain of C9 (from C-7 to C-15). Persenone A (Compound 6 in Table 2), Persenone B (Compound 8 in Table 2) and AcO-avocadene (Compound 2 in Table 2) were the three major components in EAE, accounting for 40, 23 and 17% w/w, respectively. Whereas in Avosafe®, AcO-avocadene (Compound 2 in Table 2), Persenone A (Compound 6 in Table 2) and AcO-Avocadyne (Compound 0 in Table 2) were the main acetogenins present at 26, 22 and 17% w/w, respectively.

Figure 4:
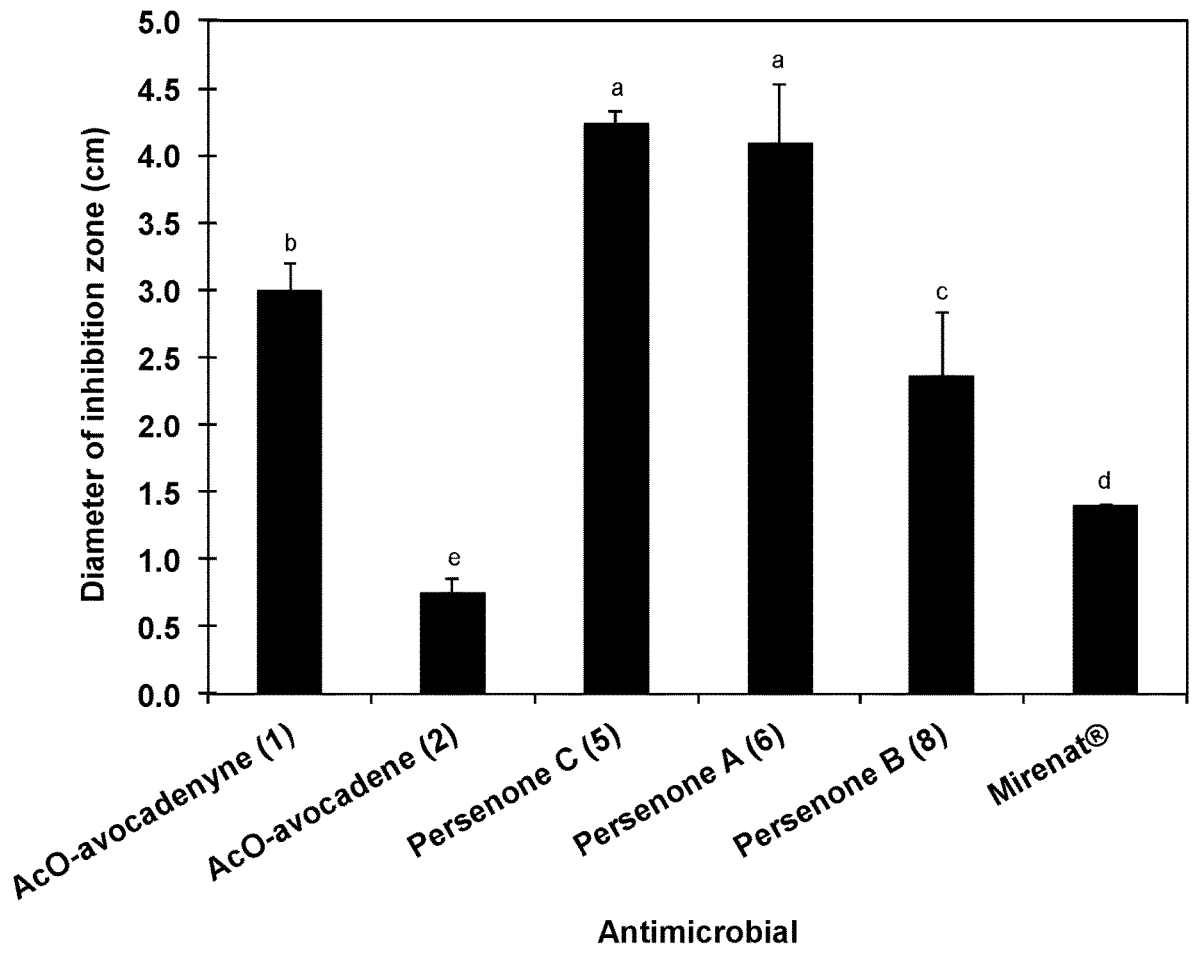
FIG. 4 shows the diameter of inhibition zones of isolated acetogenins from avocado seed against *Listeria monocytogenes* (37° C., 24 h). Values represent mean±standard deviation of technical replicates (n=3). Data was duplicated. Mirenat®: commercial antimicrobial. Isolated molecules were tested at 15 μg disc$^{-1}$ and Mirenat® at 15 μg disc$^{-1}$ of lauroyl arginate ethyl (LAE). Different letters indicate significant differences (LSMeans Student's t, alpha=0.05, n=14-16). AcO-avocadyne (Compound 0 in Table 2) and AcO-avocadiene A (Compound 3 in Table 2) were also evaluated but they did not produce inhibition zones.

Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013), which is hereby incorporated by reference in its entirety, reported that the most potent acetogenins against *Clostridium sporogenes* were (in descending order) Persenone C (Compound 8 in Table 2), Persenone B (Compound 6 in Table 2) and Persenone A (Compound 5 in Table 2), which structurally shared an acetyl moiety and trans-enone group as shown in Table 2. These molecules were 1.2, 2.1 and 1.4 times more concentrated in EAE than Avosafe®, respectively (FIGS. 3A-3B). Despite these differences, both avocado seed extracts showed similar antimicrobial activity (FIG. 2). Thus, other molecules might be responsible for the observed anti-listerial activity; however, Persenone A (Compound 6 in Table 2) and B (Compound 8 in Table 2) were major components in both extracts (FIGS. 3A-3B). Also, interactions between molecules (synergism or antagonism) in extracts could contribute directly or indirectly to the observed bioactivity or effects of chemical compatibility between molecules and the culture medium might constrain molecule diffusion throughout the agar. To precisely assess each compound contribution, molecules need to be isolated from the extracts.

Example 19—Anti-Listerial Activity of Isolated Acetogenins

Major acetogenins in EAE were isolated by means of preparative HPLC (>97% purity). As shown in FIG. 4, in an equal weight basis (15 μg $disc^{-1}$), Persenone C (Compound 5 in Table 2) and A (Compound 6 in Table 2) exhibited the highest inhibition zones against *L. monocytogenes*, followed by AcO-avocadenyne (Compound 1 in Table 2) and Persenone B (Compound 8 in Table 2). Of the isolated acetogenins, AcO-avocadene (Compound 2 in Table 2) was the least potent with an activity significantly lower than Mirenat®, which was tested at 15 μg $disc^{-1}$ of LAE (active ingredient). Remarkably, Persenone C (Compound 5 in Table 2) and A (Compound 6 in Table 2) were both around 3-fold more potent than Mirenat®.

These results confirmed that some acetogenins previously tested against different bacterial species (Neeman et al., "New Antibacterial Agent Isolated From the Avocado Pear," *Appl. Microbiol.* 19:470-73 (1970); Domergue et al., "Antifungal Compounds From Idioblast Cells Isolated From Avocado Fruits," *Phytochemistry* 54(2):183-9 (2000); Dharmaratne et al., "Antimicrobial and Antileishmanial Active Acetogenins From Avacado (*Persea americana*) Fruits," *Planta Med.* 78:34 (2012); Lu et al., "Secondary Metabolites From the Unripe Pulp of *Persea americana* and Their Antimycobacterial Activities," *Food Chem.* 135:2904-09 (2012); and Rodríguez-Sánchez et al., "Isolation and Chemical Identification of Lipid Derivatives From Avocado (*Persea americana*) Pulp With Antiplatelet and Antithrombotic Activities," *Food Funct.* 6(1):193-203 (2015), which are hereby incorporated by reference in their entirety), also possess anti-listerial activity. In particular, some persenones and AcO-avocadenyne (Compound 1 in Table 2). Though, this is the first report of AcO-avocadenyne (Compound 1 in Table 2) antimicrobial activity. Furthermore, Raymond-Chia et al., "Antimicrobial Activity of Crude Epicarp and Seed Extracts From Mature Avocado Fruit (*Persea americana*) of Three Cultivars," *Pharm. Biol.* 48:753-756 (2010), which is hereby incorporated by reference in its entirety, compared water and ethanolic extracts of mature avocado fruits against *L. monocytogenes* and found that water extracts showed higher antimicrobial potential (94 to 375 and 125 to >500 mg $L^{-1}$ MIC, respectively), contrary to other results. However, it is unlikely that compounds responsible in the water extracts were acetogenins as these are lipophilic molecules nearly insoluble in water (Champy et al., "Quantification of Acetogenins in Annona Muricata Linked to Atypical Parkinsonism in Guadeloupe," *Mov. Disord.* 20(12):1629-33 (2005), and Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013), which are hereby incorporated by reference in their entirety).

Interestingly, most potent molecules (Persenone C (Compound 5 in Table 2) and A (Compound 6 in Table 2), and AcO-avocadenyne (Compound 1 in Table 2)) against *L. monocytogenes* showed multiple unsaturations in the aliphatic chain. Similarly, Lu et al., "Secondary Metabolites From the Unripe Pulp of *Persea americana* and Their Antimycobacterial Activities," *Food Chem.* 135:2904-09 (2012), which is hereby incorporated by reference in its entirety, based on the antimycobacterial activity of acetogenins and fatty alcohol derivatives from avocado pulp concluded that molecules with two unsaturations were more potent than saturated or monounsaturated compounds. Nevertheless, these authors, as well as Neeman et al., "New Antibacterial Agent Isolated From the Avocado Pear," *Appl. Microbiol.* 19:470-73 (1970), which is hereby incorporated by reference in its entirety, described that a triol moiety (OH groups at C-1, C-2 and C-4) increased antibacterial properties when compared to partially or totally acetylated compounds. The acetogenins evaluated in this study, do not present a triol moiety but possess an OH group at C-2 and an acetoxy group at C-1 (Table 2). In addition, AcO-avocadyne (Compound 0 in Table 2) AcO-avocadenyne (Compound 1 in Table 2), AcO-avocadene (Compound 2 in Table 2) and AcO-avocadiene A (Compound 3 in Table 2) exhibit another OH group at C-4 and all other molecules a keto group. The fact that the activity of AcO-avocadenyne (Compound 1 in Table 2) greatly differs from AcO-avocadene (Compound 2 in Table 2), while AcO-avocadyne (Compound 0 in Table 2) and AcO-avocadiene A (Compound 3 in Table 2) did not produce inhibition zones, even when they all share the same C-1, C-2 and C-4 groups, seems to indicate that the number of unsaturations and the terminal bond configuration (methylene or acetylene) in the aliphatic chain are important structural feature that determine anti-listerial activity. In agreement with prior reports, it has been observed that antibacterial activity of fatty acids, structurally similar to acetogenins (Rodriguez-Saona et al., "Isolation, Identification, and Biological Activity of Isopersin, a New Compound From Avocado Idioblast Oil Cells," *J. Nat. Prod.* 61:1168-70 (1998), which is hereby incorporated by reference in its entirety), increased in parallel with number of unsaturations (Knapp et al., "Bactericidal Effects of Polyunsaturated Fatty Acids," *J. Infect. Dis.* 154(1):84-94 (1986) and Carballeira, N. M., "New Advances in Fatty Acids as Antimalarial, Antimycobacterial and Antifungal Agents," *Prog. Lipid Res.* 47(1):50-61 (2008), which are hereby incorporated by reference in their entirety). Also, that a terminal methylene confers greater potency to avocado lipid derivatives than a terminal acetylene group (Neeman et al., "New Antibacterial Agent Isolated From the Avocado Pear," *Appl. Microbiol.* 19:470-73 (1970) and Lu et al., "Secondary Metabolites From the Unripe Pulp of *Persea americana* and Their Antimycobacterial Activities," *Food Chem.* 135:2904-09 (2012), which are hereby incorporated by reference in their entirety). Surprisingly, in this study the opposite seems to occur as AcO-avocadenyne (Compound 1 in Table 2), which possesses a terminal acetylene (Table 2), showed 4-times greater antimicrobial activity than AcO-avocadene (Compound 2 in Table 2), with a terminal methylene (FIG. 4). The trans-enone group, featured by the most potent anti-listerial acetogenins (Persenone C (Compound 5 in Table 2) and A (Compound 6 in Table 2)), continues to be the preferable structural feature as previously reported against *C. sporogenes* (Rodríguez-Sánchez et al., "Isolation and Structure Elucidation of Avocado Seed (*Persea americana*) Lipid Derivatives That Inhibit *Clostridium sporogenes* Endospore Germination," *J. Agric. Food Chem.* 61(30):7403-11 (2013), which is hereby incorporated by reference in its entirety). However, Persenone B (Compound 8 in Table 2) that possess the trans-enone group, exhibited lower anti-listerial properties, possibly because it lacks multiple unsaturations in the aliphatic chain.

Considering structural similarities between acetogenins aliphatic chains and fatty acids, an analogous mechanism of action could be hypothesized. Fatty acids are known to naturally insert into cell membranes and physically disturb their functionality (Greenway et al., "Mechanism of the Inhibitory Action of Linoleic Acid on the Growth of *Staphylococcus aureus*," *J. Gen. Microbiol.* 115(1):233-45 (1979) and Pohl et al., "Antifungal Free Fatty Acids: A Review," in Mendez, ed. *Science Against Microbial Pathogens: Communicating Current Research and Technological Advances*, Spain: Formatex Research Center, pp: 61-71 (2011), which are hereby incorporated by reference in their entirety). Moreover, cis-double bonds present in unsaturated fatty acids can form fixed bends in their carbon chain that occupy a greater cross-section and introduce disorder into neighbor phospholipid acyl chains, which leads to higher membrane fluidity, generalized disorganization, and eventually cell disintegration (Avis et al., "Specificity and Mode of Action of the Antifungal Fatty Acid Cis-9-Heptadecenoic Acid Produced by *Pseudozyma flocculosa*," *Appl. Environ. Microbiol.* 67(2):956-60 (2001) and Avis, T. J., "Antifungal Compounds That Target Fungal Membranes: Applications in Plant Disease Control," *Can. J. Plant Pathol.* 29(4):323-29 (2007), which are hereby incorporated by reference in their entirety). This structure is present at position C-12 and C-15 in Persenone A (Compound 6 in Table 2), one of the most active molecules against *L. monocytogenes*, and Persin (Compound 7 in Table 2), not evaluated in this study (Table 2). In addition, polyunsaturated lipids are associated with an increase in oxidative stress of cell membranes through autoxidation and, peroxide and radical formation that inhibits cell growth (Knapp et al., "Bactericidal Effects of Polyunsaturated Fatty Acids," *J. Infect. Dis.* 154(1):84-94 (1986), and Pohl et al., "Antifungal Free Fatty Acids: A Review," in Mendez, ed. *Science Against Microbial Pathogens: Communicating Current Research and Technological Advances*, Spain: Formatex Research Center, pp: 61-71 (2011), which are hereby incorporated by reference in their entirety). Consistently, Rodríguez-Sánchez et al., "Activity-Guided Identification of Acetogenins as Novel Lipophilic Antioxidants Present in Avocado Pulp (*Persea americana*)," *J. Chromatogr. B* 942-943:37 45 (2013), which is hereby incorporated by reference in its entirety, reported that fractions with high acetogenin concentration promote lipid peroxidation.

Example 20—Minimum Inhibitory and Bactericidal Concentrations of Extracts

EAE inhibited growth of *L. monocytogenes* at 37° C. and 4° C. with MIC values at 15.6 and 7.8 mg L$^{-1}$, respectively (Table 3). The MBC value was the same as the MIC, which shows the capacity of the extract to be bactericidal (MBC/MIC ratio ≤4). Avosafe® presented a similar behavior, as well as the isolated molecules and Mirenat®. However, Persenone A (Compound 6 in Table 2) was more potent than AcO-avocadenyne (Compound 1 in Table 2), as half the amount was needed to inhibit *L. monocytogenes* growth at 37° C.

TABLE 3

Minimum inhibitory concentration (MIC) and minimum bactericidal concentration (MBC) of an enriched acetogenin extract (EAE) from avocado seed, two isolated acetogenins, Avosafe ® (commercial avocado seed oil enriched in acetogenins), and Mirenat ® (commercial antimicrobial) at 37° C. and 4° C. against *Listeria monocytogenes* (24 h).

|  | 37° C. | | | 4° C. | | |
| --- | --- | --- | --- | --- | --- | --- |
| Sample | MIC (mg L$^{-1}$) | MBC (mg L$^{-1}$) | MBC/MIC ratio[a] | MIC (mg L$^{-1}$) | MBC (mg L$^{-1}$) | MBC/MIC ratio |
| EAE | 15.6 | 15.6 | 1 | 7.8 | 7.8 | 1 |
| Avosafe ® | 15.6 | 31.2 | 2 | 7.8-15.6 | 15.6-31.2 | 2 |
| AcO-avocadenyne (1) | 15.6 | 31.2 | 2 | n.d.[b] | n.d. | n.d. |

TABLE 3-continued

Minimum inhibitory concentration (MIC) and minimum bactericidal concentration (MBC) of an enriched acetogenin extract (EAE) from avocado seed, two isolated acetogenins, Avosafe ® (commercial avocado seed oil enriched in acetogenins), and Mirenat ® (commercial antimicrobial) at 37° C. and 4° C. against *Listeria monocytogenes* (24 h).

| | 37° C. | | | 4° C. | | |
|---|---|---|---|---|---|---|
| Sample | MIC (mg L$^{-1}$) | MBC (mg L$^{-1}$) | MBC/MIC ratio[a] | MIC (mg L$^{-1}$) | MBC (mg L$^{-1}$) | MBC/MIC ratio |
| Persenone A (6) | 7.8 | 15.6 | 2 | n.d. | n.d. | n.d. |
| Mirenat ® | 15.6 | 31.2 | 2 | 7.8-15.6 | 15.6-31.2 | 2 |

Data represent results from independent replicates (n = 3) performed with technical triplicates.
[a]MBC/MIC ratio ≤4 indicates bactericidal activity and >4 bacteriostatic activity (Levison, M. E., "Pharmacodynamics of Antimicrobial Drugs," *Infect. Dis. Clin. North. Am.* 18(3): 451-65 (2004), which is hereby incorporated by reference in its entirety).
[b]Not determined.

Figure 5:
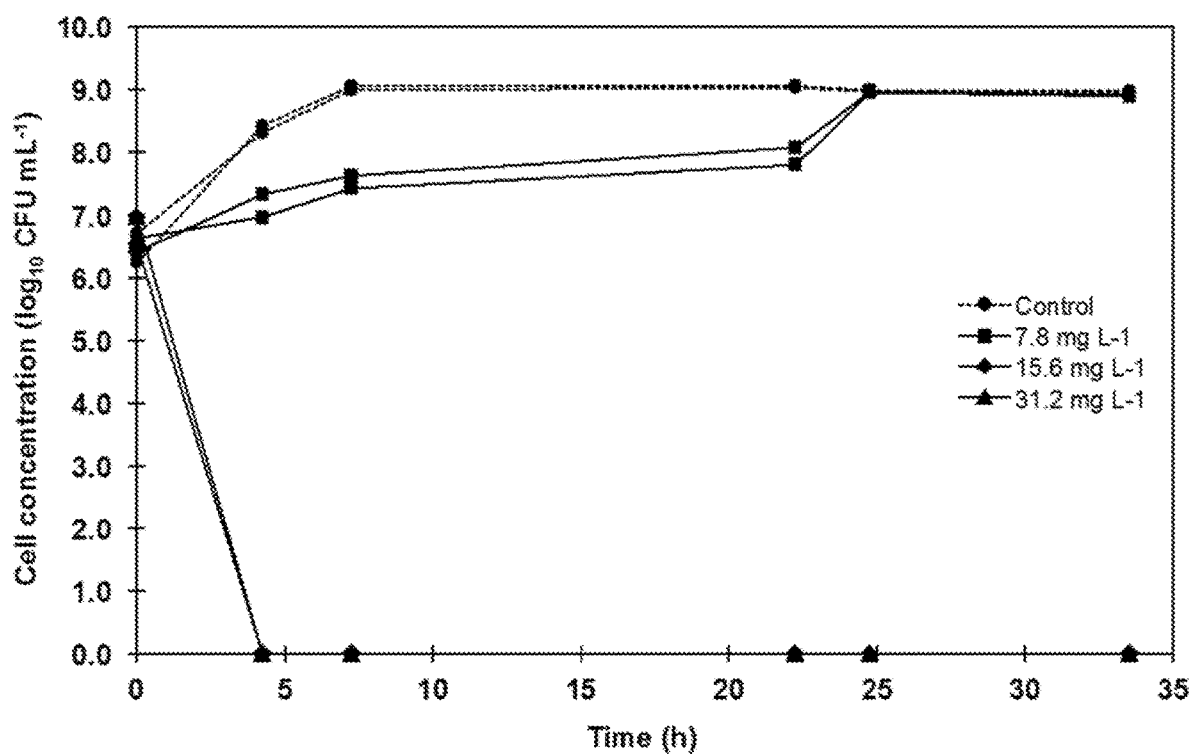
FIG. 5 shows the cell concentration over time of *Listeria monocytogenes* under the presence of different concentrations of Avosafe® (commercial avocado seed oil enriched in acetogenins) during the determination of minimum inhibitory concentration (MIC) (37° C., 34 h). Cell concentration was correlated to OD as follows: $y=(1.74 \times 10^9 * x)-1.39 \times 10^7$ ($R^2=0.96$, n=3), where y is cell concentration (CFU mL$^{-1}$) and x is $OD_{600\,nm}$ under the linear range of the curve. OD measurements were corrected to account for the turbidity of the antimicrobial solution. Initial cell concentration was 6.23-6.98 log CFU mL$^{-1}$. Data represents results from technical duplicates.
Figures 6A, 6B, 6C, 6D:
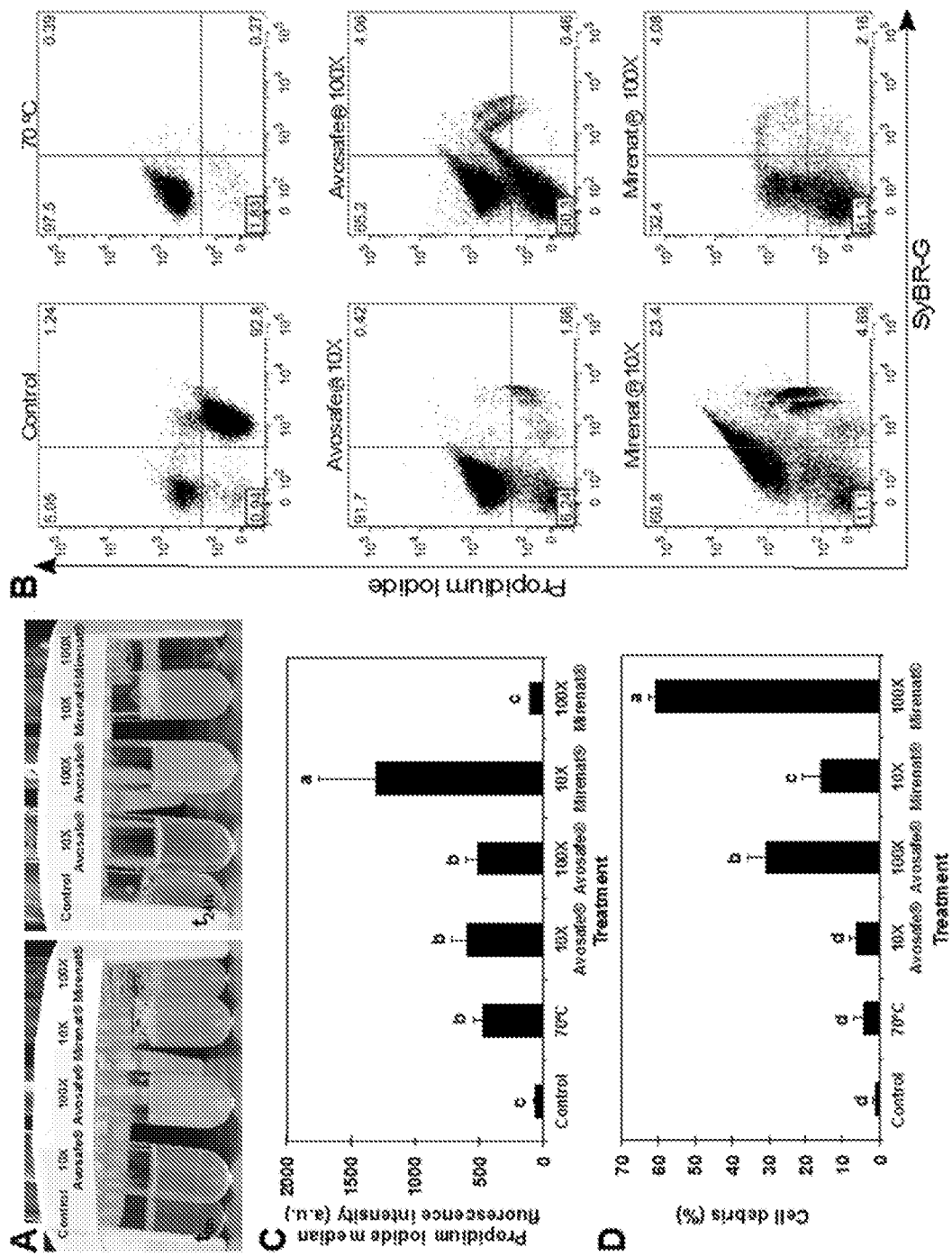
FIGS. 6A-6D show the results of a lysis assay of *Listeria monocytogenes* with 10 and 100×MIC value of Avosafe® and Mirenat® (37° C., 24 h).

Since some of these tests were performed in microplates due to restricted quantities of EAE, results were validated with Avosafe® in test tubes with a working volume of 1 mL (FIG. 5). Throughout the duration of the test, an initial cell concentration of around 6 log (CFU ml$^{-1}$) was inhibited to no visible growth (minimal turbidity) after 4.3 h of contact with 15.6 and 31.2 mg L$^{-1}$ of Avosafe®, which corresponded to the MIC and MBC values, respectively (FIG. 5). The non-inhibitory concentration of 7.8 mg L$^{-1}$ arrested *L. monocytogenes* growth for 22.3 h to 1 log reduction compared to the control. In addition, it was determined that the antimicrobial effect of lethal concentrations of Avosafe® against *L. monocytogenes* were not lytic based on optical density (FIG. 6A). Cell suspensions after 24 h exposure to 10 and 100×MIC value showed no evidence of cell rupture (turbidity remained). In contrast, Mirenat® showed a clear lytic effect at 100×MIC (FIG. 6A). However, flow cytometer (FC) analyses revealed that cells under lethal concentrations of both antimicrobials incorporated propidium iodide (PI) and generated cell debris (FIG. 6B). This effect escalated at 100×MIC, where less PI was internalized (1.2- and 13.5-fold decrease in PI median fluorescence intensity for Avosafe® and Mirenat®, respectively (FIGS. 6C-6D). Even though, FC analysis showed a small percentage of intact cells in all treatments (lower-right quadrant, FIG. 6B), the bactericidal effect of both antimicrobials was confirmed after a second inoculation without the antimicrobial against a positive growth control.

MIC and MBC results were in agreement with the disk diffusion assay in which both avocado extracts (EAE and Avosafe®) presented similar inhibition zones (FIG. 2). However, differences with Mirenat®, as the antimicrobial control, in liquid media were not as drastic as seen in the disc diffusion assay (FIG. 4). Solubility of molecules in liquid versus solid media might contribute to this discrepancy. Although, it was confirmed that Persenone A (Compound 6 in Table 2) was the most potent acetogenin tested and might be responsible to a large extent for the observed antimicrobial activities of the extracts. MBC values observed herein were lower or equal to 10-20 ppm reported for promising fatty acids (C12:0, C18:3) and monolaurin in food matrices against *L. monocytogenes* strain Scott A (Wang et al., "Inhibition of *Listeria monocytogenes* by Fatty Acids and Monoglycerides," *Appl. Environ. Microbiol.* 58(2):624-29 (1992), which is hereby incorporated by reference in its entirety). Also, monolaurin was less inhibitory at 23° C. than at 4° C. as in this study where lower acetogenin concentrations were needed to control *L. monocytogenes* at 4° C. than at 37° C. (Table 3).

At concentrations above the MIC value, no visible growth (minimal turbidity) was observed (FIG. 5). In agreement, FC analyses revealed that lethal concentrations of Avosafe® (10-100×MIC) were associated with an increase in membrane permeability and cell lysis (FIGS. 6A-6C). A similar effect was observed with Mirenat® that has been reported to target the cell membrane and provoke ion leakage, eventually compromising cell membrane potential and resulting in cell death (Rodriguez et al., "Cellular Effects of Monohydrochloride of I-arginine, Nα-lauroyl ethylester (LAE) on Exposure to *Salmonella typhimurium* and *Staphylococcus aureus*," *J. Appl. Microbiol.* 96(5):903-912 (2004), which is hereby incorporated by reference in its entirety).

Example 21—Acetogenins in Avocado Pulp and Seed

In the present study, it was considered relevant to confirm acetogenin content in the edible portion of the avocado fruit (pulp) relative to the seed, from which antimicrobial extracts were obtained. As shown in Table 4, all acetogenins recently reported in Rodríguez-López et al., "A Targeted Metabolomics Approach to Characterize Acetogenin Profiles in Avocado Fruit (*Persea americana* Mill)," *RSC Adv.* 5:106019-29 (2015), which is hereby incorporated by reference in its entirety, which are listed in Table 2, were found in the pulp with the exception of AcO-avocadenyne (Compound 1 in Table 2), exclusively present in the seed. Quantitative extractions of acetogenins in both fruit tissues indicated that acetogenins were more concentrated in the seed by 1.6-fold (5048.1±575.5 and 3107.0±207.2 mg kg$^{-1}$ fresh weight in the seed and in pulp, respectively). Persenone A (Compound 6 in Table 2) was the most abundant acetogenin in the pulp while it was the second after AcO-avocadene (Compound 2 in Table 2) in the seed. In both tissues Persin (Compound 7 in Table 2) and Persenone B (Compound 8 in Table 2) followed in abundance.

TABLE 4

Concentration of acetogenins in pulp and seed of Hass avocado cultivar.

| | Concentration (mg kg$^{-1}$ fresh weight)[a] | |
|---|---|---|
| Compound | Pulp | Seed |
| AcO-avocadyne (0) | N.Q.[d] | N.Q.[d] |
| AcO-avocadenyne (1) | N.D.[e] | 261.7 ± 51.1  d |
| AcO-avocadene (2) | 355.1 ± 12.7  c[b] | 1668.3 ± 269.9 a |

TABLE 4-continued

Concentration of acetogenins in pulp
and seed of Hass avocado cultivar.

| | Concentration (mg kg$^{-1}$ fresh weight)$^a$ | |
|---|---|---|
| Compound | Pulp | Seed |
| AcO-avocadiene A (3) | 352.9 ± 9.4 c | 180.0 ± 6.0 de |
| Persediene (4)$^c$ | 32.6 ± 1.5 e | 88.8 ± 12.3 e |
| Persenone C (5) | 167.6 ± 11.7 d | 220.8 ± 37.0 de |
| Persenone A (6) | 1288.1 ± 89.6 a | 1394.0 ± 119.4 b |
| Persin (7) | 472.0 ± 45.9 b | 639.8 ± 51.8 c |
| Persenone B (8) | 438.7 ± 42.6 b | 594.7 ± 48.1 c |
| Total | 3107.0 ± 207.2 | 5048.1 ± 575.5 |

$^a$Values represent mean ± standard deviation (n = 3).
$^b$Different letters within the same column indicate significant differences (LSMeans Student's t, alpha = 0.05, n = 18-21).
$^c$Quantified in Persenone C (Compound 5 in Table 2) equivalents.
$^d$N.Q.: Not quantified.
$^e$N.D.: Not detected.

As important anti-listerial molecules (FIG. 4), Persenone A (Compound 6 in Table 2) and C (Compound 5 in Table 2) were found at similar levels in the seed and pulp, while AcO-avocadenyne (Compound 1 in Table 2) was exclusively found in the seed. Therefore, avocado seeds are an important source of antimicrobial acetogenins that could be exploited to add value to the waste generated by the avocado industry. In addition, by comparing MIC values to acetogenin concentrations in pulp, it appears that humans are already being exposed to higher levels of these antimicrobial molecules. For example, concentrations of Persenone A (Compound 6 in Table 2) in pulp are 165-times higher than its MIC value (7.8 mg L$^{-1}$) (Table 3). Whether these compounds are bioavailable once ingested by humans is not known. Acetogenins are fatty acid derivatives that concentrate in specialized cells known as idioblasts, these cells possess thick multi-layer cell walls composed of cellulose and suberin that could be hard to digest (Baas et al., "A Survey of Oil Cells in the Dicotyledons With Comments on Their Replacement By and Joint Occurrence With Mucilage Cells," Israel J. Bot. 34(2-4):167-86 (1985); Barrientos et al., "Anatomia Del Fruto de Aguacate, ¿Drupa o Baya?," Revista Chapingo 2(2):189-98 (1996), which are hereby incorporated by reference in their entirety). However, there is evidence that processing technologies cause idioblast disruption freeing acetogenins that could be easily absorbed in the human gut. Microwave of avocado pulp for more than 40 s at 633 W (applied energy >1 KJ g-1) produced idioblast oil leakage to complete emptying of cells (Guzmán-Gerónimo et al., "Cambios en el Perfil de Ácidos Grasos y Microestructura de Aguacate Hass Tratado Con Microondas," Archivos Latinoamericanos de Nutrición 58(3):298-302 (2008), which is hereby incorporated by reference in its entirety). Also, technologies used to commercially extract avocado oil might facility acetogenin bioavailability. Brown, B. I., "Isolation of Unpleasant Flavor Compounds in the Avocado," J. Agric. Food Chem. 20(4):753-7 (1972), which is hereby incorporated by reference in its entirety, demonstrated the presence of at least eight molecules containing a terminal acetylene group (structurally similar to AcO-avocadenyne (Compound 1 in Table 2)) on commercial crude and rectified oils from avocado pulp. These analyzed oils were of unknown origin, likely from different avocado varieties and maturity stages; however, acetogenins appear to be widespread among avocado varieties as confirmed by Rodríguez-López et al., "A Targeted Metabolomics Approach to Characterize Acetogenin Profiles in Avocado Fruit (Persea americana Mill.)," RSC Adv. 5:106019-29 (2015), which is hereby incorporated by reference in its entirety. Therefore, further studies are needed to assess acetogenin bioavailability once consumed by humans.

It is also important to evaluate the toxicity of these molecules before considering acetogenins as natural food additives. To date, literature reports present contradictory results on toxicity of a few isolated acetogenins. Craigmill et al., "Pathological Changes in the Mammary Gland and Biochemical Changes in Milk of the Goat Following Oral Dosing With Leaf of the Avocado (Persea americana)," Aust. Vet. J. 66(7):206-11 (1989), which is hereby incorporated by reference in its entirety, observed that the ingestion of avocado leaves, which contain high concentrations of persin (Rodriguez-Saona et al., "Biologically Active Aliphatic Acetogenins From Specialized Idioblast Oil Cells," Curr. Org. Chem. 4:1249-60 (2000), which is hereby incorporated by reference in its entirety), generated mammary gland necrosis in lactating livestock. Then, Oelrichs et al., "Isolation and Identification of a Compound From Avocado (Persea americana) Leaves Which Causes Necrosis of the Acinar Epithelium of the Lactating Mammary Gland and the Myocardium," Natural Toxins 3(5):344-9 (1995), which is hereby incorporated by reference in its entirety, reported as toxic acute doses of persin at 60-100 mg kg$^{-1}$ body weight in lactating mice. Based on concentrations of acetogenins in avocado pulp (Table 4), to reach these toxic levels a 70 kg person would need to ingest 8.9-14.8 kg of avocado pulp in one sitting, assuming that the only possibly toxic acetogenin is persin (7), or 1.4-2.3 kg of avocado pulp in one sitting assuming that all acetogenins exhibit similar toxicity as persin. These amounts are substantially higher (109-10 times) than the daily-recommended intake of one Hass avocado per day (0.136 kg d$^{-1}$) and, thus, highly improbable (Wang et al., "Effect of a Moderate Fat Diet With and Without Avocados on Lipoprotein Particle Number, Size and Subclasses in Overweight and Obese Adults: A Randomized, Controlled Trial," J. Am. Heart Assoc. 4(1):e001355-67 (2015), which is hereby incorporated by reference in its entirety). In addition, MIC values (7.8-15.6 mg L$^{-1}$) observed in this study to control L. monocytogenes are 3.8-12.8 times lower than the reported persin toxicity (60-100 ppm). Contrary to the above reports, Kawagishi et al., "Liver Injury Suppressing Compounds From Avocado (Persea americana)." J. Agric. Food Chem. 49(5):2215-21 (2001), which is hereby incorporated by reference in its entirety, described a protective effect of acetogenins, including persin, in liver injury at a dose of 100 mg kg$^{-1}$ of body weight. Also, the highest cytotoxic effects of avocado extracts have been reported for molecules in the Avocatin family (C19 structure with C-2 and C-4 hydroxyl groups, such as AcO-avocadyne (Compound 0 in Table 2), AcO-avocadenyne (Compound 1 in Table 2), AcO-avocadene (Compound 2 in Table 2) and AcO-avocadiene A (Compound 3 in Table 2)), which does not include persin, a C23 structure (Ramos-Jerz, M. R., "Phytochemical Analysis of Avocado Seeds (Persea americana Mill., c.v. Hass) [PhD thesis]. Gottingen, Germany: Universitat Carolo-Wilhelmina. 311 p. Available from: Cuvillier Verlag Webshop, Gottingen, Germany, which is hereby incorporated by reference in its entirety). In addition, antimicrobial activity of persin (Compound 7 in Table 2) was reported minimal against C. sporogenes (Rodríguez-Sánchez et al., "Isolation and Structure Elucidation of Avocado Seed (Persea americana) Lipid Derivatives That Inhibit Clostridium sporogenes Endospore Germination," J. Agric. Food Chem. 61(30):7403-11 (2013), which is hereby incorporated by reference in its entirety). The present work documented the potential of acetogenins as natural antimicrobial additives, effective at lower levels than those already consumed by humans.

This is the first report that describes the anti-listerial potential of avocado acetogenins. This study demonstrated that enriched acetogenin extracts from avocado seeds obtained at a laboratory scale (EAE) and commercially available (Avosafe) possess similar anti-listerial properties and chemical profiles. Persenone C (Compound 5 in Table 2), Persenone A (Compound 6 in Table 2) and AcO-avocadenyne (Compound 1 in Table 2) were the most potent acetogenins, the latter confirmed as exclusively present in seed. Anti-listerial activity not only depended on a trans-enone feature but also on the number of unsaturations in the aliphatic chain of the molecule, when both features are combined anti-listerial properties appeared to be potentiated. MIC values of extracts and two isolated acetogenins varied between 7.8-15.6 mg and showed a bactericidal effect, probably caused by an increase in membrane permeability that results in cell lysis. The lytic effect was evident at 10-100×MIC value by flow cytometry. Inhibitory concentrations were effective at 37° C. and refrigeration temperatures (4° C.). Seeds contained 1.6 times higher acetogenin levels than pulp, and total acetogenin content in pulp was 199-398 times higher than MIC values. Therefore, levels consumed by humans are higher than inhibitory concentrations. These results strengthen the potential of avocado acetogenins, especially from avocado seed, as a source for natural antimicrobial food additives.

Example 22—Incorporation of AVOSAFE® at 7,500 Ppm into a Model Food System Stored at 20±2° C. for Up to 96 h Materials and Methods Chemicals. The avocado seed oil extract was obtained from freeze-dried avocado seeds in a food-grade certified facility under good manufacturing practices. Tween 20 (Cat. No. P1379, ≥40% lauric acid, saponification value 40-50, hydroxyl value 96-108 mg g-1) and propylene glycol (PG; ≥99.5 wt % food-grade) were purchased from Sigma Aldrich (St. Louis, Mo., USA).

Inoculum preparation. *Listeria monocytogenes* (ATCC 35152) was purchased from the ATCC (Manassas, V.A., U.S.A.). For experimentation, frozen stocks were first activated in Brain Heart Infusion (BHI) broth (Becton, Dickinson and Co., Franklin Lakes, N.J., U.S.A.) for 13 to 15 h at 37° C. A subculture was prepared under the same growth conditions to ¾ log phase (6 to 7 h). At this stage, cells were adjusted with BHI to an initial optical density (OD) at 600 nm of 0.15, which corresponded to $8 \times 10^6$ CFU/mL and served for further inoculation of the food matrices.

Avosafe® formulation. Avosafe® at 380,100 ppm acetogenins (antimicrobial compounds) was prepared by mixing avocado seed oil (containing 480,000 ppm acetogenins) and propylene glycol (PG) in a ratio of 80:20 w/w.

Model food system and microbiological analysis. Sterile commercial baby food puree (Gerber Nestle, CDM, Mexico) containing mainly beef, vegetables and rice (water, 13% beef, 11% carrots, 7% green beans, 3% rice, vegetable oil mix-sunflower, coconut and soybeans-, 1% tomato paste, 1% dehydrated potato, 1% dehydrated peas, rice flour, butter, natural flavorings (beef, garlic and onion), iodized salt, chicken fat, iron, zinc and folic acid) was purchased at a local supermarket. Table 5 shows the nutrition facts of the food product as reported on its label. All ingredients were aseptically incorporated under a biological safety cabinet where an analytical balance was used to precisely add each ingredient. To ensure adequate homogenization of the system, ingredients were added in the following order: baby food puree (10% w/w), Avosafe® (1.97% w/w), baby food puree containing 0.038% Tween 20 (87.03%) and microbial inoculum (1% v/w). PG concentration used was adjusted to the maximum allowed concentration in processed meat products (0.4% w/w) accordingly to Mexican Official Standards (Health Secretary, 2005). Tween 20 final concentration was 0.03% w/w. The target microbial inoculum level was around 3 log. A total of 16 g of the model food system, containing 7500 ppm acetogenins, were prepared and then divided into twelve 50-mL Falcon tubes (each one containing 1 g) and incubated at 20±2° C. (to simulate temperature abuse and accelerate changes in the food system) for 3, 24, 48 and 96 h (three tubes were sampled per time). In addition, positive and negative growth controls were included. Avosafe® was substituted for PG (2.5% w/w final concentration), and the inoculum was replaced by sterile dH2O, for positive and negative controls, respectively. At the end of the incubation period microbial counts were conducted by plating out the serially diluted sample (1 g of food sample in 9 mL 1×PBS) onto BHI agar medium in triplicates. Plates were incubated for 36 h at 37° C.

TABLE 5

Proximate composition of commercial baby food puree employed as model food system.

| Ingredient | 1 container (113 g) |
|---|---|
| Total Fat (g) | 4.0 |
| Saturated fat (g) | 1.1 |
| Total Carbohydrates (g) | 8.0 |
| Dietary fiber (g) | 0.45 |
| Sugars (g) | 1.5 |
| Protein (g) | 3.5 |
| Sodium (mg) | 90 |
| Iron (mg) | 15 |
| Zinc (mg) | 1.1 |
| Folic acid (µg) | 11 |

Results

Avosafe® formulation. Since acetogenins are lipophilic molecules, PG was used as vehicle, providing translucent solutions denoting adequate solubility. In addition, Tween 20 was used as a surfactant, to improve Avosafe® stability and performance, however in accordance with our observations (data not shown), other studies have described that the antimicrobial activity of lipidic substances is reduced by the incorporation of surfactants at high concentrations (Remmal A, et al., "Inhibition of Antibacterial Activity of Essential Oils By Tween 80 and Ethanol in Liquid Medium," *J. Pharm. Belg.* 48(5):352-6 (1993); Hammer et al., "Antimicrobial Activity of Essential Oils and Other Plant Extracts," *J Appl. Microbiol.* 86:985-90 (1990); Ma Q, et al., "Antimicrobial Properties of Microemulsions Formulated with Essential Oils, Soybean Oil, and Tween 80," *Int J Food Microbiol.* 226:20-5 (2016), which are hereby incorporated by reference). At these concentrations, molecules of Tween might hydrophobically bind to the lipidic molecules reducing the interaction with bacteria cells (Ma Q, et al., "Antimicrobial Properties of Microemulsions Formulated with Essential Oils, Soybean Oil, and Tween 80," *Int J Food Microbiol.* 226:20-5 (2016), which is hereby incorporated by reference). In contrast, low concentrations of Tween appear to increase antimicrobial concentration in the continuous phase of the emulsion, facilitate access through the cell membrane, and improve interactions between cells and antimicrobial molecules (Gaysinsky et al., "Antimicrobial Efficacy of Eugenol Microemulsions in Milk Against *Listeria monocytogenes* and *Escherichia coli* O157:H7" *J Food Pro* 70: 2631-37 (2007), which is hereby incorporated by reference in its entirety. Therefore, to avoid inactivation of Avosafe®, by interaction with Tween 20, the surfactant concentration was kept as low as possible (<0.03%) and was first incorporated into a portion of the food matrix and then Avosafe® was added.

Effects of incorporation of Avosafe® at 7500 ppm into a model food system stored at 20±2° C. for up to 96 h on viability of *Listeria monocytogenes*. In response to the severity of *Listeria monocytogenes* infections as well as the number of food recalls, the USDA Food Safety and Inspection Service (USDA/FSIS) established rules/guidelines for RTE meat and poultry manufacturers to have better control of the pathogen in their products (FSIS) Food Safety and Inspection Service, FSIS Compliance Guideline: *Controlling Listeria monocytogenes in Post-lethality Exposed Ready-to-Eat Meat and Poultry Products* (2012), available at http://www.fsis.usda.gov/PDF/Controlling_LM_RTE_guideline_0912.pdf (accessed 12 Jun. 2013), which is hereby incorporated by reference in its entirety). This ruling provides manufacturers with three options for determining the degree to which regulatory testing would be implemented for their plant/product: 1) use of both a post-process lethality step AND an antimicrobial agent to control outgrowth (lowest testing frequency); 2) use of either a post-processing lethality step OR an antimicrobial agent to control outgrowth (moderate testing frequency); 3) use of appropriate sanitation alone (most testing).

Figure 7:
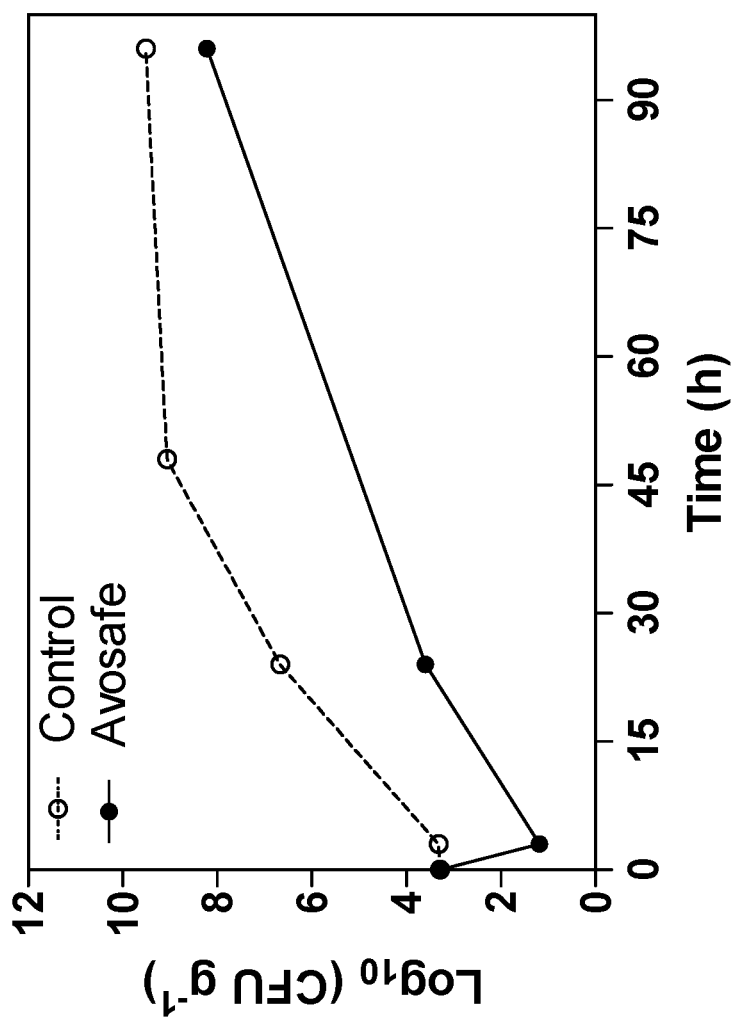
FIG. 7 shows the growth of *Listeria monocytogenes* in a model food system with and without 7500 ppm Avosafe®, stored at 20±2° C. for 96 h. Values represent average ±SD (n=3).

The results here showed that the target inoculation of 3 log ($10^3$ CFU/g of food product) of *Listeria monocytogenes* was successful in the model food matrix (see control, FIG. 7). This inoculation level mimics the counts likely to occur in commercial RTE products (Wong, T. L., et al., "Microbiological Quality of Pre-Packaged Pâté and Ham in New Zealand," *Lett. Appl. Microbiol.* 41:106-111 (2005), which is hereby incorporated by reference in its entirety) and is also within the suggested levels ($10^2$-$10^5$ CFU/g) to be used for post-processing lethality or antimicrobial agent tests evaluation (Scott et al., 2005; Health Canada, 2012). A high incubation temperature (20±2° C.) was used to simulate temperature abuse and to test accelerated microorganism outgrowth.

In addition, FIG. 7 showed a 2 log reduction in *Listeria* counts immediately after incorporation of 7500 ppm Avosafe® at 3 h, when compared to the positive growth control. After 24 h, counts were around the initial inoculum (3.6 log) and at 96 h of incubation, *Listeria* reduction compared to the control was only 1.3 log. This data suggested the potential of Avosafe® as an antimicrobial agent to control *Listeria* outgrowth and meet the *Listeria* Rule requirements. Therefore, a further study at refrigerated temperature was performed.

Example 22—Incorporation of AVOSAFE® at 10,000 Ppm into a Model Food System Stored at 4±1° C. for Up to 72 Days Materials and Methods Chemicals and inoculum preparation. Chemicals and inoculum preparation were as described in previously section of Example 22.

Avosafe® formulation. Avosafe® at 402,850 ppm acetogenins (antimicrobial compounds) was prepared by mixing avocado seed oil (containing 479,400 ppm acetogenins) and propylene glycol (PG) in a ratio of 84:16 w/w.

Model food system and microbiological analysis. A similar procedure described in Example 21 was used, with some modifications. All ingredients (10% w/w baby food puree, 2.48% w/w Avosafe®, 86.52% baby food puree containing 0.039% Tween 20 and 1% v/w microbial inoculum) were aseptically incorporated under a biological safety. A total of 16 g of the model food system, containing 10,000 ppm acetogenins, were prepared and then divided into twelve 50-mL Falcon tubes (each one containing 1 g) and incubated at 4±1° C. to simulate refrigerated conditions. Samples were taken at 0, 0.125, 20, 40, 60 and 72 days (two tubes per time). In addition, positive and negative growth controls were included. Avosafe® was substituted for PG and the inoculum was replaced by sterile dH2O for positive and negative controls, respectively. At the end of the incubation period, microbial counts were conducted by plating out serially dilute samples (1 g sample in 9 mL 1×PBS) onto BHI agar medium in triplicates. Plates were incubated for 36 h at 37° C.

Effects of incorporation of Avosafe® at 10,000 ppm into model food system stored at 4±1° C. for up to 72 days on viability of *Listeria monocytogenes*. Treatment with 10,000 ppm Avosafe® combined with refrigerated storage (4±1° C.) showed a strong bactericidal action towards *L. monocytogenes* (Table 6). Counts decreased from a 3 log inoculum count to undetectable levels within 3 h of antimicrobial incorporation. Avosafe® antilisterial effect continued to end of the experimental period (72 days), whereas the positive growth control reached 9 log at 20 days and maximum counts (9.5 log) were observed at 40 days of storage.

*L. monocytogenes* can survive under relatively extreme physicochemical conditions such a wide range of temperatures (as low as −0.4° C. and as high as 45° C.), pH (4.4-to 9.4), and high salt content (Swaminathan et al., "*Listeria monocytogenes*," in *Food Microbiology: Fundamentals and Frontiers* (Doyle and Beuchat, editors), ASM Press (2007) 322-41 and Orgaz et al., "Biofilm Recovery from Chitosan Action: A Possible Clue to Understand *Listeria Monocytogenes* Persistence in Food Plants," *Food Contr.* 32:484-89 (2013), which are hereby incorporated by reference in their entirety). Given the persistence of *L. monocytogenes* in the food-processing environment (Soni et al., "Reduction of *Listeria monocytogenes* in Queso Fresco Cheese by a Combination of Listericidal and Listeriostatic GRAS Antimicrobials," *International Journal of Food Microbiology* 155(1-2):82-88 (2012), which is hereby incorporated by reference in its entirety) and its psychrotrophic character, is a pathogen of concern in refrigerated food products, such as ready-to-eat (RTE) meat products, cheese and milk (Rocourt & Cossart, "*Listeria monocytogenes* on Commercially-Produced Frankfurters Prepared With and Without Potassium Lactate and Sodium Diacetate and Surface Treated with Lauric Arginate using the Sprayed Lethality in Container (SLIC) Delivery Method," *Meat Science*, 85(2): 312-18 (1997), which is hereby incorporated by reference in its entirety). In this sense, Avosafe® at 10,000 ppm in combination with refrigeration (4° C.) represents a practical implication from the processor's standpoint, as an effective bactericidal hurdle to comply with the zero tolerance policy for *L. monocytogenes* in RTE foods (i.e., 1<CFU/25 g) adopted by U.S. regulatory agencies. (CFR) Moreover, Avosafe® at 10,000 ppm in combination with refrigeration (4° C.) may successfully satisfy *Listeria* Rule requirements for refrigerated RTE products, since it is stated that antimicrobial agents used in alternative 1 and 2 should allow no more than 2 log of growth over the shelf life of the product.

TABLE 6

*Listeria monocytogenes* counts ($\log_{10}$ CFU/g) in model food system with and without 1,000 ppm Avosafe ®, stored at 4 ± 1° C. for 72 days.

| Time (day) | Control 0 ppm Avosafe ® (Control) | Treatment 10 000 ppm Avosafe ® |
|---|---|---|
| 0 | 3.00 ± 0.02 | 3.00 ± 0.02 |
| 0.125 | 3.41 ± 0.02 | ND[a] |
| 20 | 8.90 ± 0.02 | ND |
| 40 | 9.49 ± 0.01 | ND |
| 60 | 9.29 ± 0.03 | ND |
| 72 | 8.86 ± 0.08 | ND |

Values represent average ± SD (n = 3).
[a]Not detected.

Example 23—Incorporation of AVOSAFE® at 10,000 Ppm into a Ready-to-Eat Meat Product (Sausage) Stored at 4±1° C. for Up to 107 Days Materials and Methods Chemicals and inoculum preparation. Chemicals and inoculum preparation were as described in previously section of Example 22. In addition, carmine (E120), as a natural colorant, was obtained from Trades S.A. (Barcelona, Spain).

Avosafe® formulation. Avosafe® at 403,360 ppm acetogenins (antimicrobial compounds) was prepared by mixing avocado seed oil (containing 480,000 ppm acetogenins) and propylene glycol (PG) in a ratio of 84:16 w/w.

Sausage manufacture. Ready-to-eat turkey sausages were freshly manufactured under commercial conditions at the pilot plant of a local producer/collaborator. Frozen turkey breasts obtained from a commercial supplier were thawed at 2.2 to 4.4° C. immediately before use. Turkey was ground through a 4.76-mm plate attached to a grinder (model MJ-12, Torrey, Monterrey, NL, Mexico). Sausage formulation (ca. 10 kg for each treatment) contained the base ingredients shown in Table 7. Treatment A contained 10000 ppm of Avosafe® and Tween 20 as surfactant (3.16 and 0.04% of a turkey breast weight basis, respectively). Treatment B served as the conventionally cured control, containing 156 ppm of sodium nitrite and propylene glycol, instead of Avosafe® (0.02 and 3.18% of a turkey breast weight basis, respectively). The fresh ground turkey with a portion of water (as ice) were mixed thoroughly in a vacuum bowl cutter (model VSM65, Kramer & Grebe GmbH & Co. KG., Biendenkopf-Wallau, Germany). After initial mixing and chopping at 3° C., nonmeat base ingredients (together with Tween 20 for treatment A or sodium nitrite for treatment B) were dissolved in water and added to the batter and chopping continued until the meat blend temperature reached 13 to 15° C. Then Avosafe® or propylene glycol were incorporated to achieve an emulsion at a final temperature of 20° C. After chopping was complete, the batter was vacuum stuffed (stuffer model RS 4003-165, Risco, Stoughton, Mass.) into a cellulose casing. Five-hundred (500 g) of treatment A were removed to be packaged as un-cooked samples for further evaluation of thermal processing on acetogenin concentration. Sausages were thermally processed to a minimum internal temperature of 75° C. in a thermal processing oven (Maurer, AG, Reichenau, Germany; Alkar model MT EVD RSE 4, Alkar Engineering Corp., Lodi, Wis.). Product was chilled to below 4° C. in a cold room, peeled, and vacuum packaged (Type AG800, Multivac, Kansas City, Mo.) in barrier bags (Cryovac B540, Cryovac Sealed Air Corp., Duncan, S.C.) as half pound packages (four sausages per package, each of ca. 60 g) and pasteurized at 85° C. for 10 min. The product, obtained directly from the producer/collaborator, was transported on ice to the laboratory (Monterrey, N.L., Mexico) and stored at 4° C. for 12 h prior to inoculation with *L. monocytogenes*.

TABLE 7

Base formulation for manufacture of turkey sausages and antimicrobial agent.

| | Ingredient | %[a] | Treatment A Avosafe ® (g) | Treatment B Conventionally cured control (g) |
|---|---|---|---|---|
| Base formulation | Turkey breast | 100.00 | 7880.0 | 7880.0 |
| | Water/ice (50/50 mix) | 20.00 | 1570.0 | 1570.0 |
| | Salt | 1.41 | 110.5 | 110.5 |
| | Modified food starch | 2.00 | 157.0 | 157.0 |
| | Sodium tripolyphosphate | 0.40 | 31.0 | 31.0 |
| | Carmine | 0.06 | 4.70 | 4.70 |
| Antibacterial agent | Sodium nitrate | 0.02 | — | 1.6 |
| | Tween 20 | 0.04 | 3.5 | — |
| | Avosafe | 3.16 | 248.0 | — |
| | Propylene glycol | 3.18 | — | 245.5 |
| Total batch (g) | | | 10,000.0 | 10,000.0 |

[a]Formulated ingredients reported as ingoing percentage of a turkey breast.

Sample inoculation. Sausages of each treatment were aseptically removed from the original package and individually transferred into a sterile Whirl-Pak stomacher bags (Fisher Scientific, Pittsburgh, Pa., USA) under a biological safety cabinet (Model 1375, Thermo Scientific, CA, USA). Then, each sausage was surface inoculated with 0.45 mL of the *L. monocytogenes* suspension to give a final concentration of 3 log ($1 \times 10^3$ cfu/g) and massaged by hand for ca. 2 min to ensure adequate coverage of the inoculum on all the sausage surface. After, three individually packed sausages were vacuum sealed (FoodSaver model V2244, Rye, N.J.) in a nylon-polyethylene bag (75 μm standard barrier; oxygen transmission rate: 63 $cm^3/m^2$, 24 h at 23° C. and 0% relative humidity; moisture vapor transmission rate: 4.8 $g/m^2$, 24 h at 37° C. at 90% relative humidity; Uline, Apodaca, N.L., Mexico). Inoculated samples were left to stand at room temperature (25° C.) for 20 min to allow bacterial attachment. Then, packages were stored at 4±1° C. for up to 107 days.

Microbiological analysis. *L. monocytogenes* counts were determined in triplicate per treatment after 0.125, 1, 10, 20, 30, 40, 60, 75, and 90 d of incubation. In addition, the native microbial flora of the sausages was determined by aerobic plate count. On the appropriate day, one package of each treatment was collected and opened aseptically. Each sausage, with a wet weight of around 60 g, was transferred to a sterile Whirl-Pak stomacher bag (Nasco, Ft. Atkinson, Wis.) and 240 mL of 1×PBS (pH 7.2) were added to achieve a 1:5 dilution. Each sample was stomached for 2 min at 230 rpm in a laboratory blender (Stomacher 400, Seward Medical, London, UK). All blended samples were maintained on an ice slush. Appropriate dilutions were plated with a glass rod in triplicates on BHI or Plate Count agar for *L. mono-*

*cytogenes* or native flora determination, respectively. Agar plates were incubated at 37° C. for 36 h and CFU from each plate were counted, recorded, averaged, and reported as log 10 of CFU per gram.

Physicochemical characterization of the product. To determine pH, slurry of the sausage was prepared by homogenizing 1 g of sample with 9 mL of deionized water. A portable Minolta Chroma Meter (CR310, Minolta, Ramsey, N.J.) was used for color analysis, which employs the L*a*b* color spectra. To account for the packaging material, a single sheet of the film was placed over the calibration plate before the color measurements were conducted. After calibration, five measurements per package were taken and averaged. The proximate composition of treatments was determined after 10 months of storage at −80° C., using methods stated by the Association of Official Analytical Chemists (McNeal, J. E., "Meat And Meat Products," in K. Herlich (Ed.), Official Methods Of Analysis (15th ed.) (pp. 931-938). Arlington (Va.): Association of Official Analytical Chemists (1990), which is hereby incorporated by reference in its entirety) as conducted by a commercial testing laboratory.

Effect of thermal processing and storage on acetogenins concentration. Acetogenins in sausages (Treatment A: uncooked, day 0 and 90) were extracted and quantified as reported by Salinas-Salazar et al, "Inhibitory Activity of Avocado Seed Fatty Acid Derivatives (Acetogenins) Against *Listeria Monocytogenes*" *J Food Sci* 82: 134-44 (2016), which is hereby incorporated by reference in its entirety, with some modifications. Three grams (3 g) of sample were homogenized with acetone (1:5, w/v) using an Ultra-Turrax T25 homogenizer (IKA Works, Willmington, N.C., USA.) at 11000 rpm for 3 min, sonicated for 5 min, and centrifuged at 3600 rpm for 6 min (5° C.). Supernatants were collected and the precipitated material was extracted again two times, as mentioned above. After, supernatants were mixed and the solvent was evaporated at 35° C. using a rotary evaporator (Büchi R-210, Büchi Labortechnik AG, Switzerland) under high vacuum (22 in Hg). Residue was partitioned in 10 mL hexane:methanol (1:1). After 30 s of vortex, phases were separated by centrifugation (4000 rpm, 10 min) and the lower phase (methanol) was recovered and washed two more times with hexane, taken to dryness under nitrogen gas, resuspended in 1 mL isopropanol and passed through a 0.45 µm PTFE filter prior to HPLC injection. Agilent HPLC systems (Santa Clara, Calif., USA) 1260 Infinity series coupled to a G4212B photodiode array detector (PDA) and an evaporative light scattering detector G4218A was used. The PDA detector was set at 220 and 208 nm (Rodríguez-López, "A Targeted Metabolomics Approach to Characterize Acetogenin Profiles in Avocado Fruit (*Persea americana* Mill.)" *RSC Adv* 5: 106019-29 (2015), which is hereby incorporated by reference in its entirety).

Figure 8A:
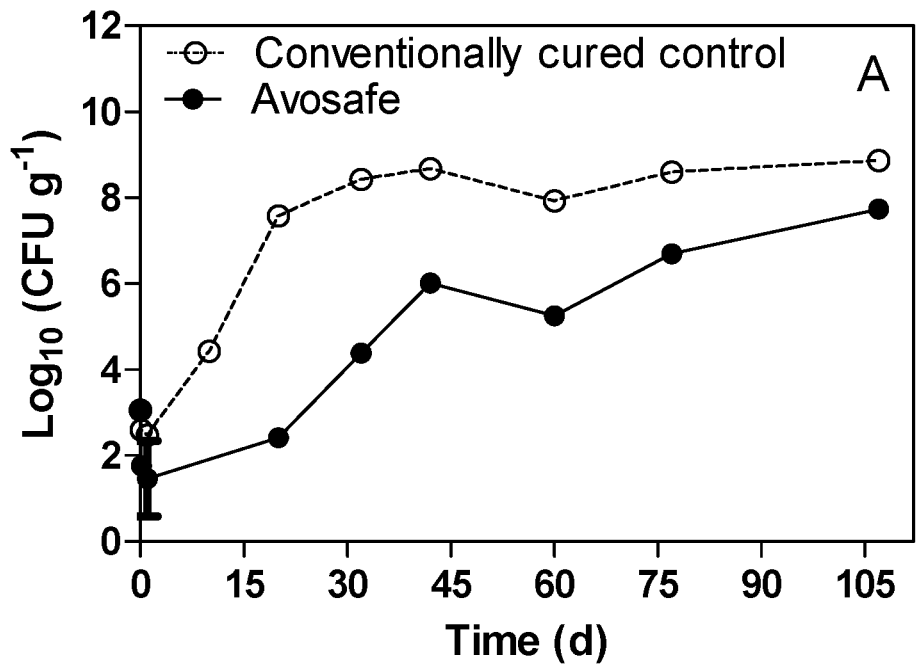
FIGS. 8A-8B show microbial growth in a ready to eat (RTE) meat product (sausage) stored at 4±1° C. for 107 days formulated with Avosafe® (10,000 ppm acetogenins) and conventionally cured control (156 ppm nitrites).
Figure 8B:
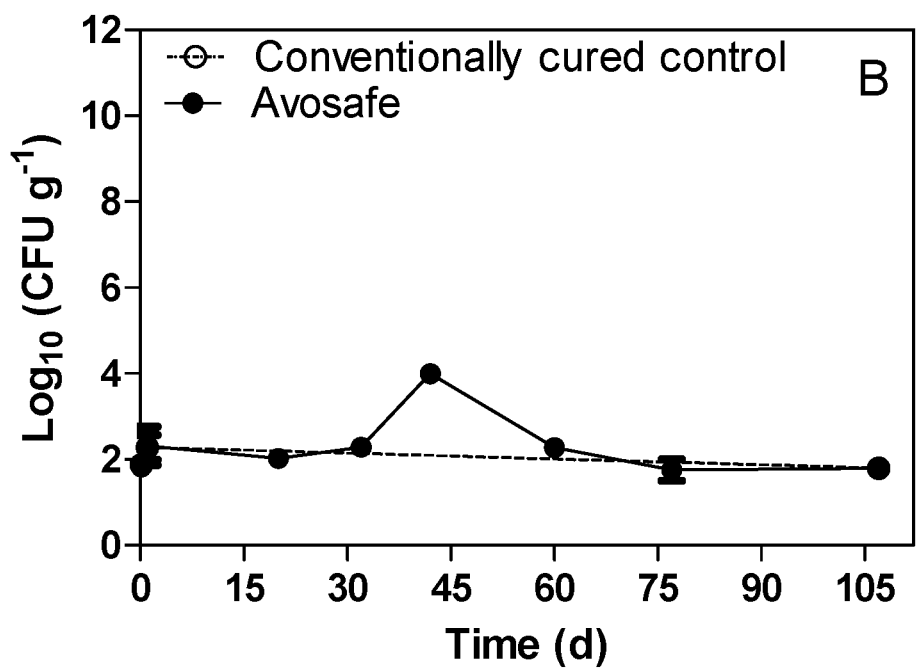

Effects of incorporation of Avosafe® at 10000 ppm into a ready-to-eat meat product (sausage) stored at 4±1° C. for 107 days. As shown in FIG. 8A, 10,000 ppm Avosafe® was more effective at reducing *L. monocytogenes* counts during 107 days of refrigerated storage than the conventionally cured control containing nitrites, showing log reductions below the inoculation number (i.e., <3 log) for up to 20 days (a 5 log reduction compared to the control). After, log reductions ranged from 4 to 3 from day 30 to 60 (P<0.05) and, at day 77, *Listeria* counts were around 1 log lower than the conventionally cured control. In addition, only two colony morphotypes were identified as the native flora of the sausages, which throughout the experimental period remained in the same numbers in both the control and Avosafe® treatment (FIG. 8B). Their colonies were drastically larger than *Listeria* and easily identified. *Listeria* outgrowth during refrigerated storage in conventionally cured sausages (containing 156 ppm of sodium nitrite) was in agreement with previous reports for RTE roast beef and turkey meat products (Porto-Fett, et al., "Control of *Listeria monocytogenes* on Commercially-Produced Frankfurters Prepared With and Without Potassium Lactate and Sodium Diacetate and Surface Treated with Lauric Arginate Using the Sprayed Lethality in Container (slic) Delivery Method." *Meat Science*, 85(2):312-318 (2010) and Chibeu, et al., "Efficacy of Bacteriophage LISTEX P100 Combined with Chemical Antimicrobials in Reducing *Listeria Monocytogenes* in Cooked Turkey and Roast Beef," *International Journal of Food Microbiology*, 167(2):208-214 (2013), which are hereby incorporated by reference in their entirety).

Addition of sodium nitrite and sodium nitrate are not allowed in manufacturing natural and organic processed meat products such as frankfurters and hams (Food Standards and Labeling Policy Book, USDA, 2005, which is hereby incorporated by reference in its entirety). Nitrite is the ingredient responsible for the characteristics pink/red color and flavor of cured meats. In addition, nitrite contributes to the control of pathogens, mainly *Clostridium botulinum* and in a lower degree *Listeria monocytogenes* since the growth of the latter pathogen is not completely inhibited (Glass, K. A., et al., "Antagonistic Effect of Fat on The Antibotulinal Activity of Food Preservatives and Fatty Acids," *Food Microbiol*. 21:675-682 (2004), which is hereby incorporated by reference in its entirety).

Seeking to satisfy the demand for what are labeled as "Uncured", "Natural" or "Clean label" products while still delivering typical cured meat properties, food manufactures are using celery powder, as a natural source of nitrate (requiring a bacterial starter culture to reduce nitrate to nitrite, which is the active ingredient) or pre-converted nitrites from celery powder Jackson et al., "Survival and Growth of *Clostridium perfringens* in Commercial No-Nitrate-or-Nitrite-Added (Natural and Organic) Frankfurters, Hams, and Bacon" *J Food Prot* 74: 410-16 (2011), which is hereby incorporated by reference in its entirety. However, it has been observed that "Uncured" and "No-Nitrate-or-Nitrite-Added" (but including celery powder) commercial meat products typically have lower (P<0.05) residual nitrite concentration than conventionally cured products (Sindelar, J. J., et al., "Investigating Quality Attributes and Consumer Acceptance of Uncured, No-Nitrate/Nitrite-Added Commercial Hams, Bacons, and Frankfurters," *J. Food Sci.* 72(8):5551-9 (2007); Schrader, K. D., "The Control of *Listeria Monocytogenes* on Uncured, No-Nitrate-Or-Nitriteadded Meat Products," Ph.D. dissertation, Iowa State University, Ames (2010); and Sebranek, J. G., et al., "Beyond Celery and Starter Culture: Advances in Natural/Organic Curing Processes in the United States," *Meat Sci.* 92:267-273 (2012), which are hereby incorporated by reference in their entirety) and therefore higher susceptibility to support bacterial growth. In other to meet the USDA label requirements for natural products, without comprising the safety of the products, new alternatives of effective natural antimicrobials are still needed.

In this sense, the findings of our invention suggest that Avosafe® is a promising alternative to fulfill this need, when compared with other natural antibacterials. For example, Xi and others (2011) reported that addition of 1%, 2% or 3% cranberry powder in combination with 150 ppm sodium nitrite to a cooked meat model system (cured) stored a 7° C. resulted in 1.9-4.8 log reduction of *L. monocytogenes* (initial inoculum around 3 log) by day 9, when compared to their conventionally cured control with nitrite alone. While our results indicate that Avosafe® alone at 10000 ppm (2.45% w/w) produced around a 2 log decrease at the same storage time, when compared to their conventionally cured control (FIG. 8A), with the difference that storage was performed at 4° C.

Physicochemical characterization of the product. Our results from proximate composition analyses (Table 8) show no appreciable differences among treatments in the level of moisture, macro nutrients, salt, aw, or pH. Therefore, these parameters are not likely to have exhibited a confounding effect on the microbiological results or chemical characterization of acetogenins in the food product.

TABLE 8

Proximate composition of sausages formulated with Avosafe ® (10,000 ppm acetogenins) and conventionally cured control (156 ppm nitrites).

| Ingredient | Treatment A Avosafe ® | Treatment B Conventionally cured control |
|---|---|---|
| Moisture (%) | | 60.47 |
| Ash (%) | | 2.60 |
| Carbohydrates (%) | | 1.84 |
| Fat (%) | | 22.36 |
| Protein (%) | | 12.36 |
| Sodium chloride (%) | | 1.6-3.4 |
| Water activity | 0.968 ± 001 | 0.973 ± 001 |
| pH | 6.08 ± 0.14 | 6.25 ± 0.03 |
| L* | 63.84 ± 1.05 | 60.30 ± 0.47 |
| a* | 13.55 ± 0.80 | 16.04 ± 0.18 |
| b* | 13.70 ± 0.37 | 14.05 ± 0.48 |

Values represent average ± SD (n = 3).

As previously mentioned, besides its antimicrobial function nitrite is responsible for the formation of the characteristic pink/red color in cured and smoked products (Ruiz-Capillas, C., et al., "Properties of Reformulated Hot Dog Sausage Without Added Nitrites During Chilled Storage," *Food Science and Technology International* 22(1):21-30 (2014) and Ruiz-Capillas C, et al, "Determination of Preservatives in Meat Products by Flow Injection Analysis (FIA)". *Food Additives & Contaminants: Part A*. 25: 1167-1178 (2008), which are hereby incorporated by reference in their entirety). Considering that color decisively dictates the consumer's preference for food products (Barros & Stringheta, "Microencapsulamento de Antocianinas-uma Alternativa para o Aumento de sua Aplicabilidade como Ingrediente Alimenticio" *Biotecnologia Ciência e Desenvolvimento*, 18-24 (2006), which is hereby incorporated by reference in its entirety), other natural food grade ingredients such as cochineal carmine have been used to achieve a similar result in sausage and other processed meat products (Madsen H L, et al., "Cochineal as a Colorant in Processed Pork Meat. Colour Matching and Oxidative Stability," *Food Chemistry* 46:265-271 (1993) and Ruiz-Capillas, C., et al., "Properties of Reformulated Hot Dog Sausage Without Added Nitrites During Chilled Storage," *Food Science and Technology International* 22(1):21-30 (2014), which are hereby incorporated by reference in their entirety).

In L*a*b* color spectra, L* (lightness) measures total light reflected on a scale from 0=black to 100=white (MacDougall, D. B., "Modelling Colour Stability In Meat," Pages 247-262 in *Colour in Food-Improving Quality*. CRC Press LLC, Boca Raton, Fla. (2002), which is hereby incorporated by reference in its entirety). L* values of both treatments (Table 8) are within the typical range reported for cured sausage and ham, which is 50 to 64 (Zhang, X., B et. al., "Production of Cured Meat Color in Nitrite-Free Harbin Red Sausage by *Lactobacillus Fermentum* Fermentation," *Meat Sci*. 77:593-598 (2007) and Paxton, et al., "Research and Reviews: Meat-Effects of Storage and NaOH Treatment on the Quality of Cured, Cooked Hams from Hamp-shire Hogs," *Circular* 172-99. The Ohio State University Department of Animal Sciences. (1999). http://ohioline.osu.edu/sc172/sc172_9. html (accessed Apr. 2, 2009), which are hereby incorporated by reference in their entirety). Also, it have been reported that meat products prepared with nitrite presented higher L* levels than those prepared without nitrite (Li P, et al., "Formation And Identification of Nitrosylmyoglobin by *Staphylococcus* Xylosus in Raw Meat Batters: A Potential Solution for Nitrite Substitution in Meat Products," *Meat Science* 93:67-72 (2013), which is hereby incorporated by reference in its entirety). However, satisfactorily treatment with Avosafe® showed slightly higher L* value than treatment with nitrites (63.84±1.05 and 60.30±0.47, respectively), attributed to carmine action that was added to the sausages in combination with Avosafe®. Moreover, while no significant differences in yellowness (b*) were observed between samples, replacement of nitrite with Avosafe® decreased ($p<0.05$) redness (a*), showing values of 16.04±0.18 and 13.55±0.80, respectively.

Figure 9:
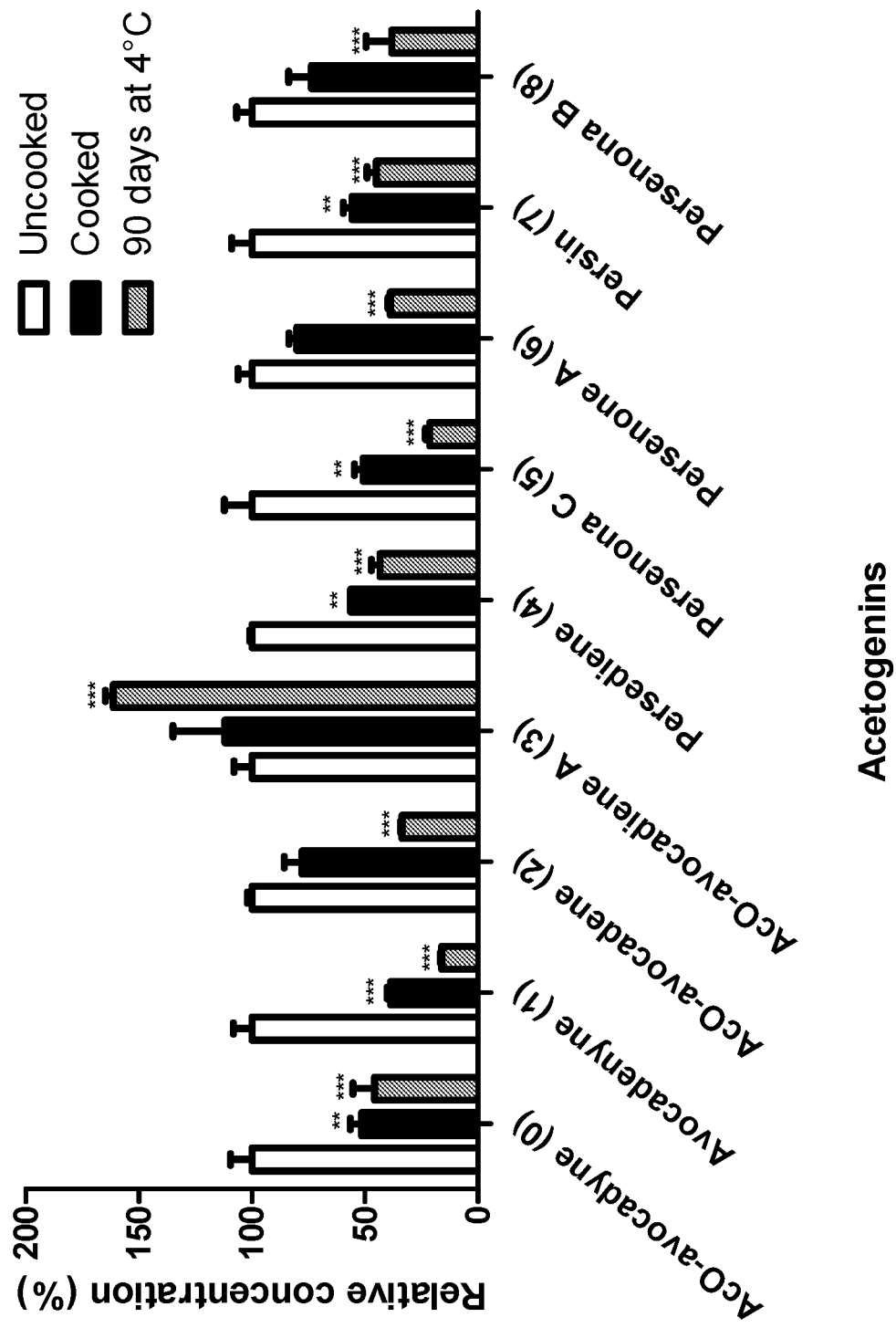
FIG. 9. shows the effect of processing and refrigerated storage (4±1° C.) on relative concentration of individual acetogenins in sausages formulated with 10,000 ppm Avosafe®, before processing (raw), after processing (Day 0) and after 90 days of storage. Values represent mean±SD (n=3). Asterisk indicates significant difference to the control (before processing), p<0.01 (very significant), *p<0.001 (Extremely significant), LSMeans Dunnett.

Effect of processing and refrigerated storage on acetogenins concentration. Processing losses of AcO-avocadene (2), AcO-avocadiene A (3), Persenone A (6) and Persenone B (8) were no statistically significant when compared to the unprocessed control (FIG. 9), whereas the rest of the molecules exhibited losses around 50% (AcO-avocadyne, compound 0 in Table 2, was not quantified). Avosafe's previously observed antibacterial activity against *Clostridium sporogenes* vegetative cells remained unchanged after thermal processing at 75, 100 and 120° C. for 15 min in liquid model systems consisting of ethanol and propylene glycol as vehicles (Pacheco A., et al., "Stability of the Antimicrobial Activity of Acetogenins from Avocado Seed, Under Common Food Processing Conditions, Against *Clostridium Sporogenes* Vegetative Cell Growth and Endospore Germination," *International Journal of Food Science & Technology*. doi: 10.1111/ijfs.13513 (2017), which is hereby incorporated by reference in its entirety). The later suggests thermal resistance of the compounds. However, manufacture of sausages in this study (and within commercial conditions) involved a double thermal processing (cooking and post-cooking pasteurization). In addition, the use of permeable casing (cellulose) may had led to some leakage of the compounds during cooking, since steam was used and losses of weight in the product take place.

CONCLUSIONS

It is important to remark that lower concentrations of antimicrobials are usually required to achieve a particular inhibitory effect when laboratory media is used to test the potential of antimicrobial compounds. When antimicrobials are incorporated into food matrices a higher amount is usually needed to observed the same effect as in the laboratory since these matrices are compositionally more complex and their constituents can interact with the antimicrobial (Glass, K. A., et al., "Antagonistic Effect of Fat on The Antibotulinal Activity of Food Preservatives and Fatty Acids," *Food Microbiol*. 21:675-682 (2004), which is hereby incorporated by reference in its entirety). For example, Ma and others (Ma, Q., et al., "Antimicrobial Properties of Lauric Arginate Alone or in Combination with Essential Oils in Tryptic Soy Broth and 2% Reduced Fat Milk," *Int. J. Food Microbiol.* 166:77-84 (2013), which is hereby incorporated by reference in its entirety) reported that much higher concentrations of LAE were required to observe antimicrobial effect in 2% reduced fat milk compared to the microbial broth (tryptic soy broth). In this case the partitioning of LAE molecules into the lipid phase was argued, resulting in less LAE molecules available for a direct contact with *L. monocytogenes*. Consistent with this observation, in Example 20, bactericidal concentration of Avosafe® was observed at 15.6-31.2 ppm, while 10,000 ppm Avosafe® were required to observed a listericidal effect when incorporated into a model food system and stored at 4±1° C. (Example 23). Moreover, when an ingoing concentration of 10,000 ppm Avosafe® was incorporated into the raw formulation of the tested RTE meat product (sausages—Example 23), processing losses reduced the final concentration in the product and a bacteriostatic effect was observed during storage at 4±1° C.

The findings here provide appreciably new information about Avosafe® demonstrating that it can be successfully used in the formulation of RTE meats, including sausages, and that displays appreciable activity to control *Listeria monocytogenes* outgrowth. In addition, the present invention may allow meat processors to meet existing regulatory policies, while producing safer products that satisfy consumers demand. Further studies should be conducted to evaluate the impact, if any, of the levels of Avosafe® tested herein on the sensory and functional attributes of the finished food products.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A food product composition comprising:
a food product that is not avocado, and
an isolated inhibitor compound of either of the following formulae:

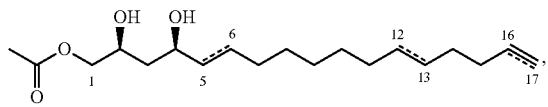

wherein the dashed lines are optional and represent a double bond or triple bond, and exactly one of the dashed lines is present, or

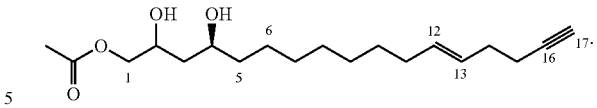

2. The food product composition of claim 1, wherein the isolated inhibitor compound in the composition is applied at a concentration of at least about 15.6 mg $L^{-1}$ to at least about 31.2 mg $L^{-1}$.

3. The food product composition of claim 1, wherein the food product is selected from the group consisting of fish, crustaceans, fish substitutes, crustacean substitutes, meat, meat substitutes, poultry products, vegetables, fruits, greens, sauces, emulsions, beverages, juices, wines, beers, dairy products, soups, egg-based products, dressings, jams, jellies, syrups, honeys, grain-based products, baked goods, snacks, confectionary products, purees, and combinations thereof.

4. The food product composition of claim 1, wherein the food product is a ready to eat food product stored under refrigerated conditions.

5. The food product composition of claim 1 further comprising:
an antimicrobial substance selected from the group consisting of nitrite compounds, nisin, bacteriocins, ethyl lauroyl arginate, ethylene diaminetetraacetic acid compounds, ascorbic acid compounds, benzoic acid compounds, lysosome, sorbic acid compounds, parabens, sulfur dioxide compounds, sulfite compounds, acetic acid compounds, boric acid compounds, lactic acid compounds, dimethyl dicarbonate, diethyl dicarbonate, natamycin, lactoferrin, fatty acids, esters, and combinations thereof.

6. A composition comprising an isolated inhibitor compound of either of the following formulae:

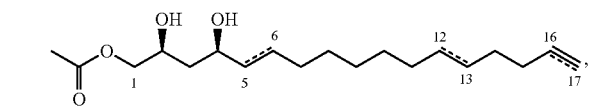

wherein the dashed lines are optional and represent a double bond or triple bond, and exactly one of the dashed lines is present, or

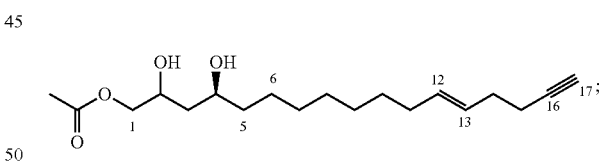

and any one or more of a pharmaceutically acceptable carrier, a food product that is not avocado, a personal care product, and a cleaning product.

* * * * *